(12) United States Patent
Schneeberger et al.

(10) Patent No.: US 7,279,617 B2
(45) Date of Patent: Oct. 9, 2007

(54) PROMOTER, PROMOTER CONTROL ELEMENTS, AND COMBINATIONS, AND USES THEREOF

(75) Inventors: Richard Schneeberger, Van Nuys, CA (US); Emilio Margolles-Clark, North Port, FL (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/234,633

(22) Filed: Sep. 22, 2005

(65) Prior Publication Data

US 2006/0107346 A1    May 18, 2006

Related U.S. Application Data

(60) Provisional application No. 60/612,603, filed on Sep. 22, 2004.

(51) Int. Cl.
*A01H 5/00* (2006.01)
*C07H 21/04* (2006.01)
*C12N 5/04* (2006.01)
*C12N 15/09* (2006.01)

(52) U.S. Cl. .................. 800/295; 435/320.1; 435/419; 435/6; 435/69.1; 435/468; 536/24.1; 800/278

(58) Field of Classification Search ............ None
See application file for complete search history.

(56) References Cited

OTHER PUBLICATIONS

Kim et al. (Plant Molecular Biology, 24:105-117, 1994).*
Guarente et al. (TIG, 8:27-32, 1992).*
Lin et al. (Plant Physiol., 106:477-484, 1994).*
Bargues et al. (NCBI, GenBank, Sequence Accession No. AL132978, pp. 1-51, Published Dec. 1, 1999).*
Lin Yun et al., "5 Proximal Regions of Arabidopsis Nitrate Reductase Genes Direct Nitrate-Induced Transcription in Transgeneic Tobacco" Plant Physiology (Rockville), vol. 106, No. 2, 1994, pp. 477-484, XP002380905.
Wang Rongchen et al., "Microarray Analysis of the Nitrate Response in Arabidopsis Roots and Shoots Reveals Over 1000 Rapidly Responding Genes and New Linkages to Glucose, Trehalose-6-Phosphate, Iron, and Sulfate Metabolism", Plant Physiology (Rockville), vol. 132, No. 2, Jun. 2003, pp. 556-567, XP002380906.
Coraggio I, et al., "Transcription and expression of Zein Sequences in Yeast Under Natural Plant or Yeast Promoters" NCBI, PubMed, Embo, J., Mar. 1986; 5(3), pp. 459-465.
Razik MA, et al. , "Effect on the Nuclear Factors EmBPI and Viviparous I on the Transcription of the Em Gene in HeLa Nuclear Extracts", NCBI, PubMed, Department of Biology, University of North Carolina, Plant Cell, Oct. 1997; 9 (10): pp. 1791-1803.
Lewin A. et al., "Gene Expression in Bacteria Directed By Plant-Specific Regulatory Sequences", Transgenic Research, vol. 7, No: 6, Jan. 1998, pp. 403-411(9).

* cited by examiner

*Primary Examiner*—Phuong T Bui
*Assistant Examiner*—Vinod Kumar
(74) *Attorney, Agent, or Firm*—Birch Stewart Kolasch & Birch

(57) ABSTRACT

The present invention is directed to nitrogen responsive promoter sequences and promoter control elements, polynucleotide constructs comprising the nitrogen responsive promoters and control elements and methods of identifying the nitrogen responsive promoters, control elements, or fragments thereof. The invention further relates to the use of the present nitrogen responsive promoters or promoter control elements to modulate transcript levels.

7 Claims, 8 Drawing Sheets

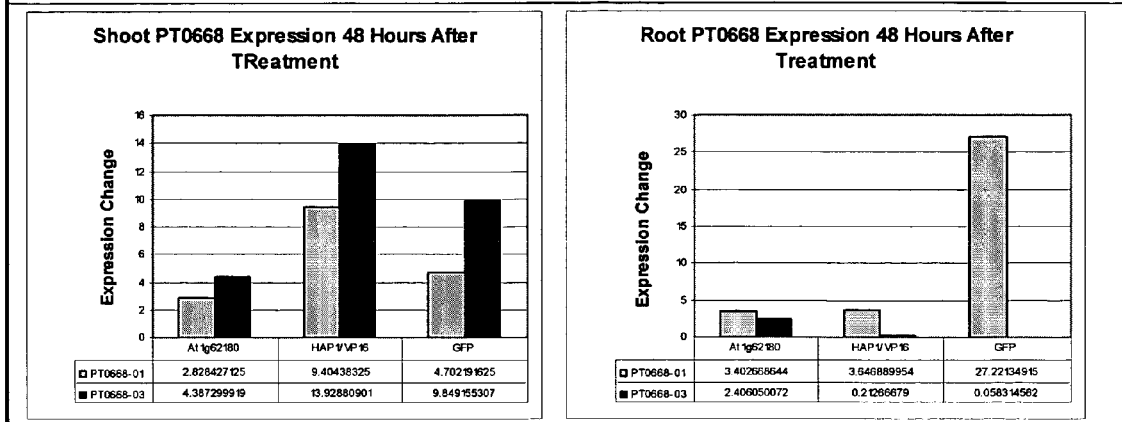
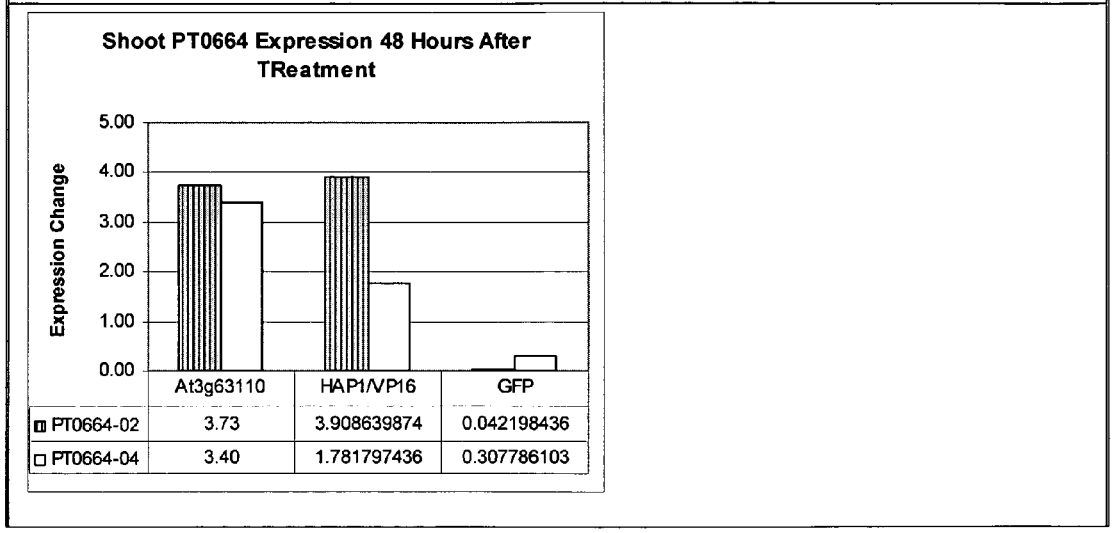

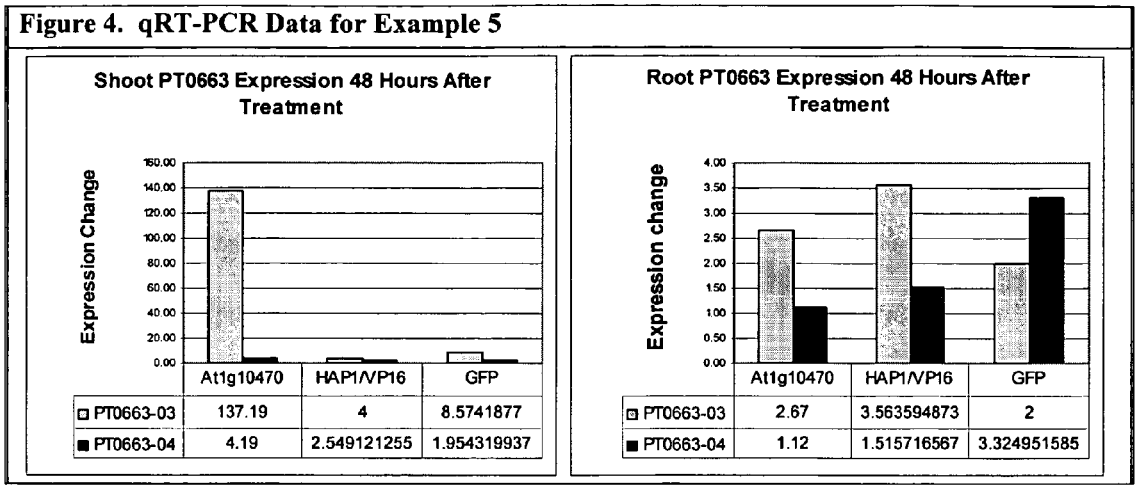
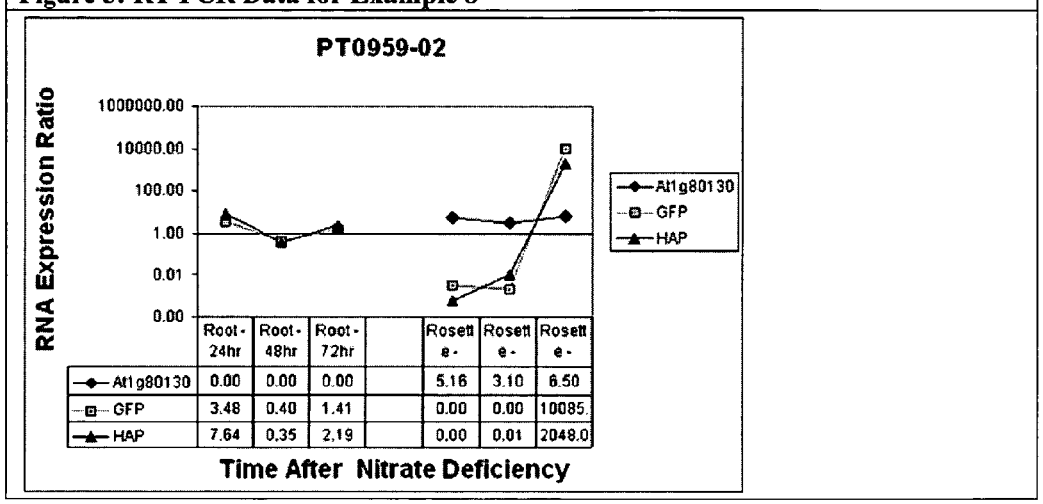

Figure 6 A Differential Expression of Selected Genes in Leaves for Example 9. The graphs show comparison of Fibrillarin-2 ratios obtained with qRT-PCR and microarray. Y-axis is ratio of experimental to control signal.

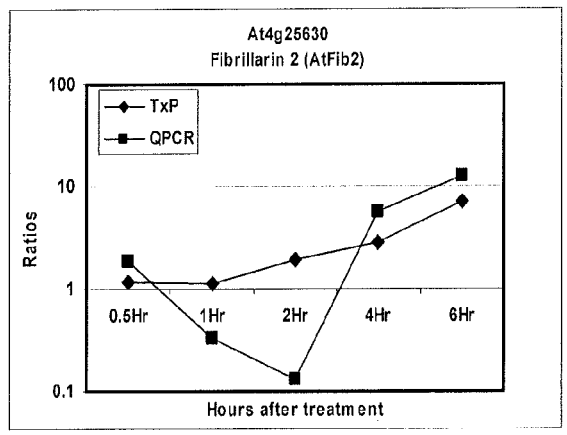

Figure 6 B Differential Expression of Selected Genes in Leaves for Example 9. The graphs show comparison of putative monodehydoascorbate reductase ratios obtained with qRT-PCR and microarray. Y-axis is ratio of experimental to control signal.

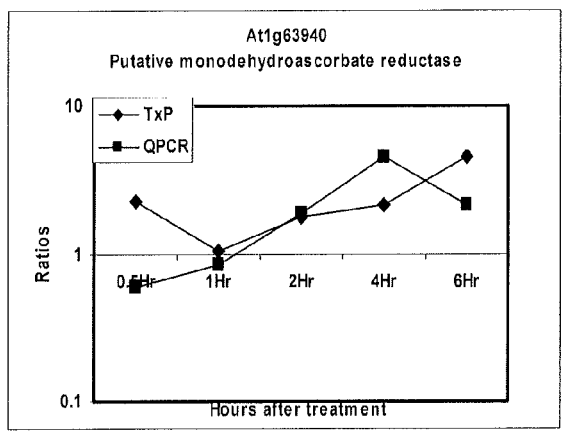

Figure 8 A. Differential Expression of Fibrillarin-2 in Roots and Shoots for Example 9. The nitrogen treated plants were cultivated in hydroponic conditions. Y-axis is ratio of experimental to control signal.

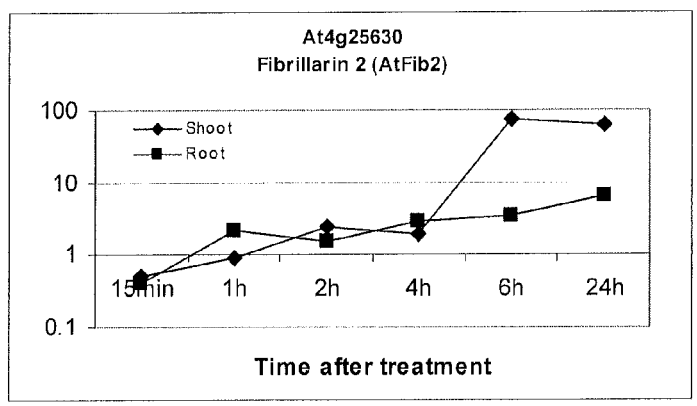

Figure 8 B. Differential Expression of putative monodehydroascorbate reductase in Roots and Shoots for Example 9. The nitrogen treated plants were cultivated in hydroponic conditions. Y-axis is ratio of experimental to control signal.

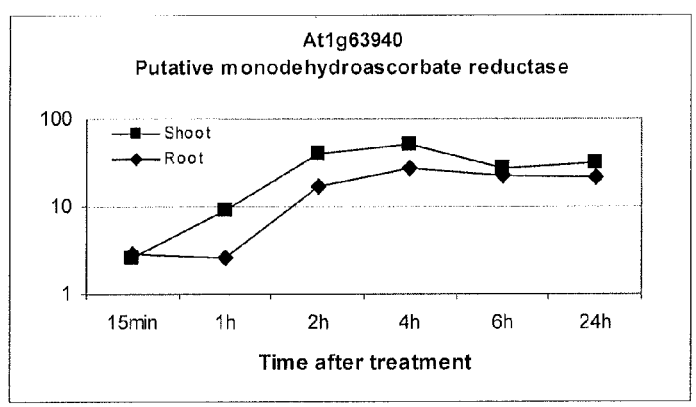

Figure 9 A. Differential expression in roots and shoots of T2 mature plants cultivated in hydroponic conditions for Example 9. Y-axis is the ratio of experimental to control signal. Putative monodehydroascorbate reductase =At1g63940.

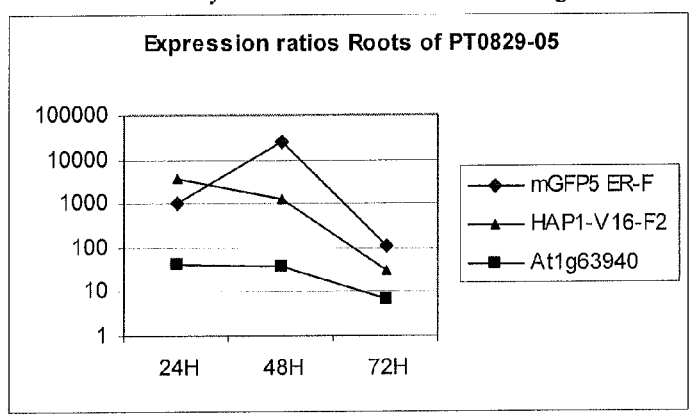

Figure 9 B. Differential expression in roots and shoots of T2 mature plants cultivated in hydroponic conditions for Example 9. Y-axis is the ratio of experimental to control signal. Fibrillarin-2 = At4g25630.

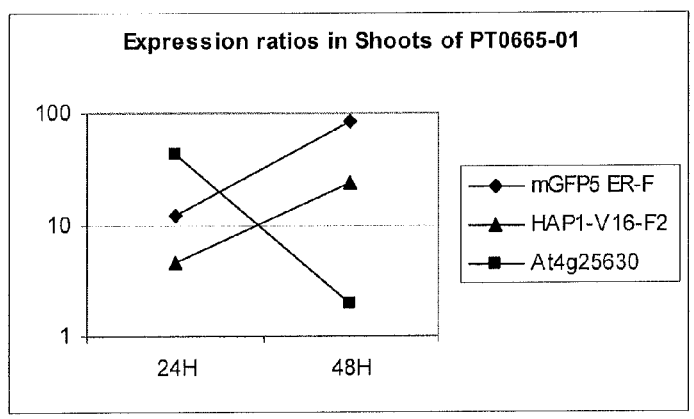

SCHEMATIC OF A GENE

PROMOTER, PROMOTER CONTROL ELEMENTS, AND COMBINATIONS, AND USES THEREOF

This Nonprovisional applications claims priority under 35 U.S.C. § 199 (e) on U.S. Provisional Application No. 60/612,603 filed on Sep. 22, 2004, the entire contents of which are hereby incorporated by reference.

This application contains one (1) CDR submitted in duplicate (totaling 3 CDs), created using IBM-PC MS-Windows operating system. The CD-Rs contain the following file(s):

| File Name | Date of Creation | File Size |
| --- | --- | --- |
| 2005-06-30_4980-1600PUS2.txt | Sep. 22, 2005 | 25KB |

FIELD OF THE INVENTION

The present invention relates to nitrogen responsive promoters and promoter control elements that are useful for modulating transcription of a desired polynucleotide. Such nitrogen responsive promoters and promoter control elements can be included in a polynucleotide construct, expression cassettes, vectors or inserted into the chromosome or used as an exogenous element to modulate in vivo and in vitro transcription of a polynucleotide. The invention also includes host cells and organisms, including plant cells and regenerated plants therefrom, with desired traits or characteristics obtained using polynucleotides comprising the nitrogen responsive promoters and promoter control elements of the present invention.

BACKGROUND OF THE INVENTION

Plants have a number of means to cope with nutrient deficiencies, such as poor nitrogen availability. They constantly sense nitrogen availability in the soil and respond accordingly by modulating gene expression. Although more is being discovered about nitrogen and the components involved in regulating its uptake and use, much is still unknown about many of these complex interactions. For this reason, it is interesting when a gene of known or unknown function is shown to have a nitrogen response, as it opens up new possibilities and insights into nitrogen use and nitrogen use efficiency in a competitive environment (i.e. low and/or high nitrogen).

Nitrogen regulated gene expression is an important aspect of a plant's response to changes in nitrogen availability. Nitrate acts as a signal to initiate a number of responses that serve to reprogram plant metabolism, physiology and development (Redinbaugh and Campbell, 1991; Forde, 2002). Nitrogen-inducible gene expression has been characterized for a number of genes in some detail. These include nitrate reductase, nitrite reductase, 6-phosphoglucante dehydrogenase, and nitrate and ammonium transporters (Redinbaugh and Campbell, 1991; Huber et al., 1994; Hwang et al., 1997; Redinbaugh and Campbell, 1998; Gazzarrini et al., 1999; Glass et al., 2002; Okamoto et al., 2003). Investigations into the cis acting control elements and DNA binding factors involved in nitrate regulated gene expression have focused on the nitrate reductase gene from tobacco and spinach and have identified several putative regulatory elements (Rastogi et al., 1993; Lin et al., 1994; Hwang et al., 1997). Transcriptional profiling of nitrate-regulated gene expression has extended knowledge of genes and processes regulated by nitrate availability and also identified a number of genes with distinct spatial and temporal patterns of expression (Ceres unpublished; Wang et al., 2000; Wang et al., 2003).

Nitrogen is most frequently the rate limiting mineral nutrient for crop production. Plants have evolved complex signaling and regulatory mechanisms to enable rapid physiological and metabolic response to changes in the supply of inorganic nitrogen in the soil. Part of this regulation is achieved through transcriptional regulation of gene expression. This is an important mechanism for allowing plants to adjust nitrogen uptake, reduction and transport in response to changing environmental conditions. Inefficiencies in nitrogen use efficiency may be overcome through the use of nitrogen regulated gene expression to modify the response of rate limiting enzymes and metabolic pathways to changes in nitrogen availability.

The ability to modify plant gene expression and ultimately the phenotype of a plant using nitrogen-inducible promoters can be a powerful method for deploying nitrogen transgene product concepts in the field. We have identified promoters that are induced in nitrogen starved *Arabidopsis* plants in response to nitrate provision as well as promoters that are induced by decreases in nitrate concentration.

SUMMARY OF THE INVENTION

The present invention is directed to isolated polynucleotide sequences that comprise nitrogen responsive promoters and promoter control elements from plants, especially *Arabidopsis thaliana, Glycine max, Oryza sativa,* and *Zea mays* used alone or in combination with other promoters and promoter control elements functional in plants.

It is an object of the present invention to provide isolated polynucleotides that are nitrogen responsive promoter, promoter control element and motif sequences. These promoter sequences comprise, for example, (1) a polynucleotide having a nucleotide sequence according to any one of SEQ ID NOs: 1-17 or a functional fragment thereof;

(2) a polynucleotide having a nucleotide sequence having at least 80% sequence identity to sequences shown in any one of SEQ ID NOs: 1-17 or a functional fragment thereof; and (3) a polynucleotide having a nucleotide sequence which hybridizes to those shown in any one of SEQ ID NOs: 1-17 under a condition establishing at least a Tm−20° C.

Nitrogen responsive promoter and promoter control element sequences of the present invention are capable of modulating preferential transcription under varying nitrogen conditions.

In another embodiment, the present nitrogen responsive promoters and promoter control elements are capable of serving as or fulfilling the function of a core nitrogen responsive promoter, a nitrogen responsive initiator site, a nitrogen responsive transcription binding site, a nitrogen responsive enhancer, a nitrogen responsive inverted repeat, a nitrogen responsive locus control region or a nitrogen responsive scaffold/matrix attachment region.

It is yet another object of the present invention to provide a polynucleotide that includes at least a first and a second promoter control element. The first promoter control element is a nitrogen responsive promoter control element sequence as discussed above and the second promoter control element is heterologous to the first control element.

Moreover, the first and second control elements are operatively linked. Such promoters may modulate transcript levels preferentially in a tissue or under particular conditions in addition to responding to nitrogen conditions.

In another embodiment, the present isolated polynucleotide comprises a nitrogen responsive promoter or promoter control element as described above, wherein the promoter or promoter control element is operatively linked to a polynucleotide to be transcribed.

In another embodiment of the present vector, the nitrogen responsive promoter or promoter control element of the instant invention is operatively linked to a heterologous polynucleotide that is a regulatory sequence.

It is another object of the present invention to provide a host cell comprising an isolated polynucleotide or vector as described above or fragment thereof. Host cells include bacterial, yeast, insect, mammalian, and plant. The host cell can comprise a nitrogen responsive promoter or promoter control element exogenous to the genome. Such a nitrogen responsive promoter can modulate transcription in cis- and/or in trans-.

In yet another embodiment, the present host cell is a plant cell capable of regenerating into a plant.

It is yet another embodiment of the present invention to provide a plant comprising an isolated polynucleotide or vector described above.

It is a further embodiment of the present invention to provide a plant comprising a nucleic acid encoding a nitrogen responsive promoter operatively linked to a coding sequence so that the coding sequence is ectopically overexpressed in the plant in response to sub-optimal, normal or abnormal nitrogen conditions, and the plant exhibits at least one of the following characteristics: improved performance, improved nitrogen responsiveness, faster rate of growth, greater fresh or dry weight at maturation, greater fruit or seed yield, higher tolerance to sub-optimal, normal or abnormal nitrogen conditions, greater germination rate under sub-optimal, normal or abnormal nitrogen conditions, reduced nitrogen needs or greater tolerance to excess nitrogen compred to a progenitor plant.

It is another object of the present invention to provide a method of modulating transcription in a sample that contains either a cell-free transcription system or a host cell. This method comprises providing a polynucleotide or vector according to the present invention as described above, and contacting the sample of the polynucleotide or vector with conditions that permit transcription.

In another embodiment of the present method, the polynucleotide or vector preferentially modulates nitrogen metabolism and utilization.

The present invention also provides a method of obtaining a plant enhanced in a product of a structural gene comprising growing a transformed plant resulting from transformation with a nitrogen responsive promoter or promoter control element selected from any one of SEQ ID NOs: 1-17 with or without at least one of the corresponding optional promoter fragments identified in Table 1 deleted therefrom, wherein the enhanced product of the structural gene in the transformed plant results from transcription of a structural gene modulated by the introduced promoter or promoter control element of any one of SEQ ID NOs: 1-17 with or without at least one of the corresponding optional promoter fragments identified in Table 1 deleted therefrom.

It is a further embodiment of the invention to provide a method of reducing the amount and/or frequency of fertilizer application to crop plants by providing a plant with a nitrogen responsive promoter or promoter control element selected from SEQ ID Nos: 1-17 with or without at least one of the corresponding optional promoter fragments identified in Table 1 deleted therefrom with improved characteristics over a progenitor plant.

Other and further objects of the present invention will be made clear or become apparent from the following description.

BRIEF DESCRIPTION OF THE FIGURES

FIG. 1 is a schematic representation of the vector pNewBin4-HAP1-GFP. The definitions of the abbreviations used in the vector map are as follows:

Figure 1:
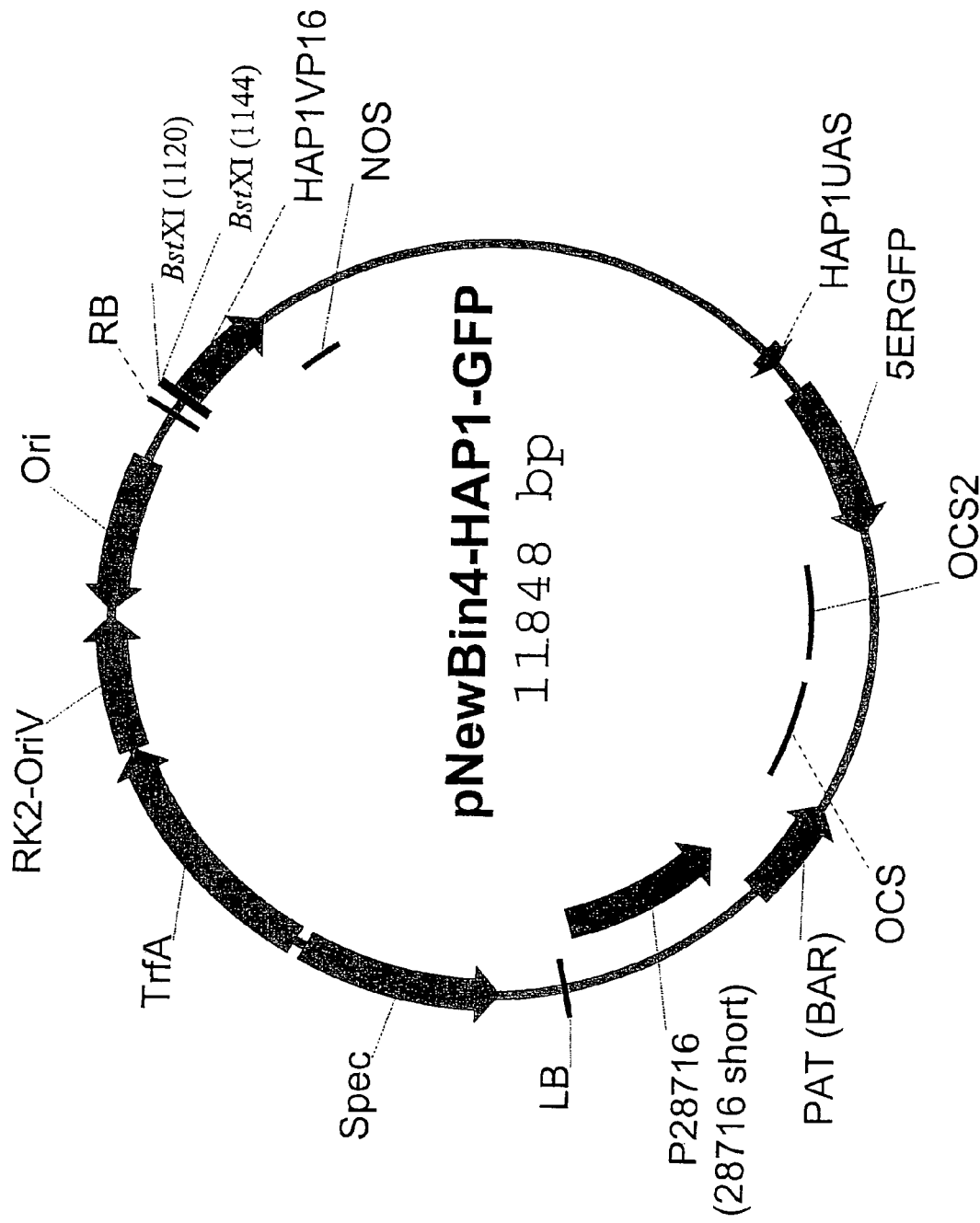
FIG. 1

Ori—the origin of replication used by an *E. coli* host
RB—sequence for the right border of the T-DNA from pMOG800
BstXI—restriction enzyme cleavage site used for cloning
HAP1VP16—coding sequence for a fusion protein of the HAP1 and VP16 activation domains
NOS—terminator region from the nopaline synthase gene
HAP1UAS—the upstream activating sequence for HAP1
5ERGFP—the green fluorescent protein gene that has been optimized for localization to the endoplasmic reticulum.
OCS2—the terminator sequence from the octopine synthase 2 gene
OCS—the terminator sequence from the octopine synthase gene
p28716 (a.k.a 28716 short)—promoter used to drive expression of the PAT (BAR) gene
PAT (BAR)—a marker gene conferring herbicide resistance
LB—sequence for the left border of the T-DNA from pMOG800
Spec—a marker gene conferring spectinomycin resistance
TrfA—transcription repression factor gene
RK2-OriV—origin of replication for *Agrobacterium*

FIG. 2

Quantitative RT-PCR Data for Example 3

FIG. 3

Quantitative RT-PCR Data for Example 4

FIG. 4

Quantitative RT-PCR Data for Example 5

FIG. 5

Quantitative RT-PCR Data for Example 8

FIG. 6A

Differential expression of Fibrillarin-2 in Leaves for Example 9.

FIG. 6B

Differential Expression of putative monodehydoascorbate reductase in Leaves for Example 9.

FIG. 7

Nitrate Content in growth media experimental and control plants hydroponically cultivated from Example 9.

FIG. 8A

Differential Expression of Fibrillarin-2 in Roots and Shoots for Example 9.

FIG. 8B

Differential Expression of putative monodehydroascorbate reductase in Roots and Shoots for Example 9.

FIG. 9A

Differential expression in roots and shoots of T2 mature plants cultivated in hydroponic conditions from Example 9: Putative monodedyhroascorbate reductase.

FIG. 9B

Differential expression in roots and shoots of T2 mature plants cultivated in hydroponic conditions from Example 9: Fibrillarin-2.

FIG. 10

Schematic representation of a gene.

DETAILED DESCRIPTION OF THE INVENTION

1. Definitions

Abnormal Nitrogen Conditions: Plant species vary in their capacity to tolerate particular nitrogen conditions. Nitrogen-sensitive plant species, including many agronomically important species, can be injured by nitrogen conditions that are either low or high compared to the range of nitrogen needed for normal growth. At nitrogen conditions above or below the range needed for normal growth, most plant species will be damaged. Thus, "abnormal nitrogen conditions" can be defined as the nitrogen concentration at which a given plant species will be adversely affected as evidenced by symptoms such as decreased chlorophyll (for example, measured by chlorophyll a/b absorbance) decreased photosynthesis (for example, measured by CO2 fixation, membrane damage (for example measured by electrolyte leakage) and chlorosis (for example, via visual inspection). Since plant species vary in their capacity to tolerate abnormal nitrogen conditions, the precise environmental conditions that cause nitrogen stress can not be generalized. However, nitrogen tolerant plants are characterized by their ability to retain their normal appearance or recover quickly from abnormal nitrogen conditions. Such nitrogen tolerant plants produce higher biomass and yield than plants that are not nitrogen tolerant. Differences in physical appearance, recovery and yield can be quantified and statistically analyzed using well known measurement and analysis methods.

Plant seeds vary considerably in their ability to germinate under abnormal nitrogen conditions. Generally, seeds of many plant species will not germinate at nitrogen concentration less than about 1 ppm or greater than about 2000 ppm. In addition, high concentrations of ammoniac nitrogen are also inhibitory to seed germination and can occur when ammonium based fertilizer is used (Brenner and Krogmeier (1989) PNAS 86:8185-8188).

Once seeds have imbibed water they become very susceptible to disease, water and chemical damage. Seeds that are tolerant to nitrogen stress during germination can survive for relatively long periods under which the nitrogen concentration is too high or too low to germinate. Since plant species vary in their capacity to tolerate abnormal nitrogen conditions during germination, the precise environmental conditions that cause nitrogen stress during germination can not be generalized. However, seeds and seedlings that are nitrogen tolerant during germination are characterized by their ability to remain viable or recover quickly from low or high nitrogen conditions. Such nitrogen tolerant plants germinate, become established, grow more quickly and ultimately produce more biomass and yield than plants that are not nitrogen tolerant. Differences in germination rate, appearance, recovery and yield can be quantified and statistically analyzed using well known measurement and analysis methods.

Chimeric: The term "chimeric" is used to describe polynucleotides or genes, as defined below, or constructs wherein at least two of the elements of the polynucleotide or gene or construct, such as the promoter and the polynucleotide to be transcribed and/or other regulatory sequences and/or filler sequences and/or complements thereof, are heterologous to each other.

Chimera: The term "chimera" refers to a cell or organism containing at least one chimeric polynucleotide, gene or construct.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Core Promoter: This is the minimal stretch of contiguous DNA sequence that is sufficient to direct accurate initiation of transcription by the RNA polymerase II machinery (for review see: Struhl, 1987, *Cell* 49: 295-297; Smale, 1994, In *Transcription: Mechanisms and Regulation* (eds R. C. Conaway and J. W. Conaway), pp 63-81/Raven Press, Ltd., New York; Smale, 1997, *Biochim. Biophys. Acta* 1351: 73-88; Smale et al., 1998, *Cold Spring Harb. Symp. Quant. Biol.* 58: 21-31; Smale, 2001, *Genes & Dev.* 15: 2503-2508; Weis and Reinberg, 1992, *FASEB J.* 6: 3300-3309; Burke et al., 1998, *Cold Spring Harb. Symp. Quant. Biol* 63: 75-82). There are several sequence motifs, including the TATA box, initiator (Inr), TFIIB recognition element (BRE) and downstream core promoter element (DPE), that are commonly found in core promoters, however not all of these elements occur in all promoters and there are no universal core promoter elements (Butler and Kadonaga, 2002, Genes & Dev. 16: 2583-2592).

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

Endogenous: The term "endogenous," within the context of the current invention refers to any polynucleotide, polypeptide or protein sequence which is a natural part of a cell or organisms regenerated from said cell. In the context of promoter, the term "endogenous coding region" or "endogenous cDNA" refers to the coding region that is naturally operatively linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below, and include Agrobacterium-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Functional Equivalent: This phrase describes a polynucleotide of sufficient length to retain at least one activity of the nitrogen responsive promoter or promoter control element.

Figure 10:
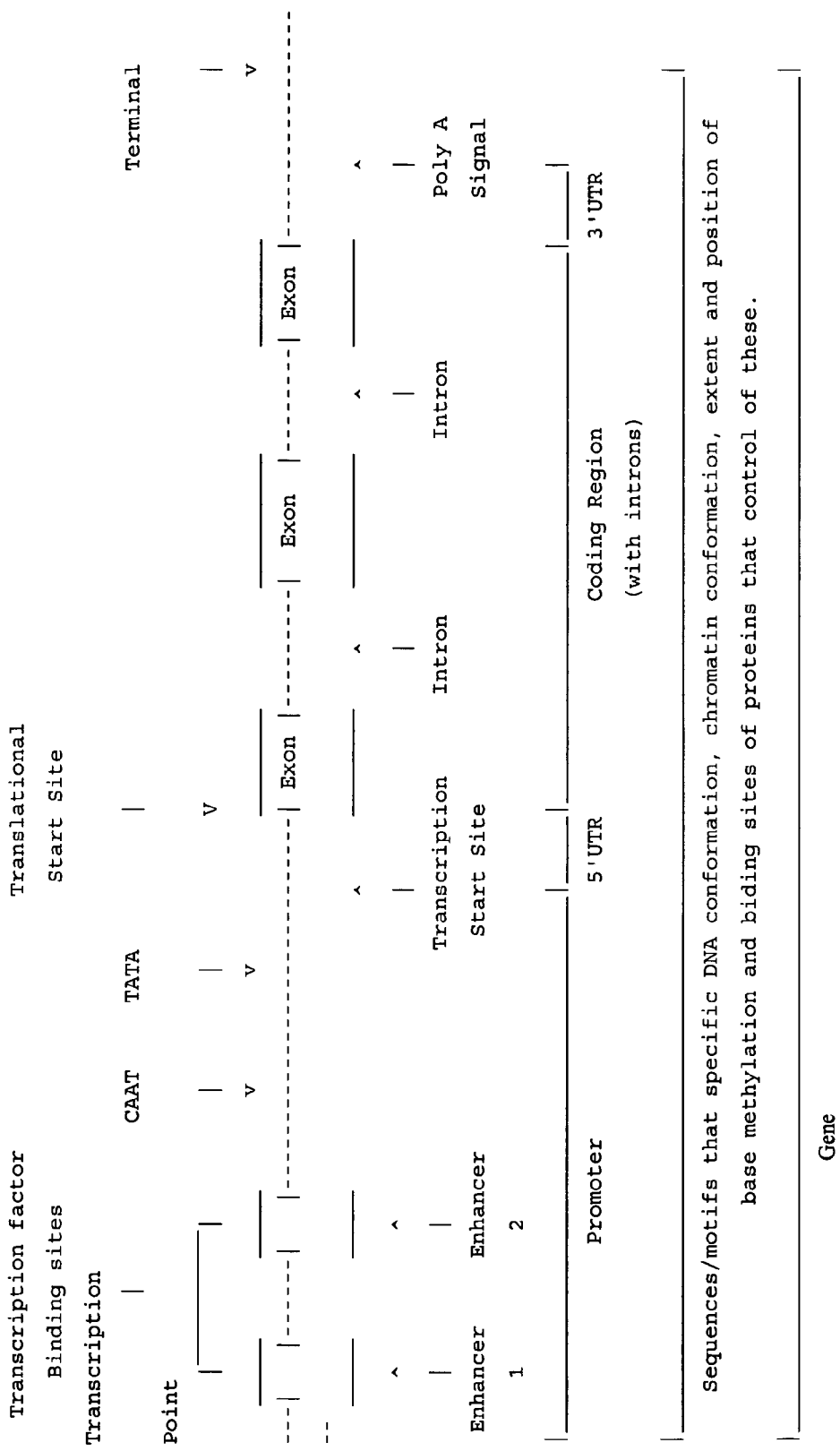

Gene: The term "gene," as used in the context of the current invention, encompasses all regulatory and coding sequence contiguously associated with a single hereditary unit with a genetic function (see FIG. 10). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

Heterologous sequences: "Heterologous sequences" are those that are not operatively linked or are not contiguous to each other in nature. For example, a promoter from corn is considered heterologous to an Arabidopsis coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present invention, is PARSK1, the promoter from an Arabidopsis gene encoding a serine-threonine kinase enzyme, and which promoter is induced by dehydration, abscissic acid and sodium chloride (Wang and Goodman, Plant J. 8:37 (1995)). Examples of environmental conditions that may affect transcription by inducible promoters include anaerobic conditions, elevated temperature, the presence or absence of a nutrient or other chemical compound or the presence of light.

Modulate Transcription Level: As used herein, the phrase "modulate transcription" describes the biological activity of a promoter sequence or promoter control element. Such modulation includes, without limitation, includes up- and down-regulation of initiation of transcription, rate of transcription, and/or transcription levels.

Motif: This phrase is used to describe a discrete sequence that is associated with a particular function. The sequence can be either nucleic acid or amino acid. It can also be either contiguous or capable of being aligned to certain positions that are invariant or conserved. For example, the motif GXGXXG is associated with nucleotide binding.

Mutant: In the current invention, "mutant" refers to a heritable change in nucleotide sequence at a specific location. Mutant genes of the current invention may or may not have an associated identifiable phenotype.

Normal Nitrogen Conditions: Plant species vary in their capacity to tolerate particular nitrogen conditions. Nitrogen-sensitive plant species, including many agronomically important species, can be injured by nitrogen conditions that are either low or high compared to the range of nitrogen needed for normal growth. At nitrogen conditions above or below the range needed for normal growth, most plant species will be damaged. Thus, "normal nitrogen conditions" can be defined as the nitrogen concentration at which a given plant species will grow without damage. Since plant species vary in their capacity to tolerate nitrogen conditions, the precise environmental conditions that provide normal nitrogen conditions can not be generalized. However, the normal growth exhibited by nitrogen intolerant plants is characterized by the inability to retain a normal appearance or to recover quickly from abnormal nitrogen conditions. Such nitrogen intolerant plants produce lower biomass and yield less than plants that are nitrogen tolerant. Differences in physical appearance, recovery and yield can be quantified and statistically analyzed using well known measurement and analysis methods.

Plant seeds vary considerably in their ability to germinate under nitrogen conditions. Generally, seeds of many plant species will not germinate at nitrogen concentration less than about 1 ppm or greater than about 2000 ppm. In addition, high concentrations of ammoniac nitrogen are also inhibitory to seed germination and can occur when ammonium based fertilizer is used (Brenner and Krogmeier (1989) PNAS 86:8185-8188).

Once seeds have imbibed water they become very susceptible to disease, water and chemical damage. Seeds that are intolerant to nitrogen stress during germination can only survive for relatively short periods under which the nitrogen concentration is too high or too low to germinate. Since plant species vary in their capacity to tolerate nitrogen conditions during germination, the precise environmental conditions that cause nitrogen stress during germination can not be generalized. However, the normal growth associated with nitrogen intolerant plants is characterized by the inability to remain viable or recover quickly from low or high nitrogen conditions. Such nitrogen intolerant plants do not germinate, do not become established, do grow more slowly, if at all, and ultimately die faster or produce less biomass and yield than plants that are nitrogen tolerant. Differences in germination rate, appearance, recovery and yield can be quantified and statistically analyzed using well known measurement and analysis methods.

Operable Linkage: An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operatively linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA or ribozyme, or (3) interfere with the ability of the DNA template to be transcribed. Thus, a promoter sequence would be operatively linked to a polynucleotide sequence if the promoter was capable of effecting transcription of that polynucleotide sequence.

Optimal Nitrogen Conditions: The optimal nitrogen concentration range is known for many crop plants. For example, and without limitation to the crops disclosed, the following nitrate nitrogen concentrations in the soil at a depth of 6 inches are considered optimal for the following crop plants: maize, 20-40 ppm; wheat, 5-20 ppm; cotton, 20-60 ppm; tomato, 35-50 ppm.

Optional Promoter Fragments: The phrase "optional promoter fragments" is used to refer to any sub-sequence of the promoter that is not required for driving transcription of an operationally linked coding region. These fragments comprise the 5' UTR and any exon(s) of the endogenous coding region. The optional promoter fragments may also comprise any exon(s) and the 3' or 5' UTR of the gene residing upstream of the promoter (that is, 5' to the promoter). Optional promoter fragments also include any intervening sequences that are introns or sequence that occurs between exons or an exon and the UTR.

Orthologous: "Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell).

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. The preceding references are hereby incorporated by reference in their entirety. Given that two sequences have been identified for comparison, GAP and BESTFIT are preferably employed to determine their optimal alignment. Typically, the default values of 5.00 for gap weight and 0.30 for gap weight length are used.

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of a polyadenylation (polyA) signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible via the internet). The database at the NCBI FTP site utilizes "gi" numbers assigned by NCBI as a unique identifier for each sequence in the databases, thereby providing a non-redundant database for sequence from various databases, including GenBank, EMBL, DBBJ, (DNA Database of Japan) and PDB (Brookhaven Protein Data Bank).

Regulatory Sequence: The term "regulatory sequence," as used in the current invention, refers to any nucleotide sequence that influences transcription or translation initiation and/or rate, and/or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, motifs, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least a 3-fold, preferably at least a 5-fold, more preferably at least a 10-fold still more preferably at least a 20-fold, 50-fold or 100-fold increase in transcript levels under the specific condition over the transcription under any one reference condition considered. Typical examples of temporal and/or tissue or organ specific promoters of plant origin that can be used with the polynucleotides of the present invention, are: PTA29, a promoter which is capable of driving gene transcription specifically in tapetum and only during anther development (Koltonow et al., Plant Cell 2:1201 (1990); RCc2 and RCc3, promoters that direct root-specific gene transcription in rice (Xu et al., Plant Mol. Biol. 27:237 (1995); TobRB27, a root-specific promoter from tobacco (Yamamoto et al., Plant Cell 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m = 81.5 - 16.6(\log_{10}[Na^+]) + 0.41(\% \; G+C) - (600/N) \tag{1}$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% \; G+C) - 500/L - 0.63(\% \; \text{formamide}) \tag{2}$$

where L is the length of the probe in the hybrid. (P. Tijessen, "Hybridization with Nucleic Acid Probes" in *Laboratory Techniques in Biochemistry and Molecular Biology*, P. C. vand der Vliet, ed., c. 1993 by Elsevier, Amsterdam, which is hereby incorporated by reference in its entirety). The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., J. Mol. Biol. 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

Suppressor: See "Enhancer/Suppressor"

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc). Likewise, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, 95, 97, 98, or 99% sequence identity. Variants preferably measure the primary biological function of the native polypeptide or protein or polynucleotide.

2. Introduction

The polynucleotides of the invention comprise nitrogen responsive promoters and promoter control elements that are capable of modulating transcription in response to nitrogen concentration, thereby enhancing the ability of a plant to grow under such nitrogen conditions.

Such nitrogen responsive promoters and promoter control elements can be used in combination with native or heterologous promoter fragments, control elements or other regulatory sequences to modulate transcription and/or translation.

Specifically, nitrogen responsive promoters and control elements of the invention can be used to modulate transcription of a desired polynucleotide, which include without limitation:

(a) antisense;
(b) ribozymes;
(c) coding sequences; or
(d) fragments thereof.

The nitrogen responsive promoter also can modulate transcription in a host genome in cis- or in trans-.

In an organism such as a plant, the nitrogen responsive promoters and promoter control elements of the instant invention are useful to produce preferential transcription which results in a desired pattern of transcript levels in a particular cell, tissue or organ, or under particular conditions.

3. Table of Contents

The following description of the present invention is outlined in the following table of contents.

A. Identifying and Isolating Promoter Sequences of the Invention
   (1) Cloning Methods
   (2) Chemical Synthesis
B. Generating a "Core" Promoter Sequence
C. Isolating Related Promoter Sequences
   (1) Relatives Based on Nucleotide Sequence Identity
   (2) Relatives Based on Coding Sequence Identity
   (3) Relatives based on Common Function
D. Identifying Control Elements
   (1) Types of Transcription Control Elements
   (2) Those Described by the Examples
   (3) Those Identifiable by Bioinformatics
   (4) Those Identifiable by In Vitro and In Vivo Assays
   (5) Non-Natural Control Elements
E. Constructing Promoters and Control Elements
   (1) Combining Promoters and Promoter Control Elements
   (2) Number of Promoter Control Elements
   (3) Spacing Between Control Elements
   (4) Other Promoters
F. Vectors
   (1) Modification of Transcription by Promoters and Promoter Control Elements
   (2) Polynucleotide to be Transcribed
   (3) Other Regulatory Elements
   (4) Other Components of Vectors
G. Insertion of Polynucleotides and Vectors into a Host Cell
   (1) Autonomous of the Host Genome
   (2) Integrated into the Host Genome
H. Utility A. Identifying and Isolating Promoter Sequences of the Invention The nitrogen responsive promoters and promoter control elements of the present invention are presented in the Sequence Listing. In addition, Table 1 describes the optional promoter control element motifs of the invention. Additional promoter sequences encompassed by the invention can be identified as described below.

(1) Cloning Methods

Isolation from genomic libraries of polynucleotides comprising the sequences of the nitrogen responsive promoters and promoter control elements of the present invention is possible using known techniques.

For example, polymerase chain reaction (PCR) can amplify the desired polynucleotides using primers designed from sequences in the row titled "The spatial expression of the promoter-marker-vector". Polynucleotide libraries comprising genomic sequences can be constructed according to Sambrook et al., *Molecular Cloning: A Laboratory Manual*, $2^{nd}$ Ed. (1989) Cold Spring Harbor Press, Cold Spring Harbor, N.Y., which is hereby incorporated by reference in its entirety), for example.

Other procedures for isolating polynucleotides comprising the nitrogen responsive promoters and promoter control elements sequences of the invention include, without limitation, tail-PCR and 5' rapid amplification of cDNA ends (RACE). See, for tail-PCR, for example, Liu et al., *Plant J* 8(3): 457-463 (September, 1995); Liu et al., *Genomics* 25: 674-681 (1995); Liu et al., *Nucl. Acids Res.* 21(14): 3333-3334 (1993); and Zoe et al., *BioTechniques* 27(2): 240-248 (1999); for RACE, see, for example, *PCR Protocols: A Guide to Methods and Applications*, (1990) Academic Press, Inc. These publications are hereby incorporated by reference in their entirety.

(2) Chemical Synthesis

In addition, the nitrogen responsive promoters and promoter control elements of the invention can be chemically synthesized according to techniques in common use. See, for example, Beaucage et al., *Tet. Lett.* (1981) 22: 1859 and U.S. Pat. No. 4,668,777.

Such chemical oligonucleotide synthesis can be carried out using commercially available devices, such as a Biosearch 4600 or 8600 DNA synthesizer (Applied Biosystems, a division of Perkin-Elmer Corp., Foster City, Calif., USA) and an Expedite (Perceptive Biosystems, Framingham, Mass., USA).

Synthetic RNA, including natural and/or analog building blocks, can be synthesized on the Biosearch 8600 machines, see above.

Oligonucleotides can be synthesized and then ligated together to construct the desired polynucleotide.

B. Generating Reduced and "Core" Promoter Sequences

Included in the present invention are reduced and "core" nitrogen responsive promoter sequences. The reduced promoters can be isolated from the promoters of the invention by deleting at least one sequence present in the promoter sequence that is associated with a gene or coding region located 5' or 3' to the promoter sequence or on the complementary strand.

Similarly, the "core" nitrogen responsive promoter sequences can be generated by deleting all sequences present in the promoter sequence that are related to the gene or coding region 5' or 3' to the promoter region or on the complementary strand.

This data is presented in Table 1 which identifies the particular regions which can be deleted from the sequences of SEQ ID NOs: 1-17 to provide reduced or "core" promoters. One or more, including all, such optimal promoter fragments can be deleted from SEQ ID NOs: 1-17 to produce the reduced or "core" promoters.

C. Isolating Related Promoter Sequences

Included in the present invention are nitrogen responsive promoters and promoter control elements that are related to those described in the Sequence Listing. Such a related sequence can be isolated utilizing
(a) nucleotide sequence identity;
(b) coding sequence identity; or
(c) common function or gene products.

Such related sequences (or "relatives") include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions since changes in the sequence can interfere with protein binding. Nonetheless, some variation in the functionally important regions is permissible so long as function is conserved.

The effects of substitutions, insertions and deletions to the nitrogen responsive promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are nitrogen responsive promoter and promoter control elements exhibiting nucleotide sequence identity to those described in the Sequence Listing.

Definition

Typically, such related promoters exhibit at least 80% sequence identity, at least 85%, at least 90%, or at least 95%, including, at least 96%, 97%, 98% or 99% sequence identity compared to those shown in the Sequence Listing. Such sequence identity can be calculated by the algorithms and computer programs described above.

Usually, such sequence identity is exhibited in an alignment region that is at least 75% of the length of a sequence shown in any one of SEQ ID NOs: 1-17 with or without at least one of the optional promoter fragments identified in Table 1 deleted therefrom; more usually at least 80%; more usually, at least 85%, more usually at least 90%, and most usually at least 95%, even more usually, at least 96%, 97%, 98% or 99% of the length of a sequence shown in any one of SEQ ID NOs: 1-17 with our without at least one of the optional promoter fragments identified in Table 1 deleted therefrom.

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence in the Sequence Listing.

These related promoters exhibit similar preferential transcription as those promoters described in the Sequence Listing.

Construction of Polynucleotides

Naturally occurring nitrogen responsive promoter and promoter control elements that exhibit nucleotide sequence identity to those shown in any one of SEQ ID NOs: 1-17 can be isolated using the techniques as described above. More specifically, such related promoters can be identified by varying stringencies, as defined above, in typical hybridization procedures such as Southern blots or hybridization of polynucleotide libraries, for example.

Non-natural nitrogen responsive promoter and promoter control element variants of those shown in any one of SEQ ID NOs: 1-17 with or without the optional promoter fragments of Table 1 deleted therefrom can be constructed using cloning methods that incorporate the desired nucleotide variation. See, for example, Ho, S. N., et al. Gene 77:51-59 1989, describing a procedure site directed mutagenesis using PCR.

Any related nitrogen responsive promoter and promoter control element showing sequence identity to those shown in any one of SEQ ID NOs: 1-17 with or without the optional promoter fragments of Table 1 deleted therefrom can be chemically synthesized as described above.

Also, the present invention includes non-natural nitrogen responsive promoter, promoter control elements and motifs that exhibit the above-sequence identity to those in any one of SEQ ID NOs: 1-17 with or without the optional promoter fragments of Table 1 deleted therefrom.

The nitrogen responsive promoter, promoter control elements and motifs of the present invention may also be synthesized with 5' or 3' extensions, to facilitate additional manipulation, for instance.

The present invention also includes reduced nitrogen responsive promoter sequences. These sequences have at least one of the optional promoter fragments deleted.

Core nitrogen responsive promoter sequences are another embodiment of the present invention. The core nitrogen responsive promoter sequences lack all of the optional promoter fragments.

Testing of Polynucleotides

Polynucleotides of the invention are tested for activity by cloning the sequence into an appropriate vector, transforming plants with the construct and assaying for marker gene expression. Recombinant DNA constructs are prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);

(b) YAC: Burke et al., Science 236:806-812 (1987);

(c) PAC: Sternberg N. et al., Proc Natl Acad Sci USA. January; 87(1):103-7 (1990);

(d) Bacteria-Yeast Shuttle Vectors: Bradshaw et al., Nucl Acids Res 23: 4850-4856 (1995);

(e) Lambda Phage Vectors: Replacement Vector, e.g., Frischauf et al., J. Mol. Biol 170: 827-842 (1983); or Insertion vector, e.g., Huynh et al., In: Glover N M (ed) DNA Cloning: A practical Approach, Vol. 1 Oxford: IRL Press (1985); T-DNA gene fusion vectors Walden et al., Mol Cell Biol 1: 175-194 (1990); and (g) Plasmid vectors: Sambrook et al., infra.

Typically, the construct comprises a vector containing a sequence of the present invention operationally linked to any marker gene. The polynucleotide is identified as a nitrogen responsive promoter by the expression of the marker gene under appropriate conditions. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin. Vectors can also include origins of replication, scaffold attachment regions (SARs), markers, homologous sequences, introns, etc.

Promoter Control Elements of the Invention

The nitrogen responsive promoter control elements and motifs of the present invention include those that comprise a sequence shown in any one of SEQ ID NOs: 1-17 and those that comprise fragments of those sequences shown in the Sequence Listing, but that still possess nitrogen responsive activity. The size of the fragments can range from 5 bases to 10 kilobases (kb). Typically, the fragment size is no smaller than 8 bases; more typically, no smaller than 12; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

E. Constructing Promoters with Control Elements (1) Combining Promoters and Promoter Control Elements The nitrogen responsive promoters, promoter control elements and/or motif sequences of the present invention, both naturally occurring and synthetic, can be combined with each other to produce the desired preferential transcription. Also, the polynucleotides of the invention can be combined with other known sequences to obtain other useful promoters to modulate, for example, tissue transcription specific or transcription specific to certain conditions. Such preferential transcription can be determined using the techniques or assays described above.

Fragments and variants, as well as the full-length sequences of those shown in any one of SEQ ID NOs: 1-17 and relatives are useful alone or in combination.

The location and relation of promoter control elements and motifs within a promoter affect the ability of the nitrogen responsive promoter to modulate transcription. The order and spacing of control elements is a factor when constructing promoters.

(2) Number of Promoter Control Elements

Nitrogen responsive promoters contain any number of control elements. For example, a nitrogen responsive promoter contains multiple transcription binding sites or other control elements. One element may confer tissue or organ specificity; another element may limit transcription to specific time periods, etc. Typically, nitrogen responsive promoters contain at least a basal or core promoter as described above. Any additional element is included as desired. For example, a fragment comprising a nitrogen responsive basal or "core" promoter is fused with another fragment with any number of additional control elements.

(3) Spacing Between Control Elements

Spacing between control elements or the configuration or control elements is determined or optimized to permit the desired protein-polynucleotide or polynucleotide interactions to occur.

For example, if two transcription factors bind to a promoter simultaneously or relatively close in time, the binding sites are spaced to allow each factor to bind without steric hindrance. The spacing between two such hybridizing control elements is as small as a profile of a protein bound to a control element. In some cases, two protein binding sites are adjacent to each other when the proteins bind at different times during the transcription process.

Further, when two control elements hybridize, the spacing between such elements is sufficient to allow the promoter polynucleotide to hairpin or loop to permit the two elements to bind. The spacing between two such hybridizing control elements is as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Such spacing between promoter control elements is determined using the techniques and assays described above.

(4) Other Promoters

The nitrogen responsive promoters and promoter control elements of the present invention can be combined in a construct with other known promoters to affect transcription in a desired manner. The following are promoters that are induced under stress conditions and can be combined with the polynucleotides of the present invention: ldh1 (oxygen stress; tomato; see Germain and Ricard. 1997. Plant Mol Biol 35:949-54), GPx and CAT (oxygen stress; mouse; see Franco et al. 1999. Free Radic Biol Med 27:1122-32), ci7 (cold stress; potato; see Kirch et al. 1997. Plant Mol. Biol. 33:897-909), Bz2 (heavy metals; maize; see Marrs and Walbot. 1997. Plant Physiol 113:93-102), HSP32 (hyperthermia; rat; see Raju and Maines. 1994. Biochim Biophys Acta 1217:273-80); MAPKAPK-2 (heat shock; Drosophila; see Larochelle and Suter. 1995. Gene 163:209-14).

In addition, the following examples are promoters induced by the presence or absence of light can be used in combination with the polynucleotides of the present invention: Topoisomerase II (pea; see Reddy et al. 1999. Plant Mol Biol 41:125-37), chalcone synthase (soybean; see Wingender et al. 1989. Mol Gen Genet 218:315-22) mdm2 gene (human tumor; see Saucedo et al. 1998. Cell Growth Differ 9:119-30), Clock and BMAL1 (rat; see Namihira et al. 1999. Neurosci Lett 271:1-4, PHYA (Arabidopsis; see Canton and Quail 1999. Plant Physiol 121:1207-16), PRB-1b (tobacco; see Sessa et al. 1995. Plant Mol Biol 28:537-47) and Ypr10 (common bean; see Walter et al. 1996. Eur J Biochem 239:281-93).

The nitrogen responsive promoters and promoter control elements of the following genes can be used in combination with the polynucleotides of the present invention to confer tissue specificity: MipB (iceplant; Yamada et al. 1995. Plant Cell 7:1129-42) and SUCS (root nodules; broadbean; Kuster et al. 1993. Mol Plant Microbe Interact 6:507-14) for roots, OsSUT1 (rice; Hirose et al. 1997. Plant Cell Physiol 38:1389-96) for leaves, Msg (soybean; Stomvik et al. 1999. Plant Mol Biol 41:217-31) for siliques, cell (Arabidopsis; Shani et al. 1997. Plant Mol Biol 34(6):837-42) and ACT11 (Arabidopsis; Huang et al. 1997. Plant Mol Biol 33:125-39) for inflorescence.

Still other promoters are affected by hormones or participate in specific physiological processes, which can be used in combination with the polynucleotides of present invention. Some examples are the ACC synthase gene that is induced differently by ethylene and brassinosteroids (mung bean; Yi et al. 1999. Plant Mol Biol 41:443-54), the TAPG1 gene that is active during abscission (tomato; Kalaitzis et al. 1995. Plant Mol Biol 28:647-56), and the 1-aminocyclopropane-1-carboxylate synthase gene (carnation; Jones et al. 19951 Plant Mol Biol 28:505-12) and the CP-2/cathepsin L gene (rat; Kim and Wright. 1997. Biol Reprod 57:1467-77), both active during senescence.

F. Vectors

Vectors are a useful component of the present invention. In particular, the present nitrogen responsive promoters and/or promoter control elements are delivered to a system such as a cell by way of a vector. For the purposes of this invention, such delivery may range from simply introducing the nitrogen responsive promoter and/or promoter control element by itself randomly into a cell, to integration of a cloning vector containing the present nitrogen responsive promoter and/or promoter control element. Thus, a vector is not to be limited to a DNA molecule such as a plasmid, cosmid or bacteria phage that has the capability of replicating autonomously in a host cell. All other manner of delivery of the nitrogen responsive promoters and promoter control elements of the invention are envisioned. The various T-DNA vector types are preferred vectors for use with the present invention. Many useful vectors are commercially available.

It may also be useful to attach a marker sequence to the present nitrogen responsive promoter or promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al., Nature 317: 741-744 (1985); Gordon-Kamm et al., Plant Cell 2: 603-618 (1990); and Stalker et al., Science 242: 419-423 (1988)). Other marker genes exist which provide hormone responsiveness.

(1) Modification of Transcription by Nitrogen Responsive Promoters, Promoter Control Elements The nitrogen responsive promoters and promoter control elements of the present invention are operatively linked to a polynucleotide to be transcribed. In this manner, the nitrogen responsive promoter or promoter control element modifies transcription by modulating transcript levels of that polynucleotide when inserted into a genome.

However, prior to insertion into a genome, the nitrogen responsive promoter or promoter control element need not be linked, operatively or otherwise, to a polynucleotide to be transcribed. For example, the nitrogen responsive promoter or promoter control element is inserted alone into the genome in front of a polynucleotide already present in the genome. In this manner, the nitrogen responsive promoter or promoter control element modulates the transcription of a polynucleotide that was already present in the genome. This polynucleotide may be native to the genome or inserted at an earlier time.

Alternatively, the nitrogen responsive promoter or promoter control element is inserted into a genome alone to modulate transcription. See, for example, Vaucheret, H et al. (1998) Plant J 16: 651-659. Rather, the nitrogen responsive promoter or promoter control element is simply inserted into a genome or maintained extrachromosomally as a way to divert transcription resources of the system to itself. This approach may be used to down-regulate the transcript levels of a group of polynucleotides.

(2) Polynucleotide to be Transcribed

The nature of the polynucleotide to be transcribed is not limited. Specifically, the polynucleotide includes sequences that have activity as RNA as well as sequences that result in a polypeptide product. These sequences include, but are not limited to, antisense sequences, ribozyme sequences, spliceosomes, amino acid coding sequences, and fragments thereof.

Specific coding sequences may include, but are not limited to endogenous proteins or fragments thereof, or heterologous proteins including marker genes or fragments thereof.

Nitrogen responsive promoters and promoter control elements of the present invention are useful for modulating metabolic or catabolic processes. Such processes include, but are not limited to, secondary product metabolism, amino acid synthesis, seed protein storage, oil development, pest defense and nitrogen usage. Some examples of genes, transcripts and peptides or polypeptides participating in these processes, which can be modulated by the present invention: are tryptophan decarboxylase (tdc) and strictosidine synthase (str1), dihydrodipicolinate synthase (DHDPS) and aspartate kinase (AK), 2S albumin and alpha-, beta-, and gamma-zeins, ricinoleate and 3-ketoacyl-ACP synthase (KAS), Bacillus thuringiensis (Bt) insecticidal protein, cowpea trypsin inhibitor (CpTI), asparagine synthetase and nitrite reductase. Alternatively, expression constructs are used to inhibit expression of these peptides and polypeptides by incorporating the nitrogen responsive promoters in constructs for antisense use, co-suppression use, RNAi suppression or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide according to the present invention for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present invention may contain additional components. For example, an origin of replication allows for replication of the vector in a host cell. Additionally, homologous sequences flanking a specific sequence allow for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the nitrogen responsive promoters and promoter control elements of the present invention. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of A. tumefaciens, such as the octopine synthase and nopaline synthase termination regions. See also, Guerineau et al., (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. 1989) Nucleic Acids Res. 17:7891-7903; Joshi et al. (1987) Nucleic Acid Res. 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436,391; see also and Murray et al., (1989) Nucleic Acids Res. 17:477-498.

Additional sequence modifications include elimination of sequences encoding spurious polyadenylation signals, exon intron splice site signals, transposon-like repeats, and other such sequences well characterized as deleterious to expression. The G–C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber, et al., "Vectors for Plant Transformation, in Methods in Plant Molecular Biology & Biotechnology" in Glich et al., (Eds. pp. 89-119, CRC Press, 1993). Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.). GFP vectors are available from Aurora Biosciences.

G. Insertion of Polynucleotide and Vectors into a Host Cell

The polynucleotides according to the present invention can be inserted into a host cell. A host cell includes but is not limited to a plant, mammalian, insect, yeast, and prokaryotic cell, preferably a plant cell.

The method of insertion into the host cell genome is chosen based on convenience. For example, the insertion into the host cell genome may be accomplished either by vectors that integrate into the host cell genome or by vectors which exist independent of the host cell genome (1) Polynucleotides Autonomous of the Host Genome The polynucleotides of the present invention exist autonomously or independent of the host cell genome. Vectors of these types are known in the art and include, for example, certain type of non-integrating viral vectors, autonomously replicating plasmids, artificial chromosomes, and the like.

Additionally, in some cases transient expression of a polynucleotide is desired.

(2) Polynucleotides Integrated into the Host Genome

The nitrogen responsive promoters, promoter control elements or vectors of the present invention may be transformed into host cells. These transformations may be into protoplasts or intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67-88 CRC Press, 1993); and by Phillips et al. "Cell-Tissue Culture and In-Vitro Manipulation" in Corn & Corn Improvement, 3rd Edition 10Sprague et al. (Eds. pp. 345-387) American Society of Agronomy Inc. et al. 1988.

Methods of introducing polynucleotides into plant tissue include the direct infection or co-cultivation of a plant cell with *Agrobacterium tumefaciens* (Horsch et al. (1985) Science 227:1229). Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "*Direct DNA transfer into intact plant cells via microprojectile bombardment*" In: Gamborg and Phillips (Eds.) Plant Cell, Tissue and Organ Culture: Fundamental Methods, Springer Verlag, Berlin (1995).

In another embodiment of the current invention, expression constructs are used for gene expression in callus culture for the purpose of expressing marker genes encoding peptides or polypeptides that allow identification of transformed plants. Here, a nitrogen responsive promoter that is operatively linked to a polynucleotide to be transcribed is transformed into plant cells, and the transformed tissue is then placed on callus-inducing media. If the transformation is conducted with leaf discs, for example, callus will initiate along the cut edges. Once callus growth has initiated, callus cells are transferred to callus shoot-inducing or callus root-inducing media. Gene expression occurs in the callus cells developing on the appropriate media: callus root-inducing promoters will be activated on callus root-inducing media, etc. Examples of such peptides or polypeptides useful as transformation markers include, but are not limited to, barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the exemplary nitrogen responsive promoters of any one of SEQ ID NOs: 1-17 with or without the optional promoter fragments of Table 1 deleted therefrom will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (A. C. Vergunst et al., *Plant Mol. Biol.* 38:393 (1998)).

H. Utility

Common Uses

In yet another embodiment, the nitrogen responsive promoters and/or promoter control elements of the present invention are used to further understand developmental mechanisms. For example, nitrogen responsive promoters and/or promoter control elements that are specifically induced during callus formation, somatic embryo formation, shoot formation or root formation are used to explore the effects of overexpression, repression or ectopic expression of target genes, or for isolation of trans-acting factors.

The vectors of the invention are used not only for expression of coding regions, but also in exon-trap cloning, or promoter trap procedures to detect differential gene expression in various tissues (K. Lindsey et al., 1993 "*Tagging Genomic Sequences That Direct Transgene Expression by Activation of a Promoter Trap in Plants*", Transgenic Research 2:3347. D. Auch & Reth, et al., "*Exon Trap Cloning: Using PCR to Rapidly Detect and Clone Exons from Genomic DNA Fragments*", Nucleic Acids Research, Vol. 18, No. 22, p. 674).

Entrapment vectors, first described for use in bacteria (Casadaban and Cohen, 1979, Proc. Nat. Aca. Sci. U.S.A., 76: 4530; Casadaban et al., 1980, J. Bacteriol., 143: 971) permit selection of insertional events that lie within coding sequences. Entrapment vectors are introduced into pluripotent ES cells in culture and then passed into the germline via chimeras (Gossler et al., 1989, Science, 244: 463; Skarnes, 1990, Biotechnology, 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. in Science 259:686-688 (1993), Mahan et al. in PNAS USA 92:669-673 (1995), Heithoff et al. in PNAS USA 94:934-939 (1997), and Wang et al. in PNAS USA. 93:10434 (1996).

Particular Uses

Nitrogen is often the rate-limiting element in plant growth, and all field crops have a fundamental dependence on exogenous nitrogen sources. Nitrogenous fertilizer, which is usually supplied as ammonium nitrate, potassium nitrate, or urea, typically accounts for 40% of the costs associated with crops, such as corn and wheat, in intensive agriculture. Increased efficiency of nitrogen use by plants enables the production of higher yields with existing fertilizer inputs and/or enables existing yields of crops to be obtained with lower fertilizer input, or provide for better yields on soils of poorer quality. Also, higher amounts of proteins in the crops are produced more cost-effectively. "Nitrogen responsive" promoters and/or promoter control elements are used to alter or modulate plant growth and development.

In addition, high concentrations of nitrogen are known to be toxic to plants, especially at the seedling stage (Brenner and Krogmeier (1989) PNAS 86:8185-8188). Here, abnormally high nitrogen creates toxic nitrogen effects ("burning") and/or leads to the inhibition of germination, reducing yield as a consequence. This is a particular problem during the application of urea and other ammonium based fertilizers since segments of a planting field can vary widely in terms of the available nitrogen present and high ammonium levels are toxic to plants. Currently, because most crop plants are severely damaged by high nitrogen conditions, yield can be significantly reduced.

Such deleterious effects can be avoided when the nitrogen responsive promoters and/or promoter control elements of the instant invention are used to direct expression of genes involved in ammonium assimilation and ion transport, as well as pH maintenance. As an example, the nitrogen responsive promoters and/or promoter control elements of the instant invention can be operatively linked to genes such as a ammonium transport Amt1 gene (Sonoda et al. (2003) Plant Cell Phys. 44:726-734) or to nitrate reductase (Loque et al. (2003) Plant Phys. 132:958-967; Gansel et al. (2001) Plant J. 26:143-155) in order to mitigate the effects of inadvertent over-application of urea fertilizer.

Nitrogen responsive promoter and/or promoter control element sequences are used in combination with gene coding sequences, either gDNA or cDNA, to induce the expression of proteins and enzymes during conditions of high or low soil or solution nitrogen concentration. Increased mRNA expression via one of the nitrogen responsive promoters and/or promoter control elements described herein is used to overcome rate limiting steps in nitrogen assimilation, transport and metabolism. General reviews of these processes can be found in: Derlot, S. et al., 2001, Amino Acid Transport. In *Plant Nitrogen* (eds. P. Lea and J.-F. Morot-Gaudry), pp. 167-212. Springer-Verlag, Berlin, Heidelberg, Glass, A. D. M et al., 2002, *J. Exp. Bot.* 53: 855-864, Krapp, A. et al., 2002, Nitrogen and Signaling. In *Photosynthetic Nitrogen Assimilation and Associated Carbon Respiratory Metabolism* (eds. C. H. Foyer and G. Noctor), pp. 205-225. Kluwer Academic Publisher, Dordrecht, The Netherlands, and Touraine, B. et al., 2001, Nitrate uptake and its regulation. In *Plant Nitrogen* (eds. P. Lea and J.-F. Morot-Gaudry), pp. 1-36. Springer-Verlag, Berlin, Heidelberg. Overcoming the rate limiting steps in nitrogen assimilation, transport and metabolism has the effect of increasing the yield, reducing the nitrogen content and reducing the protein content of plants grown under nitrogen limiting conditions.

Nitrogen responsive promoters and/or promoter control elements are also used to turn off the expression of genes that are not beneficial to nitrogen uptake, utilization and/or transport. Here, the nitrogen responsive promoter and/or promoter control element is operatively linked to the antisense orientation of a non-beneficial gene sequence. Expression of this antisense gene sequence has the effect of decreasing the amount of the non-beneficial sequence such that the expression of the protein encoded by the non-beneficial sequence is reduced. The reduction in expression of the non-beneficial sequence leads to a reduction in the genetic function of the protein, thus allowing for more efficient nitrogen uptake, utilization and transport (Hamada et al. 1996, Modification of fatty acid composition by over- and antisense-expression of a microsomal omega-3 fatty acid desaturase gene in transgenic tobacco. *Transgenic Res* 5: 115-121; Takahashi et al. 2001, Nitrite Reductase Gene Enrichment Improves Assimilation of NO2 in *Arabidopsis. Plant Physiol.* 126: 731-741; Temple et al. 1998, Down-regulation of specific members of the glutamine synthetase gene family in alfalfa by antisense RNA technology. *Plant Mol Biol* 37: 535-547). Alternatively, suppression of a non-beneficial gene sequence can be accomplished via co-suprression or RNAi suppression.

Nitrogen responsive promoters and/or promoter control elements are further used to express a non-beneficial sequence in inverted orientation, thus producing a double stranded RNA molecule. Double stranded RNAs are recognized in plant cells as foreign and are targeted for degradation (Vance and Vaucheret 2001, RNA Silencing in Plants—Defense and Counterdefense. *Science* 292: 2277-2280; Wesley et al. 2001, Construct design for efficient, effective and high-throughput gene silencing in plants. *Plant J* 27: 581-590.). The end result is reduced expression of the mRNA of the non-beneficial sequence, which leads to reduced gene function (Tang et al. 2003, A biochemical framework for RNA silencing in plants. *Genes Dev* 17: 49-63).

Nitrogen responsive promoters and/or promoter control elements that are expressed in the root are used to modify root architecture by increasing or decreasing the expression of genes involved in primary and lateral root formation. For example the ANR1 gene is involved in nitrogen dependent lateral root formation (Zhang and Forde 2000, Regulation of *Arabidopsis* root development by nitrate availability. *J. Exp. Bot.* 51: 51-59). Antisense inhibition of ANR1 gene expression results in a decrease in lateral root formation at inducing concentrations of nitrate (Zhang and Forde 1998, An *Arabidopsis* MADS box gene that controls nutrient-induced changes in root architecture. *Science* 279: 407-409.). Conversely, increased expression of ANR1 and other proteins involved in lateral root formation are used to increase lateral root number and length and thus increase nitrogen uptake from the soil or solution by increasing surface area contact between soil or solution and root absorbing surface.

The nitrogen responsive promoters and promoter control elements of the present invention are useful for modulating nitrogen metabolism and utilization. For example, the promoters and promoter control elements of the invention are used to increase the expression of nitrate and ammonium transporter gene products. These transporter gene products increase the uptake of nitrogen and transport of nitrogen from roots to shoots, which leads to an increase in the amount of nitrogen available for reduction to ammonia. As a consequence, such transgenic plants require less fertilizer, leading to reduced costs for the farmer and less nitrate pollution in ground water.

The nitrogen responsive promoters and promoter control elements of the invention also down-regulate genes which lead to feedback inhibition of nitrogen uptake and reduction. An example of such genes are those encoding the 14-3-3 proteins, which repress nitrate reductase (Swiedrych A et al., 2002, J Agric Food Chem 27;50(7):2137-41. *Repression of the* 14-3-3 *gene affects the amino acid and mineral compo-* sition of potato tuber). Here the nitrogen responsive promoters and promoter control elements described herein can be used to drive expression of an antisense copy of a 14-3-3 protein. The resulting transgenic plants have an increase in amino acid content and protein content in the seed and/or leaves. Such plants are especially useful for livestock feed. For example, an increase in amino acid and/or protein content in alfalfa provides an increase in forage quality and thus enhanced nutrition.

Generally, the nitrogen responsive promoters and/or promoter control elements of the invention can be used to improve plant performance when plants are grown under sub-optimal, normal or abnormal nitrogen conditions. For example, the transgenic plants of the invention can be grown without damage on soils or solutions containing at least 1, 2, 3, 4 or 5 percent less nitrogen, more preferably at least 5, 10, 20, 30, 40 or percent less nitrogen, even more preferably at least 60, 70 or 80 percent less nitrogen and most preferably at least 90 or 95 percent less nitrogen than normal, depending on the coding region operatively linked to the nitrogen responsive promoter or promoter control element of the invention. Similarly, the transgenic plants of the invention can be grown without damage on soils or solutions containing at least 1, 2, 3, 4 or 5 percent more nitrogen, more preferably at least 5, 10, 20, 30, 40 or 50 percent more nitrogen, even more preferably at least 60, 70 or 80 percent more nitrogen and most preferably at least 90 or 95 percent more nitrogen than normal, depending on the coding region operatively linked to the nitrogen responsive promoter or promoter control element of the invention.

GFP Experimental Procedures and Results

Procedures

The polynucleotide sequences of the present invention are tested for promoter activity using Green Fluorescent Protein (GFP) assays in the following manner.

Approximately 1-2 kb of genomic sequence occurring immediately upstream of the ATG translational start site of the gene of interest is isolated using appropriate primers tailed with BstXI restriction sites. Standard PCR reactions using these primers and genomic DNA are conducted. The resulting product is isolated, cleaved with BstXI and cloned into the BstXI site of an appropriate vector, such as pNew-Bin4-HAP1-GFP (see FIG. 1).

Transformation

The following procedure is used for transformation of plants

1. Seed Preparation and Plant Growth.

A homogeneous mixture of *Arabidopsis thaliana* seed in a 0.2% Phytagar solution is inclubated at 4° C. in the dark for 3 days. Seed is planted in 4 inch pots in a soil miture of Sunshine Mix, Vermiculite, Marathon and Osmocote. Pots are placed in flats, covered with plastic domes and subsequently subirrigated. After 3 to 4 days, the domes are removed.

Seven to ten days after planting, seedlings are thinned to 20 plants per pot. When 5-10 cm long bolts appear, they are clipped between the first node and the stem base to induce secondary bolts. Six to 7 days after clipping, the plants are transformed via dipping infiltration.

2. Preparation of *Agrobacterium*.

Each 4 inch pot is inverted and the aerial portion of the plants submerged into a 16 oz. polypropylene container holding 200 mls of *Agrobacterium tumefaciens* ($1 \times 10^7$ bacteria) in Infiltration media (2.2 g MS salts, 50 g sucrose, 110 µg BAP and 0.02% Silwet L-77 per liter). After 5 minutes, the *Agrobacterium* solution is removed while keeping the polypropylene contaniner in place and the pots returned to an upright position. Pots are then placed in flats (10 pots per flat) containing approximately 1 inch of water and covered with shade cloth. After 24 hours, the shade cloth and polypropylene containers are removed.

After flowering, each pot is covered with a ciber plant sleeve. When plants are completely dry, seed is collected and stored.

3. High Throughput Screening—T1 Generation

Transformed seed are placed in pots containing a water saturated soil miture of Sunshine Mix, Vermiculite, Marathon and Osmocote. Pots are then placed in flats and stored in the dark at 4° C. for at least 2 days. After transferring the flats from the cooler to the greenhouse, they are covered with 55% shade cloth and propagation domes. When the cotyledons are fully expanded the cloth and domes are removed.

Plants are sprayed with a solution of 3 ml concentrated Finale in 48 oz water. Spraying is repeated every 3-4 days until only transformants remain. Transformants are thinned to a maximum of 5 plants per pot.

4. GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | Pedicel, receptacle, nectary, sepal, petal, filament, anther, pollen, carpel, style, papillae, vascular, epidermis, stomata, trichome |
| Silique | Stigma, style, carpel, septum, placentae, transmitting tissue, vascular, epidermis, stomata, abscission zone, ovule |
| Ovule | Pre-fertilization: inner integument, outer integument, embryo sac, funiculus, chalaza, micropyle, gametophyte<br>Post-fertilization: zygote, inner integument, outer integument, seed coat, primordial, chalaza, miccropyle, early endosperm, mature endosperm, embryo |
| Embryo | Suspensor, preglobular, globular, heart, torpedo, late, mature, provascular, hypophysis, radicle, cotyledons, hypocotyl |
| Stem | Epidermis, cortex, vascular, xylem, phloem, pith, stomata, trichome |
| Leaf | Petiole, mesophyll, vascular, epidermis, trichome, primordial, stomata, stipule, margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal micsrocopy.

T2 Seedling: Progeny are collected from the T1 plants giving the same expression pattern and the progeny (T2) are sterilized and plated on agar-solidified medium containing M&S salts. In the event that there is no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings are screened until two seedlings are observed to have the same pattern. Generally found the same expression pattern is found in the first two seedlings. However, up to 6 seedlings are screened before "no expression pattern" is recorded. All constructs are screened as T2 seedlings even if they did not have an expression pattern in the T1 generation.

T2 Mature: The T2 mature plants are screened in a similar manner to the T1 plants. The T2 seeds are planted in the greenhouse, exposed to selection and at least one plant screened to confirm the T1 expression pattern. In instances where there are any subtle changes in expression, multiple plants are examined and the changes noted in the tables.

T3 Seedling: This is done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

An Inverted Leica DM IRB microscope is used with two Fluorescence filter blocks: (1) Blue excitation BP 450-490; long pass emission LP 515 and (2) Green excitation BP 515-560; long pass emission LP 590. The following objectives are used: HC PL FLUOTAR 5×/0.5, HCPL APO 10×/0.4 IMM water/glycerol/oil, HCPL APO 20×/0.7 IMM water/glycerol/oil and HCXL APO 63×/1.2 IMM water/glycerol/oil. A Leica TCS SP2 confocal scanner with a Spectral range of detector optics of 400-850 nm was used with a variable computer controlled pinhole diameter, an Optical zoom 1-32× and four simultaneous detectors: three channels for collection of fluorescence or reflected light and one channel for transmitted light detector. The laser sources are: (1) Blue Ar 458/5 mW, 476 nm/5 mW, 488 nm/20 mW, 514 nm/20 mW, (2) Green HeNe 543 nm/1.2 mW and (3) Red HeNe 633 nm/10 mW.

4. Quantitative PCR

Plants are staged according to Boyes et al. (2001) Plant Cell 13:1499-1510.

For experiments analyzing the response to changes from low to high Nitrogen concentrations, *Arabidopsis thaliana* (ecotype Wassilewskija) seeds are sown on flats containing 4 L of a 1:2 mixture of Grace Zonolite vermiculite and soil. Flats are watered with 3 L of water and vernalized at 4° C. for five days. Flats are placed in a Conviron growth chamber having 16 hr light/8 hr dark at 20° C., 80% humidity and 17,450 LUX. Flats are watered with approximately 1.5 L of water every four days. Mature, bolting plants (24 days after germination) are bottom treated with 2 L of either a control (100 mM mannitol pH 5.5) or an experimental (50 mM ammonium nitrate, pH 5.5) solution. Roots, leaves and siliques are harvested separately 30, 120 and 240 minutes after treatment, flash frozen in liquid nitrogen and stored at $-80°$ C.

Hybrid maize seed (Pioneer hybrid 35A19) are aerated overnight in deionized water. Thirty seeds are plated in each flat, which contained 4 liters of Grace zonolite vermiculite. Two liters of water are bottom fed and flats were kept in a Conviron growth chamber with 16 hr light/8 hr dark at 20° C. and 80% humidity. Flats are watered with 1 L of tap water every three days. Five day old seedlings are treated as described above with 2 L of either a control (100 mM mannitol pH 6.5) solution or 1 L of an experimental (50 mM ammonium nitrate, pH 6.8) solution. Fifteen shoots per time point per treatment are harvested 10, 90 and 180 minutes after treatment, flash frozen in liquid nitrogen and stored at $-80°$ C.

Alternatively, plants were cultivated hydroponically and submitted to low-to-high nitrate treatment. Plants were cultivated in a modified Hoagland's solution containing 15 ppm of nitrogen as KNO3 (1.7 mM KNO3) as the sole nitrogen (N) source. Plants were grown in a walk-in Conviron growth chamber under long day light cycle until they developed siliques and then transferred to 0.0 ppm N media for 3 days to adapt them to low nitrogen conditions. Nitrate induction was carried out by transferring experimental plants to 200 ppm of N (14.3 mM KNO3) and controls to 28.6 mM mannitol. Root and rosette tissue from experimental and control plants (2 plants each) were harvested at 0.25, 1, 2, 4, 6 and 24 hours after treatment.

For experiments analyzing the response to changes from high to low Nitrogen conditions, wild type *Arabidopsis thaliana* seeds (ecotype Wassilewskija) are surface sterilized with 30% Clorox, 0.1% Triton X-100 for 5 minutes. Seeds are then rinsed with 4-5 exchanges of sterile double distilled deionized water. Seeds are vernalized at 4° C. for 2-4 days in darkness. After cold treatment, seeds are plated on modified 1×MS media (without $NH_4NO_3$ or $KNO_3$), 0.5% sucrose, 0.5 g/L MES pH5.7, 1% phytagar and supplemented with $KNO_3$ to a final concentration of 60 mM (high nitrate modified 1×MS media). Plates are then grown for 7 days in a Percival growth chamber at 22° C. with 16 hr. light/8 hr dark.

Germinated seedlings are then transferred to a sterile flask containing 50 mL of high nitrate modified 1×MS liquid media. Seedlings are grown with mild shaking for 3 additional days at 22° C. in 16 hr. light/8 hr dark (in a Percival growth chamber) on the high nitrate modified 1×MS liquid media.

After three days of growth on high nitrate modified 1×MS liquid media, seedlings are transferred either to a new sterile flask containing 50 mL of high nitrate modified 1×MS liquid media or to low nitrate modified 1×MS liquid media (containing 20 µM $KNO_3$). Seedlings are grown in these media conditions with mild shaking at 22° C. in 16 hr light/8 hr dark for the appropriate time points and whole seedlings harvested for total RNA isolation via the Trizol method (LifeTech.). The time points used for the microarray experiments are 10 min. and 1 hour time points for both the high and low nitrate modified 1×MS media.

Alternatively, seeds that are surface sterilized in 30% bleach containing 0.1% Triton X-100 and further rinsed in sterile water, are planted on MS agar, (0.5% sucrose) plates containing 50 mM $KNO_3$ (potassium nitrate). The seedlings are grown under constant light (3500 LUX) at 22° C. After 12 days, seedlings are transferred to MS agar plates containing either 1 mM $KNO_3$ or 50 mM $KNO_3$. Seedlings transferred to agar plates containing 50 mM $KNO_3$ are treated as controls in the experiment. Seedlings transferred to plates with 1 mM $KNO_3$ are rinsed thoroughly with sterile MS solution containing 1 mM $KNO_3$. There are ten plates per transfer. Root tissue was collected and frozen in 15 mL Falcon tubes at various time points which included 1 hour, 2 hours, 3 hours, 4 hours, 6 hours, 9 hours, 12 hours, 16 hours, and 24 hours.

Maize 35A19 Pioneer hybrid seeds are sown on flats containing sand and grown in a Conviron growth chamber at 25° C., 16 hr light/8 hr dark, ~13,000 LUX and 80% relative humidity. Plants are watered every three days with double distilled deionized water. Germinated seedlings are allowed to grow for 10 days and are watered with high nitrate modified 1×MS liquid media (see above). On day 11, young corn seedlings are removed from the sand (with their roots intact) and rinsed briefly in high nitrate modified 1×MS liquid media. The equivalent of half a flat of seedlings is then submerged (up to their roots) in a beaker containing either 500 mL of high or low nitrate modified 1×MS liquid media (see above for details).

At appropriate time points, seedlings are removed from their respective liquid media, the roots separated from the shoots and each tissue type flash frozen in liquid nitrogen and stored at ⁻80° C. This is repeated for each time point. Total RNA is isolated using the Trizol method (see above) with root tissues only.

Corn root tissues isolated at the 4 hr and 16 hr time points are used for the microarray experiments. Both the high and low nitrate modified 1×MS media are used.

Quantitative RNA PCR (qt-PCR) was conducted according to standard procedures, for example using the Bio-Rad SYBR® Green qRT-PCR system.

EXAMPLES

The following Examples include various information about each nitrogen responsive promoter and/or promoter control element of the invention including the nucleotide sequence, the spatial expression promoted by each promoter and the corresponding results from different expression experiments.

Example 1

Promoter Expression Report #166.PT0625.FPNUE
Promoter Tested In: *Arabidopsis thaliana*, Wassilewskija (WS) ecotype
Spatial expression summary:
Primary Root        H epidermis
Observed expression pattern:
T1 mature: No expression
T2 seedling: Root specific GFP expression. High expression in root epidermal cells.
Expected expression pattern:    Shoots, Roots - Nitrogen inducible
Selection Criteria:             Microarray
Gene: *Arabidopsis thaliana* LOB domain protein 38
GenBank: NM_114854 *Arabidopsis thaliana* LOB domain protein 38/lateral organ boundaries domain protein 38 (LBD38) (At3g49940) mRNA, complete cds gi|18408982|ref|NM_114854.1
Source Promoter Organism:       *Arabidopsis thaliana*, Columbia (Col) ecotype
Vector:                         pNewbin4-HAP1-GFP
Marker Type:                    GFP-ER
Generation Screened:    XT1 Mature XT2 Seedling   T2 Mature   T3 Seedling
Inductions completed.

| Treatment: | Age: | Gen: | Time points: | Events Screened/ Response | Response: |
|---|---|---|---|---|---|
| 1. Minus N to 60 mM N (MS) | 12 d. | T2 | 2 Hr | 3/3 | Low |
|  |  |  | 6 Hr | 3/0 | No |
| 2. 100 µM KNO3 to 60 mM KNO3 | 12 d. | T2 | 24 Hr | 3/0 | No |
|  |  |  | 48 Hr | 3/0 | No |

Inducible expression summary:

| Treatment: | Time point induced: | Organs induced: | Tissues induced: |
|---|---|---|---|
| 1. Minus N to 60 mM N (MS) | 2 Hr | Root | vascular |

T1 Mature Plant Expression        Organs/Tissues screened
Events Screened:   n = 3          Events Expressing:  n = 0
No GFP Expression Detected
T2 Seedling Expression            Tissues Screened
Events Screened: n = 3            Events Expressing: n = 3
Seedlings expressing/Seedlings screened
Event-01: 5/6
Event-02: 5/6
Event-03: 5/6
GFP Expression Detected

| | |
|---|---|
| Hypocotyl | epidermis cortex vascular xylem phloem stomata |
| Cotyledon | mesophyll vascular epidermis margin stomata hydathode |
| Rosette Leaf | mesophyll vascular epidermis trichome petiole primordia stomata stipule margin hydathode |
| X Primary Root | H epidermis trichoblast atrichoblast cortex endodermis vascular xylem phloem pericycle quiescent columella root cap root hairs |
| Lateral root | epidermis trichoblast atrichoblast cortex endodermis initials flanking cells vascular lateral root cap |
| Shoot apical meristem | Shoot apical meristem |

-continued

X in the Epidermis (Ep) of the Root Transition zone and the Root (Rt)
Induction Screens
1. Minus N to 60 mM N (MS) 2 Hr and 6 Hr
At 2 Hrs, induction under 60 mM total Nitrogen (MS) conditions, no induction under
Minus N conditions.
At 6 HRs, induction under 60 mM total Nitrogen (MS) conditions, no induction under
Minus N conditions.
2. 100 μM KNO3 to 60 mM KNO3 24 Hr, 48 Hr
At 24 Hrs, induction under 60 mM KNO3 conditions, induction in 1 of three samples under
120 mM Mannitol conditions.
At 48 Hrs, induction under 60 mM KNO3 conditions, induction in 1 of three samples under
120 mM Mannitol conditions.
Promoter utility
Trait Area: Nutrient
Sub-trait Area: Nitrogen utilization, Low nitrogen tolerance, Nitrogen use efficiency
Utility: Among other uses this promoter sequence could be useful to improve: nitrogen
utilization by increasing the expression of nitrogen use efficiency genes in root epidermal tissue.
The promoter can also promoter greater uptake in response to locally high concentrations of
nitrate. The target genes could be in involved in processes that increase transport of nitrate,
ammonium and amino acids into the root e.g. nitrogen transporter proteins such as NRT2.1,
NRT1.1 or AMT1.1. This promoter can also be used to regulate the development of root hairs.
Increasing the number of root hairs can improve nutrient uptake.
Construct:              PT0625
Promoter candidate I.D: 13148207
cDNA I.D:               23643047
Events expressing:      PT0625 01-03 5(6)

Promoter region was PCR amplified from the Columbia ecotype of *A. thaliana*. Promoter construct sequence is 5' verified in T1 mature plants and confirmed in the following generation by 5' and 3' sequencing of the entire promoter of two or 3 events. Sequences from all events are used to generate a consensus sequence. In every case, the sequences of the 2-3 events have matched.

```
Promoter sequence

>166.PT0625 predicted (Ceres cDNA_13492462; SEQ ID NO:1)
ttaaccctaaacaaaacaatctcattggtttcataaataaattgtttacaaagtatacgt
actgcatgaacgaatgaaccatatctatatttataaaactcatagagaccaatagtttaa
gagaggcacttatatagctcaacaaataatagcgaactagagagaatatgatctaattag
ttataaatctcaattttgaaattgaagtgcgttatttcatttgagaatctatgtgttttt
tttgttgttgttagatgagaagctaggttttttctttctttacaccgataatcgataa
tatatgttaatcacactgattttgtttgagacatgaagattcgaaaaatttgtcaacga
ataaacactggatagatagaattgagatctgccatcaaataatcgagatcgttcatgcat
gacgcaaacatttatatagaaatgaagcaagtaaagaatatgaaaaagaatagaaatgag
aaatttataaagaaagaaaaaaagaaccaatggttgaggaggcaactattcgcggggaca
cggagccgttcgcacccatcaccttggaatctctctttcttcctctctcctcatcaccaa
ctagtcaacaaccacacaccattttttaactttcataattaaacctaacataacattttt
tttgtataaactatagcataaattaaattcagttaatgataaaataaatatatttgtag
caatcattctattttgtaatttggtagggctctttaaactttgattattatccaattttt
attaaaatataataaaatctcaaagccatgacccattccttcactcaagtatcaatgtct
attgtctataaatattacataactcttcttcttcaaccaaacattgaaacactttgtccc
actctctctctttctctttcttgtaccaaaagcttttgaatctccaagattatagcaaa
accaaagataaaatactaacttaaaagatttctgaaaata >166.PT0625 experimental (Ceres cDNA 23643047; SEQ ID NO:2)
gtaggcaaaaaaacgcctctatctttcttctaaaacattttcatattaaattatcaaaa
cccttaaggttgatttaagggtcaggtagtggatttgtttcgttgaagggtcagcttagc
cttaaccctaaacaaaacaatctcattggtttcataaataaattgtttacaaagtatacg
tactgcatgaacgaatgaaccatatctatatttataaaactcatagagaccaatagttta
agagaggcacttatatagctcaacaaataatagcgaactagagagaatatgatctaatta
gttataaatctcaattttgaaattgaagtgcgttatttcatttgagaatctatgtgtttt
ttttgttgttgttagatgagaagctaggttttttctttctttacaccgataatcgata
atatatgttaatcacactgattttgtttgagacatgaagattcgaaaaatttgtcaacg
aataaacactggatagatagaattgagatctgccatcaaataatcgagatcgttcatgca
tgacgcaaacatttatatagaaatgaagcaagtaaagaatatgaaaaagaatagaaatga
gaaatttataaagaaagaaaaaaagaaccaatggttgaggaggcaactattcgcggggac
acggagccgttcgcacccatcaccttggaatctctctttcttcctctctcctcatcacca
actagtcaacaaccacacaccattttttaactttcataattaaacctaacataacatttt
ttttgtataaactatagcataaattaaattcagttaatgataaaataaatatatttgta
gcaatcattctattttgtaatttggtagggctctttaaactttgattattatccaatttt
tattaaaatataataaaatctcaaagccatgacccattccttcactcaagtatcaatgtc
tattgtctataaatattacataactcttcttcttcaacca
```

Example 2

Promoter Expression Report #169.PT0669.FPNUE
Promoter Tested In: *Arabidopsis thaliana*, Wassilewskija (WS) ecotype
Spatial expression summary:

| | |
|---|---|
| Flower | H nectary |
| Silique | H stomata |
| Ovule | Post-fertilization: H early endosperm H embryo |
| Embryo | H radicle H cotyledons H mature |
| Rosette Leaf | H petiole |
| Primary Root | H epidermis H cortex H endodermis H vascular H pericycle H root cap L root hairs |
| Lateral root | H epidermis H cortex H endodermis H initials H primordia H vascular H lateral root cap |

Observed expression pattern:
T1 Mature expression: GFP is highly expressed throughout the female gametophyte, early endosperm and mature embryos. GFP is also expressed in nectarines of developing flowers, pollen, and guard cells in some siliques.
T2 Seedling expression: GFP is highly expressed throughout roots of seedlings. GFP also expressed in petioles of emerging rosette leaves.

| | |
|---|---|
| Expected expression pattern: | Shoots, Roots - Nitrogen inducible |
| Selection Criteria: | Microarray |
| Gene: | *Arabidopsis thaliana* ferredoxin, putative |
| GenBank: | NM_128311 *Arabidopsis thaliana* ferredoxin, putative (At2g27510) mRNA, complete |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling T2 Mature T3 Seedling |

| Treatment: | Age: | Gen: | Time points: | Events Screened/ Response | Response: |
|---|---|---|---|---|---|
| 1. 100 µM KNO3 to 20 mM KNO3 | 8 days | T2 | 24 Hr | 3/2 | Yes |
| | | | 48 Hr | 3/1 | |
| 2. 0.566 mM KNO3 to 30 mM KNO3 | 4 weeks | T2 | 48 Hr | 3/2 | Yes |

T1 Mature Plant Expression      Organs/Tissues screened
Events Screened:   n = 2          Events Expressing:   n = 2
GFP Expression Detected

| | |
|---|---|
| X Flower | pedicel receptacle H nectary sepal petal filament anther pollen carpel style papillae vascular epidermis stomata trichome |
| | silique |
| X Silique | stigma style carpel septum placentae funiculus transmitting tissue vascular epidermis H stomata abscission zone ovule |
| X Ovule | Pre-fertilization: primordia inner integument outer integument H embryo sac funiculus chalaza micropyle gametophyte Post-fertilization: zygote suspensor embryo sack funiculus inner integument outer integument endothelium seed coat primordia chalaza micropyle H early endosperm mature endosperm H embryo |
| X Embryo | suspensor preglobular globular heart torpedo late H mature provascular hypophysis H radicle H cotyledons root meristem shoot meristem |
| Stem | epidermis cortex interfascicular region vascular xylem phloem pith stomata trichome |
| Leaf | petiole mesophyll vascular epidermis trichome primordia stomata stipule margin |
| Shoot apical meristem | Shoot apical meristem Flower primordium |

X in the Nectary (Ne) of the flower, the Ovule/Ovary (Ov) and Pollen (Po) of the Silique (Si) and the Embryo sac (Es) of the prefertilized ovule.
X in the Guard cells (Gc) and Endosperm (En) of the Silique (Si).
X in the Root cap (Rc) of the embryo root.
X in the Seed.

T2 Seedling Expression          Tissues Screened
Events Screened: n = 3          Events Expressing: n = 3
Seedlings expressing/Seedlings screened
Event-01: 6/6
Event-02: 6/6
Event-03: 6/6
GFP Expression Detected

| | |
|---|---|
| Hypocotyl | epidermis cortex vascular xylem phloem stomata |
| Cotyledon | mesophyll vascular epidermis margin petiole stomata hydathode |
| X Rosette Leaf | mesophyll vascular epidermis trichome H petiole primordia stomata stipule margin hydathode |

| | |
|---|---|
| X Primary Root | H epidermis trichoblast atrichoblast H cortex H endodermis H vascular xylem phloem H pericycle quiescent columella H root cap L root hairs |
| X Lateral root | H epidermis trichoblast atrichoblast H cortex H endodermis H initials H primordia flanking cells H vascular H lateral root cap |
| Shoot apical meristem | Shoot apical meristem |
| X in all seedlings | |
| X in the Petiole (Pt), Lateral root (Lr) and Vasculature (Vs), Cortex (Cr), Endodermis (Eo), Epidermis (Ep) and Stele (Sl) of the root. | |
| X in the Root cap (Rc) of the root tip. | |
| Induction Screens | |
| 1. 100 µM KNO3 to 20 mM KNO3 Seedlings | |
| 24 Hrs | |
| Induction in roots under 20 mM KNO3 conditions, no induction under 40 mM Mannitol control conditions. | |
| 48 Hrs | |
| Induction in roots under 20 mM KNO3 conditions, no induction under 40 mM Mannitol control conditions. | |
| Induction Screens | |
| 0.566 mM KNO3 to 30 mM KNO3 Mature | |
| 48 Hrs | |
| Induction in flowers and roots under 20 mM KNO3 conditions, no induction under 60 mM Mannitol control conditions. | |
| 48 Hrs | |
| Increased GFP expression observed in petals, stamens and in embryos in event -01 under 30 mM KNO3 conditions. Petal (Pe), Pollen (Po), Sepal (Se), Root (Rt), Silique (Si), Stamen (St) No expression under 60 mM Mannitol control conditions. | |
| qRT-PCR Data | |
| Results: Tissues for QPCR were collected from stage 6.3-6.5 plants grown hydroponically. The QPCR results do not show highly inducible expression at either six hours or 48 hours after nitrate induction with the exception of events -02 and -03 at six hours after treatment in shoot and root. Event 1 also shows strong GFP induction at 48 hours after treatment. This pattern is consistent with the observed expression in flowers at 48 hours after treatment. | |
| Promoter utility | |
| Trait Area: Nutrient | |
| Sub-trait Area: Nitrogen utilization, Low nitrogen tolerance, Nitrogen use efficiency | |
| Utility: Among other uses this promoter sequence could be useful to improve: nitrogen utilization by increasing the expression of nitrogen use efficiency genes in root tissue in response to nitrogen fertilizer application. These genes can be in involved in processes that improve transport of nitrate, ammonium and amino acids. This promoter can also be used to increase expression of genes in seeds after nitrate fertilization. This can be useful for increasing transport of sucrose and amino acids to seeds and thereby increasing plant vigor and yield. | |
| Construct: | PT0669 |
| Promoter candidate I.D: | 15372193 |
| cDNA I.D: | 23373586 |
| Events expressing: | PT0669-01, -02, -03 |

Promoter region was PCR amplified from the Columbia ecotype of *A. thaliana*.) Promoter construct sequence is 5' verified in T1 mature plants and confirmed in the following generation by 5' and 3' sequencing of the entire promoter of two or 3 events. Sequences from all events are used to generate a consensus sequence.

```
Promoter sequence

>169.PT0669.FPNUE predicted (Ceres cDNA 12340498; SEQ ID NO:3)
aactatatttatatccgatttcattttcgcgaaacgagaaaatccaatgaaaaattaactcaa
gaaaaaaaaagttacgaaaacattttatttgtaattaaatgaatcatatataaaatcaaaaa
cagcagaataatggaaacaaataatctggtaggaaaaataatcaaataattaagacgtctcag
gtgacacaagttgggccgtcacggccttccaaaagccacactgctctctccttttatatattt
tgcttccacctctcaagactcctccaccaacccctctcgcactctccgccaccttcttccct
aattctctctctctcgctacctctctacgtaagtttcagatttgactttattagcttcgattc
tctctgatatttgtttctagaatttgatctgatcagcgatgtttacttgttccttgtttttg
tttttcattgacttcttgtggggacaaaaaaaaacaatcaaatatctttcgatttcgttgtt
cttctcttttcgttatctgatagtgaccgatttgatcctgtatcgttgctattcagatgcta
atcatctccttaattgtgaatttttttgttgttatttagtgaatcttgttacaagtctgttgt
aggtttattttgccattaagctactttgatcgactttagaatctatttgatgataagtaatt
aaacatgttttagtgattgttaagtaagtcatttagtcatgtttttggagcatcgagtgaaga
tctaatatagctttaagcttgcatcttctcattacgctccatacactaattttcacatcatat
ttgctattggaaacagataagttttggttcttgtttccattgctacttgtgatgcacatcct
cacaattttctctcagttttggttcttatttctctggaacagtttgatttgttagattgtatc
actatgaagaaaccctgaagctaaacttgtttataaacgcaggtgataaacaaga
```

-continued

| Promoter sequence |
|---|
| >169.PT0669.FPNUE experimental (Ceres cDNA 23373586; SEQ ID NO:4)<br>aactatatttatatccgatttcattttcgcgaaacgagaaaatccaatgaaaaattaactcaa<br>gaaaaaaaaagttacgaaaacattttatttgtaattaaatgaatcatatataaaatcaaaaa<br>cagcagaataatggaaacaaataatctggtaggaaaaataatcaaataattaagacgtctcag<br>gtgacacaagttgggccgtcacggccttccaaaagccacactgctctctcctttttatatattt<br>tgcttccacctctcaagactcctccaccaaccccctctcgcactctccgccaccttcttccct<br>aattctctctctcgctacctctcacgtaagtttcagatttgactttattagcttcgattc<br>tctctgatatttgtttctagaatttgatctgatcagcgatgtttacttgttccttgtttttg<br>tttttcattgacttcttgtggggacaaaaaaaaacaatcaaatatctttcgatttcgttgtt<br>cttctcttttcgttatctgatagtgaccgatttgatcctgtatcgttgctattcagatgcta<br>atcatctccttaattgtgaattttttttgttgttatttagtgaatcttgttacaagtctgttgt<br>aggtttattttttgccattaagctactttgatcgactttagaatctatttgatgataagtaatt<br>aaacatgttttagtgattgttaagtaagtcatttagtcatgttttggagcatcgagtgaaga<br>tctaatatagctttaagcttgcatcttctcattacgctccatacactaattttcacatcatat<br>ttgctattggaaacagataagttttggttcttgtttccattgctacttgtgatgcacatcct<br>cacaattttctctcagttttggttcttatttctctggaacagtttgatttgttagattgtaac<br>actatgaagaaaccctgaagctaaacttgtttataaacgcaggtgataaacaaga |

Example 3

Promoter Expression Report #170.PT0668.FPNUE
Promoter Tested In: *Arabidopsis thaliana*, Wassilewskija (WS) ecotype
Spatial expression summary:
Flower       H filament
Silique       H vascular H ovule
Ovule       Pre-fertilization: H outer integument H chalaza
           Post-fertilization: H outer integument H chalaza
Hypocotyl  L epidermis H vascular
Rosette Leaf  H epidermis
Observed expression pattern:
T1 Mature expression: GFP is preferentially expressed in chalazal region of the outer integument in developing ovules and seed coats. In flowers, GFP is also expressed in vasculature of carpels and connective region of anther filament. GFP is highly expressed in mesophyll and vasculature of leaves with weak expression in epidermal cells. Not expressed in cells of the stem.
T2 Seedling expression: GFP is highly expressed in epidermis and cortex cells of root, vascular cells of the hypocotyl and in the epidermis of leaves.
Expected expression pattern:   Shoots, Roots - Nitrogen inducible
Selection Criteria:         Microarray
Gene: 5'-adenylylsulfate reductase 2, chloroplast (APR2) (APSR)/adenosine 5'-phosphosulfate 5'-adenylylsulfate (APS) sulfotransferase, At1g62180.
GenBank: AK221838 *Arabidopsis thaliana* gene for putative adenosine-5'-phosphosulfate reductase, complete cds, clone: RAFL22-02-P09 gi|62321019|dbj|AK221838.1|[62321019]
Source Promoter Organism:   *Arabidopsis thaliana*, Columbia (Col) ecotype
Vector:                    pNewbin4-HAP1-GFP
Marker Type:           GFP-ER
Generation Screened:    X T1 Mature X T2 Seedling  T2 Mature   T3 Seedling

| Treatment: | Age: | Gen: | Time points: | Events Screened/ Response | Response: |
|---|---|---|---|---|---|
| 1. 100 µM KNO3 to 60 mM KNO3 | 7 days | T2 | 24 Hr | 4/1 | Yes |
|  |  |  | 48 Hr | 4/2 | Yes |
| 2. 0.566 mM KNO3 to 30 mM KNO3 | 4 weeks | T2 | 48 Hr | 2/1 | Yes |

T1 Mature Plant Expression    Organs/Tissues screened
Events Screened:   n = 2        Events Expressing:  n = 2
GFP Expression Detected
X Flower    Pedicel receptacle nectary sepal petal H filament anther
             pollen carpel style papillae vascular epidermis stomata
             trichome
             silique
X Silique   stigma style carpel septum placentae funiculus transmitting
             tissue H vascular epidermis stomata abscission zone H ovule
X Ovule    Pre-fertilization: primordia inner integument H outer integument
             embryo sac funiculus H chalaza micropyle gametophyte
             Post-fertilization: zygote suspensor embryo sack funiculus

|  | -continued |
|---|---|
|  | inner integument H outer integument endothelium seed coat primordia |
|  | H chalaza micropyle early endosperm mature endosperm embryo |
| Embryo | suspensor preglobular globular heart torpedo late mature provascular hypophysis radicle cotyledons root meristem shoot meristem |
| Stem | epidermis cortex interfascicular region vascular xylem phloem pith stomata trichome |
| X Leaf | petiole H mesophyll L vascular epidermis trichome primordia stomata stipule margin |
| Shoot apical meristem | Shoot apical meristem Flower primordium |

X in the Filament (Fi) and Ovule/Ovary (Ov) of the Flower.
X in the Vasculature (Vs) of the Silique (Si).
X in the Chalaza (Ch), Funiculus (Fn) and Outer integumenta (Oi) of the ovule.
X in the Mesophyll (Me) and Vasculature (Vs) of the leaf
X in the Seed coat (Sc) of the seed.
T2 Seedling Expression     Tissues Screened
Events Screened: n = 3     Events Expressing: n = 3
Seedlings expressing/Seedlings screened
Event-01: 2/6
Event-02: 2/6
Event-03: 7/7
GFP Expression Detected

| X Hypocotyl | L epidermis cortex H vascular xylem phloem stomata |
|---|---|
| Cotyledon | mesophyll vascular epidermis margin petiole stomata hydathode |
| X Rosette Leaf | mesophyll vascular H epidermis trichome petiole primordia stomata stipule margin hydathode |
| Primary Root | epidermis trichoblast atrichoblast cortex endodermis vascular xylem phloem pericycle quiescent columella root cap root hairs |
| Lateral root | epidermis trichoblast atrichoblast cortex endodermis initials primordia flanking cells vascular lateral root cap |
| Shoot apical meristem | Shoot apical meristem |

X in the Epidermis (Ep) and Vasculature (Vs) of the leaf, seedling and hypocotyl-root transition zone
Induction Screens
1. 100 µM KNO3 to 60 mM KNO3 11/19/2004
24 Hr and 48 Hr
Nitrate induced GFP expression is observed in cotyledons at 24 Hr and 48 Hr. under 60 mM KNO3 conditions.
2. 0.566 mM KNO3 to 30 mM KNO3      5/11/2005
Increase in GFP observed relative to control in the leaves of plants hydroponically grown at 0.566 mM KNO3 and treated in 30 mM KNO3
qRT-PCR Data
Results: Tissues for QPCR were collected from stage 6.3-6.5 plants grown hydroponically. Little to no nitrate-induced mRNA accumulation is observed at 6 hrs after nitrate induction except for event 4 in roots (the large values reported for 6 hour shoots could be due to very low levels of mRNA) Both events show strong nitrate induced mRNA accumulation of At1g62180, HAP1 and GFP transcripts in shoots and event -01 shows induction in roots. See FIG. 2
Promoter utility
Trait Area: Nutrient
Sub-trait Area: Nitrogen utilization, Low nitrogen tolerance, Nitrogen use efficiency
Utility: Among other uses this promoter sequence could be useful to improve: nitrogen utilization by increasing the expression of nitrogen use efficiency genes in leaf and seed tissue in response to nitrogen fertilizer application. These genes could be in involved in processes that increase photosynthesis, improve transport of nitrate, ammonium and amino acids and increase export of sucrose to sink tissues, thereby increasing plant vigor and yield.

| Construct: | PT0668 |
|---|---|
| Promoter candidate I.D: | 15372190 |
| cDNA I.D: | 23547574 |
| Events expressing: | -01, -02, -03 |

Predicted promoter region was PCR amplified from the Columbia ecotype of *A. thaliana*. Promoter construct sequence is 5' verified in T1 mature plants and confirmed in the following generation by 5' and 3' sequencing of the entire promoter of two or 3 events. Sequences from all events are used to generate a consensus sequence.

```
                       Promoter sequence (10000 bp).

>170.PT0668 predicted (Ceres cDNA 13610771; SEQ ID NO:5)
atagagttttactatgcttttggaatctttcttctaatgtgccaactacagagaaataca
tgtattaccactaggaatcggaccatatcatagatatcaggattagataactagttctcg
tcgctatcacttcgcattaagttctagtaattgttaaagattctaattttttactaaaca
aaaactaaatcaacatcaaatatgcaaagtgtgtgttgtccacacaagtgactcaaagta
tacgcaggtgggattggaccatattattgcaaatcgtttccgaaccactcatatttcttt
ttttctctccttttttatccggagaattatggaaccacttcatttcaacttcaaaacta
attttttggttcagtgatcaaatacaaaaaaaaaaaaaagttatagatattaaatagaa
aactattccaatcttaaaaatacaaatgaaaccataattttaatttatacaaaactattt
aattagctaagggttgtcttaacgtttagaaaataaaaaattatgattgtctgtttaaaa
ttacaatgaatgaataaaaaaaatatgcaatgaatgaaagaataaattttgtacatccga
tagaatgagaaaatgaattttgtacaaaccactcaagaattcaaaacaattgtcaaagtt
ttcttctcagccgtgtgtcctcctctcctagccgccacatctcacacactaatgctaacc
acgcgatgtaaccgtaagcgctgagttttgcatttcagatttcacttccaccaaacaaa
actcgccacgtcatcaatacgaatcattccgtataaacgtctagattctttacagcctac
aatgttctcttctttggtcggccattatttaacgctttgaacctaaatctagcccagcca
acgaagaagacgaagcaaatccaaaccaaagttctccattttcgtagcttctttaagctt
tttcagtatcatagagacacttttttttttttgattagaa >170.PT0668 experimental (Ceres cDNA 23547574; SEQ ID NO:6)
atagagttttactatgcttttggaatctttcttctaatgtgccaactacagagaaataca
tgtattaccactaggaatcggaccatatcatagatatcaggattagataactagttctcg
tcgctatcacttcgcattaagttctagtaattgttaaagattctaattttttactaaaca
aaaactaaatcaacatcaaatatgcaaagtgtgtgttgtccacacaagtgactcaaagta
tacgcaggtgggattggaccatattattgcaaatcgtttccgaaccactcatatttcttt
ttttctctccttttttatccggagaattatggaaccacttcatttcaacttcaaaacta
attttttggttcagtgatcaaatacaaaaaaaaaaaaaagttatagatattaaatagaa
aactattccaatcttaaaaatacaaatgaaaccataattttaatttatacaaaactattt
aattagctaagggttgtcttaacgtttagaaaataaaaaattatgattgtctgtttaaaa
ttacaatgaatgaataaaaaaaatatgcaatgaatgaaagaataaattttgtacatccga
tagaatgagaaaatgaattttgtacaaaccactcaagaattcaaaacaattgtcaaagtt
ttcttctcagccgtgtgtcctcctctcctagccgccacatctcacacactaatgctaacc
acgcgatgtaaccgtaagcgctgagttttgcatttcagatttcacttccaccaaacaaa
actcgccacgtcatcaatacgaatcattccgtataaacgtctagattctttacagcctac
aatgttctcttctttggtcggccattatttaacgctttgaacctaaatctagcccagcca
acgaagaagacgaagcaaatccaaaccaaagttctccattttcgtagcttctttaagctt
tttcagtatcatagagacacttttttttttttgattagaa
```

Example 4

Promoter Expression Report #174.PT0664.FPNUE
Promoter Tested In: *Arabidopsis thaliana*, Wassilewskija (WS) ecotype
Spatial expression summary:
Stem          H phloem
Leaf           L vascular
Hypocotyl    H vascular
Cotyledon    H vascular
Primary Root    L epidermis H vascular
Observed expression pattern:
T1 Mature expression: GFP expression specific to phloem cells within the vascular bundles of stem. Low GFP expression in vasculature of leaf.
T2 Seedling expression: GFP expressed in vasculature of hypocotyl and cotyledons and roots. Low root epidermal expression near transitions zone.
Expected expression pattern:    Shoots - Nitrogen inducible
Selection Criteria:         Microarray
Gene:              adenylate isopentenyltransferase 3/cytokinin synthase (IPT3)
GenBank: NM_116176 *Arabidopsis thaliana* adenylate isopentenyltransferase 3/cytokinin synthase (IPT3) (At3g63110) mRNA, complete cds gi|30695727|ref|NM_116176.2|[30695727]
Source Promoter Organism:     *Arabidopsis thaliana*, Columbia (Col) ecotype
Vector:                     pNewbin4-HAP1-GFP
Marker Type:            GFP-ER
Generation Screened:      XT1 Mature XT2 Seedling    T2 Mature    T3 Seedling Time -continued

| Treatment: | Age: | Gen: | points: | Events Screened/Response | Response: |
|---|---|---|---|---|---|
| 1. 100 uM KNO3 to 20 mM | 7 days | T2 | 24 Hrs | 4/2 | Yes |
|  |  |  | 48 Hrs | 4/0 | No |
| 2. 0.566 mM KNO3 to 30 mM KNO3 | 28 days | T2 | 48 Hrs | 2/0 | No |

T1 Mature Plant Expression    Organs/Tissues screened
Events Screened:    n = 2       Events Expressing:   n = 6
GFP Expression Detected

| | |
|---|---|
| Flower | pedicel receptacle nectary sepal petal filament anther pollen carpel style papillae vascular epidermis stomata trichome silique |
| Silique | stigma style carpel septum placentae funiculus transmitting tissue vascular epidermis stomata abscission zone ovule |
| Ovule | Pre-fertilization: primordia inner integument outer integument embryo sac funiculus chalaza micropyle gametophyte Post-fertilization: zygote suspensor embryo sack funiculus inner integument outer integument endothelium seed coat primordia chalaza micropyle early endosperm mature endosperm embryo |
| Embryo | suspensor preglobular globular heart torpedo late mature provascular hypophysis radicle cotyledons root meristem shoot meristem |
| X Stem | epidermis cortex interfascicular region vascular xylem H phloem pith stomata trichome |
| X Leaf | petiole mesophyll L vascular epidermis trichome primordia stomata stipule margin |
| Shoot apical meristem | Shoot apical meristem Flower primordium |

X in the Phloem (Ph) of the Stem
X in the Vascular (Vs) of the Leaf
T2 Seedling Expression       Tissues Screened
Events Screened: n = 3           Events Expressing: n = 3
Seedlings expressing/Seedlings screened
Event-01: 3/6
Event-02: 4/6
Event-02: 6/6
GFP Expression Detected

| | |
|---|---|
| X Hypocotyl | epidermis cortex H vascular xylem phloem stomata |
| X Cotyledon | mesophyll H vascular epidermis margin petiole stomata hydathode |
| Rosette Leaf | mesophyll vascular epidermis trichome petiole primordia stomata stipule margin hydathode |
| X Primary Root | L epidermis trichoblast atrichoblast cortex endodermis H vascular xylem phloem pericycle quiescent columella root cap root hairs |
| Lateral root | epidermis trichoblast atrichoblast cortex endodermis initials primordia flanking cells vascular lateral root cap |
| Shoot apical meristem | Shoot apical meristem |

X in the Vasculature (Vs) of the Seedling, Cotyledon, Hypocotyl-root Transition zone and the root.
X in the Epidermis (Ep) of the root.
Induction Screens
1. 100 uM KNO3 to 20 mM
Increased GFP response in roots relative to control in events 01 and 02.
Nitrate induced GFP expression was not observed in seedlings 48 hrs after treatment.
2. Mature plants Shoots and Roots: 0.566 mM KNO3 to 30 mM KNO3
Nitrate induced GFP expression was not observed in mature plants 48 hrs after treatment.
Promoter utility
Trait Area: Nutrient
Sub-trait Area: Nitrogen utilization, Low nitrogen tolerance, Nitrogen use efficiency
Utility: Among other uses this promoter sequence could be useful to improve: nitrogen utilization by increasing the expression of nitrogen use efficiency genes in vascular tissue in response to nitrogen fertilizer application. These genes can be in involved in processes that increase photosynthesis, improve transport of nitrate and amino acids and increase export of sucrose to sink tissues, thereby increasing plant vigor and yield.
qRT-PCR Data
Results: Tissues for QPCR were collected from stage 6.3-6.5 plants grown hydroponically. Little to no nitrate-induced mRNA accumulation is observed at 6 hrs after nitrate induction. Both events show mRNA induction of At3g63110, HAP1 in shoots 48 hrs after nitrate induction but GFP levels remain low. Event 4 shows high levels of induction of all three mRNA transcripts in 48 hrs after treatment of root tissue.

-continued

The data are broadly consistent with the GFP imaging results. See FIG. 3
Construct: PT0664
Promoter candidate I.D: 15372148
cDNA I.D: 23500661
Events expressing: -01, -02, -05

Predicted promoter region was PCR amplified from the Columbia ecotype of *A. thaliana*. Promoter construct sequence is 5' verified in T1 mature plants and confirmed in the following generation by 5' and 3' sequencing of the entire promoter of two or 3 events. Sequences from all events are used to generate a consensus sequence.

Promoter sequence (10000 bp).

>PT0664.FPNUE predicted (Ceres cDNA 12663481; SEQ ID NO:7)
tccaatagctatgacttgtcgctgtaagaataatcttttaaaggcccttctcggacca
ttatatttcttatctcatgtgaataattataatgtaataaaaaacaaaagttttctttgt
gttttttttcgtcttcagatttatatgtaagtggggagagtaataagagacgttcccggg
ggtctttggccattgcaggtcgacaaacaattttgcctctccgtttcattaatggacggt
ccaatagaacctttatattattctacaaatataaacaactctatgataatatcaaaatat
gagatagaatcacatctgcataacttttcttatgaaattagggaatacagaatatctat
atacatataatatttgatagaccgatcatgaggaggaagcatcataacctaatttcttaa
atgttttagttaaataatgtcaatccatccaaggtaattgccgagttttcattgcgac
tgctctaataacatgataaaatctattaaaaacaaatatactatgagcttagacaataac
ccatcaaaaaaaaataacccatatatatttttattaaaagaagagaaatgcttcttaaa
actttctgcctcgcatataatcgttattttcctagaaaaaaaatcgtatcttaacttcac
atcaaacgtaatagaagtttacgtttgattgtgacattatcaatatatatcatctgcatt
gcacgcggatcaaatatttggccagtctaaatagaattagaggagaataaagtaaaataa
aacaacaggtttgaccaattaattaaaaaaggggcgagccaacttgtcgtatatcattcg
tacagtggccatttactaagtgtgtgaccctatatatataaatcatatccttcatgcaaa
gtcacctgaacatttcatatataagaagatatacaagcctaccaaacataacaaaacata
ttttaaacaccagcaagtttatattgcaaagcgtttcatc >PT0664.FPNUE experimental (Ceres cDNA 23500661; SEQ ID NO:8)
tccaatagctatgacttgtcgctgtaagaataatcttttaaaggcccttctcggaccatta
tattcttatctcatgtgaataattataatgtaataaaaaacaaaagttttctttgtgttttt
tttcgtcttcagatttatatgtaagtggggagagtaataagagacgttcccggggtctttgg
ccattgcaggtcgacaaacaattttgcctctccgtttcattaatggacggtccaatagaacct
ttatattattctacaaatataaacaactctatgataatatcaaaatatgagatagaatcacat
ctgcataacttttcttatggaattagggaatacagaatatctatatacatataatatttgat
agaccgatcatgaggaggaagcatcataacctaatttcttaaatgttttagttaaataatgt
caatccatccaaggtaattgccgagttttcattgcgactgctctaataacatgataaaatct
attaaaaacaaatatactatgagcttagacaataacccatcaaaaaaaaataacccatatata
ttttattaaaagaagagaaatgcttcttaaaactttctgcctcgcatataatcgttattttt
cctagaaaaaaaatcgtatcttaacttcacatcaaacgtaatagaagtttacgtttgattgtg
acattatcaatatatatcatctgcattgcacgcggatcaaatgcttggccagtctaaatagaa
ttagaggagaataaagtaaaataaacaacaggtttgaccaattaattaaaaaaggggcgagcc
aacttgtcgtatatcattcgtacagtggccatttactaagtgtgtgaccctatatatataaat
catatccttcatgcaaagtcacctgaacatttcatatataagaagatatacaagcctaccaaa
cataacaaaacatattttaaacaccagcaagtttatattgcaaagcgtttcatc Example 5

Promoter Expression Report #182.PT0663.FPNUE
Promoter Tested In: *Arabidopsis thaliana*, Wassilewskija (WS) ecotype
Spatial expression summary:
Flower     H receptacle H pollen L vascular
Silique     H ovule
Ovule     Post-fertilization: H zygote H suspensor H embryo
            Pre-fertilization: H embryo sac
Embryo     H suspensor H preglobular H globular H late H mature H hypophysis H
            radicle
Stem     H vascular
Observed expression pattern:
T1 mature: High GFP expression in receptacle cells of flowers. GFP also expressed in vasculature of petals and stamens and in pollen. GFP expressed within the egg sac of prefertilized ovules and in 2 cell zygote through mature stage embryos. GFP preferentially expressed at the root cap in mature embryos. GFP also expressed in vasculature of stem.

-continued

T2 seedling: Standard screen not completed.
Expected expression pattern: Shoots - Nitrogen inducible
Selection Criteria: Microarray
Gene: two-component responsive regulator/response regulator 4 (ARR4)
GenBank: NM_100921 *Arabidopsis thaliana* two-component responsive regulator/response regulator 4 (ARR4) (At1g10470) mRNA, complete cds gi|30681723|ref|NM_100921.2
Source Promoter Organism: *Arabidopsis thaliana*, Columbia (Col) ecotype
Vector: pNewbin4-HAP1-GFP
Marker Type: GFP-ER
Generation Screened: X T1 Mature  T2 Seedling  T2 Mature  T3 Seedling

| Treatment: | Age: | Gen: | Time points: | Events Screened/ Response | Response: |
|---|---|---|---|---|---|
| 1. 100 μM KNO3 to 20 mMKNO3 | 7 days | T2 | 24 Hrs | 4/3 | Yes |
|  |  |  | 48 Hrs | 4/3 | Yes |
| 2. 0.566 mM KNO3 to 30 mM KNO3 | 4 weeks | T2 | 48 Hrs | 2/2 | Yes |

T1 Mature Plant Expression  Organs/Tissues screened
Events Screened:  n = 2          Events Expressing:  n = 3
GFP Expression Detected
X Flower     pedicel H receptacle nectary sepal petal filament anther H
             pollen carpel style papillae L vascular epidermis stomata
             trichome
             silique
X Silique    stigma style carpel septum placentae transmitting tissue
             vascular epidermis stomata abscission zone H ovule
X Ovule      Pre-fertilization: primordia inner integument outer integument
             H embryo sac funiculus chalaza micropyle gametophyte
             Post-fertilization: H zygote H suspensor embryo sack inner
             integument outer integument endothelium seed coat primordia
             chalaza micropyle early endosperm mature endosperm H embryo
X Embryo     H suspensor H preglobular H globular heart torpedo H late H mature
             provascular H hypophysis H radicle cotyledons hypocotyl
X Stem       epidermis cortex H vascular xylem phloem pith stomata
             trichome
Leaf         petiole mesophyll vascular epidermis trichome primordia
             stomata stipule margin
Shoot apical  Shoot apical meristem Flower primordium
meristem
X in the Receptacle (Re) of the inflorescence meristem.
X in the Receptacle (Re) and Vasculature (Vs) of the Flower.
X in the Ovule/Ovary (Ov) of the Silique (Si),.
X in the Embryo sac (Es) of the Silique and prefertilized ovule.
X in the Suspensor (Su) of the fertilized ovule and 2 cell globular embryo.
X in the Root (Rt) of the mature embryo
X in the Root cap (Rc) of the embryo root
X In the Vasculature (Vs), Phloem (Ph) and Xylem (Xy) of the stem.
Induction Screens
1. 100 μM KNO3 to 20 mMKNO3
24 Hrs.
Increased GFP response relative to control in events 02, 03 and 04, 24 hrs after nitrate induction.
48 Hrs.
Increased GFP expression in cotyledon tissues in events 02, 03 and 04, 48 hrs after nitrate induction
2. Mature plants Shoots and Roots - 0.566 mM KNO3 to 30 mM KNO3
Axillary meristem (Ax), Leaf (Lf) and Stem (Sm) tissues show response
Increased levels of GFP in epidermis and cortex cells of stem and epidermis and mesophyll cells of leaf. Cortex (Cr), Epidermis (Ep), Mesophyll (Me), Sepal (Se)
qRT-PCR Data
Results. Tissues for QPCR were collected from stage 6.3-6.5 plants grown hydroponically. Both events show mRNA induction in roots and shoots 48 hrs after treatment for the At1g10470, HAP1 and GFP transcripts. One of two events also show induction of At1g10470, HAP1 and GFP transcripts in root and shoot of 6 hour treated plants. The results are broadly correlated with the GFP imaging data. See FIG. 4
Promoter utility
Trait Area: Nutrient
Sub-trait Area: Nitrogen utilization, Low nitrogen tolerance, Nitrogen use efficiency
Utility: Among other uses this promoter sequence could be useful to improve: nitrogen utilization by increasing the expression of nitrogen use efficiency genes in leaf tissue in response to nitrogen fertilizer application. These genes can be in involved in processes that increase photosynthesis, improve transport of nitrate, animonium and amino acids and increase export of sucrose to sink tissues, thereby increasing plant vigor and yield. The promoter also shows expression in embryo sac and developing embryo and can be useful for modifying reproduction and seed characteristics.
Construct: PT0663
Promoter candidate I.D: 15372136
cDNA I.D: 12574427
Events expressing: 01, 02, 04, 05

Predicted promoter region was PCR amplified from the Columbia ecotype of *A. thaliana*. Promoter construct sequence is 5' verified in T1 mature plants and confirmed in the following generation by 5' and 3' sequencing of the entire promoter of two or 3 events. Sequences from all events are used to generate a consensus sequence

```
Promoter sequence (1000 bp).

>182.PT0663 predicted (Ceres cDNA 12574427; SEQ ID NO:9)
gggtccctcttttagatttccctgggtcccgcggatccaaattttaatgtggacgtcaaa
tcctttttttttattattatttgtccactttcctcttcttcttttttttttttttgccat
ttgaaaacgatataaataaaagtgtttggataacataaaatttctagagtcatatggatg
gatatactactagttaggcgtatactaattttctcgtcaacccacaaaacccgatcttaa
tattattctatgaattgcatttgaaccataaattttaaattagaaactgaccaatcacat
ggaacaatataaaattgtcttagtggttagtacttaatacaaataagaccaatccgaaga
accgagccggttaagtttaaacacgctactatgaattgtaatggtgtatgaccaaaatta
gcttctttaatcttctggtttattattcttaacagtgagtgattccattttcagtttttt
ttttccaatcacactaatgagtaatgacgagattttgactaagaagttgtatatatctca
cgatggtatattttatttttttggattcctttgtacggatttcttctcctctattattta
ttcgatttaggaatattattttctctatgatattcgcataggccctccaccggattttc
cataaaatctctatttattaatactattgttttcaaagataaaagttcaatttttcaac
cctaaaagcacggcacataaaaatatataattttcacattaataggaaccaaagattttg
ttggattttcctcgctggagattttcaaaataaaaattgaaaaaccaaaaagacacac
tcataaaagatttatttagagaacaaaaaaatcagaaatataaaaactgtcttaagga
agagaaaggaacaaaagaaaacagatgtgagctcttcttcttcgtcttcttctctctatt
ttattctcatcctctcctcacagttactataagctcgtct >182.PT0663 experimental (Ceres cDNA 23457514; SEQ ID NO:10)
gggtcccctttagatttccctgggtcccgcggatccaaattttaatgtggacgtcaaat
cctttttttattattatttgtccactttcctcttcttcttttttttttttttttgccat
ttgaaaacgatataaataaaagtgtttggataacataaaatttctagagtcatatggatg
gatatactactagttaggcgtatactaattttctcgtcaacccacaaaacccgatctta
atattattctatgaattgcatttgaaccataaattttaaattagaaactgaccaatcaca
tggaacaatataaaattgtcttagtggttagtacttaatacaaataagaccaatccgaag
aaccgagccggttaagtttaaacacgctactatgaattgtaatggtgtatgaccaaaatt
agcttctttaatcttctggtttattattcttaacagtgagtgattccattttcagttttt
ttttccaatcacactaatgagtaatgacgagattttgactaagaagttgtatatatctc
acgatggtatattttatttttggattcctttgtacggatttcttctcctctattattt
attcgatttaggaatattattttctctatgatattcgcataggccctccaccggatttt
ccataaaatctctatttattaatactattgttttcaaagataaaagttcaattttttcaa
ccctaaaagcacggcacataaaaatatataattttcacattaataggaaccaaagatttt
gttggattttcctcgctggagattttcaaaataaaaattgaaaaaccaaaaagacaca
ctcataaaagatttatttagagaacaaaaaaatcagaaatataaaaactgtcttaagg
aagagaaaggaacaaaagaaaacagatgtgagctcttcttcttcgtcttcttctctctat
tttattctcatcctctcctcacagttactataagctcgtct
```

Example 6

Promoter Expression Report 282.#PT0863.FPNUE
Promoter Tested In: *Arabidopsis thaliana*, Wassilewskija (WS) ecotype
Spatial expression summary:
Primary Root      H epidermis
Observed expression pattern:
T1 Mature expression: No observed expression.
T2 Seedling expression: GFP expression specific to root. Preferentially expressed in epidermal cells of primary roots in seedlings. Not observed in lateral roots.
Expected expression pattern:   Shoots - Nitrogen inducible
Selection Criteria:           Microarray
Gene: glucose-6-phosphate 1-dehydrogenase, putative/G6PD, putative
GenBank: NM_102274 *Arabidopsis thaliana* glucose-6-phosphate 1-dehydrogenase, putative/G6PD, putative (At1g24280) mRNA, complete cds
Source Promoter Organism:   *Arabidopsis thaliana*, Columbia (Col) ecotype
Vector:                       pNewbin4-HAP1-GFP
Marker Type:             GFP-ER
Generation Screened:     X T1 Mature X T2 Seedling  T2 Mature  T3 Seedling

| Treatment: | Age: | Gen: | Time points: | Events Screened/Response | Response: |
|---|---|---|---|---|---|
| 1. 100 µM KNO3 to 20 mM KNO3 | 7 days | T2 | 24 Hrs | 4/0 | No |
|  |  |  | 48 Hrs | 4/1 | Yes |
| 2. 0.566 mM KNO3 to 30 mM KNO3 | 28 days | T2 | 48 Hrs | 4/2 | Yes |

T1 Mature Plant Expression      Organs/Tissues screened
Events Screened:   n = 3      Events Expressing:  n = 0
No GFP Expression Detected -continued

| | |
|---|---|
| T2 Seedling Expression | Tissues Screened |
| Events Screened: n = 3 | Events Expressing: n = 2 |
| Seedlings expressing/Seedlings screened | |
| Event-01: 3/6 | |
| Event-02: 3/6 | |
| Event-03: 0/6 | |
| GFP Expression Detected | |
| Hypocotyl | epidermis cortex vascular xylem phloem stomata |
| Cotyledon | mesophyll vascular epidermis margin petiole stomata hydathode |
| Rosette Leaf | mesophyll vascular epidermis trichome petiole primordia stomata stipule margin hydathode |
| X Primary Root | H epidermis trichoblast atrichoblast cortex endodermis vascular xylem phloem pericycle quiescent columella root cap root hairs |
| Lateral root | epidermis trichoblast atrichoblast cortex endodermis initials primordia flanking cells vascular lateral root cap |
| Shoot apical meristem | Shoot apical meristem |

X in the Epidermis (Ep) of the Root transition zone, root and root tip.
Induction Screens
1. 100 μM KNO3 to 20 mM KNO3
24 Hrs.
No response observed after 24 Hrs. for line PT0863 treated under Low to High Nitrate (0.566 mM KNO3 to 30 mM KNO3) conditions.
48 Hrs.
An increased response in GFP level relative to control observed in roots of event 04 after 48 Hrs when line PT0863 treated under Low to High Nitrate (0.566 mM KNO3 to 30 mM KNO3) conditions.
2. Mature Plants - 0.566 mM KNO3 to 30 mM KNO3 - 48 Hrs
An increased response in GFP level relative to control is observed in roots of events 02 and 04 from line PT0863 treated under Low to High Nitrate (0.566 mM KNO3 to 30 mM KNO3) conditions.
Increase in GFP response observed in Epidermis (Ep) and Vascular (Vs) cells of roots from lines 02 and 04.
Quantitative PCR
Results: Tissues for QPCR were collected from stage 6.3-6.5 plants grown hydroponically.
Little to no nitrate-induced mRNA accumulation is observed at 6 hrs after nitrate induction except for event 4 in roots (the large values reported for 6 hour shoots could be due to very low levels of mRNA). All 4 events show nitrate induction of the endogenous At2g24280 and HAP1 gene but modest or no induction of GFP in roots. The data indicates that the promoter can drive nitrogen induced expression of the HAP1-VP16 gene.
Promoter utility
Trait Area: Nutrient
Sub-trait Area: Nitrogen utilization, Low nitrogen tolerance, Nitrogen use efficiency
Utility: Among other uses this promoter sequence could be useful to improve: nitrogen utilization by increasing the expression of nitrogen use efficiency genes in root and seed tissue in response to nitrogen fertilizer application. These genes can be in involved in processes that improve transport of nitrate, ammonium and amino acids and increase export of sucrose to sink tissues, thereby increasing plant vigor and yield. The promoter can also be used to express insecticidal, fungicidal and/or bactericidal proteins in order to prevent biotic root damage.

| | |
|---|---|
| Construct: | PT0863 |
| Promoter candidate I.D: | 15372139 |
| cDNA I.D: | 23494405 |
| Events expressing: | 01-04 |

Predicted promoter region was PCR amplified from the Columbia ecotype of *A. thaliana*. Promoter construct sequence is 5' verified in T1 mature plants and confirmed in the following generation by 5' and 3' sequencing of the entire promoter of two or 3 events. Sequences from all events are used to generate a consensus sequence.

```
                          Promoter sequence
>282.PT856.FPNUE predicted A (Ceres cDNA 12667371; SEQ ID NO:11)
aatgagctaaatcacaatagctccagcgaaaatgcatgattttaaaatgcttctttcaa
tgatatagttttattgtaatggaaaaatatttagcaaatagattataaacttacatgaga
caagtataaataattattataaacttattaagtttaagatcaaggcttttgtgcaatgta
tcaatgaatgttagatgtgatatgatgaaagcaatgttttaaacacatacatagtcattg
atcggaatgtgtgttattagaaatgcatgcctaagccgatagggttatctatgtttggtc
ttggacattatagccaaatttcgaatctaattcttccaatatatatttttttttttttgc
ttagggccactactagtattgcttatcaattttaagagctcatgaaaatgcaacaatata
gtagttgcaaatccttgtttcaagagaaatcaaagggccacttgtgaattgaataataat
aatatttgcaaataaccttccactaaaccataccaacaaaaccacacagatttggcaaag
acataacctttgggagacgtgaaaaggctcaaaatttgacaattgtccttacaaattcgc
```

-continued

Promoter sequence

```
tcattagtgcaattgtgagatttgtttgcatccaaatccaattcataactcacactcgtc
tcaaattcgaaaa

>282.PT856.FPNUE experimental (Ceres cDNA 23494405; SEQ ID NO:12)
gattataaacttacatgagacaagtataaataattattataaacttattaagtttaagatcaa
ggcttttgtgcaatgtatcaatgaatgttagatgtgatatgatgaaagcaatgttttaaacac
atacatagtcattgatcggaatgtgtgttattagaaatgcatgcctaagccgatagggttatc
tatgtttggtcttggacattatagccaaatttcgaatctaattcttccaatatatattttttt
ttttttgcttagggccactactagtattgcttatcaattttaagagctcatgaaaatgcaaca
atatagtagttgcaaatccttgtttcaagagaaatcaaagggccacttgtgaattgaataata
ataatatttgcaaataaccttcactaaaccataccaacaaaaccacacagatttggcaaaga
cataacctttgggagacgtgaaaaggctcaaaatttgacaattgtccttacaaattcgctcat
tagtgcaattgtgagatttgtttgcatccaaatccaattcataactcacactcgtctcaaatt
cgaaaa
```

Example 7

Promoter Expression Report #302.PT0886.FPNUE
Promoter Tested In: *Arabidopsis thaliana*, Wassilewskija (WS) ecotype
Spatial expression summary:
Hypocotyl      H epidermis H vascular
Cotyledon      H epidermis H mesophyll H vascular
Primary Root      H epidermis H cortex
Observed expression pattern:
T1 mature: No expression observed.
T2 seedling: High GFP expression in epidermis, mesophyll, and vasculature of cotyledons and in epidermis and vasculature in hypocotyl. High GFP expression in epidermis and cortex cells of roots.
Expected expression pattern:   Shoots - Nitrogen inducible (Low to High)
Selection Criteria:   Microarray data
Gene:   Ferredoxin-nitrite reductase, putative
GenBank: NM_127123 *Arabidopsis thaliana* ferredoxin-nitrite reductase, putative (At2g15620) mRNA, complete cds gi|30679484|ref|NM_127123.2|[30679484]
Source Promoter Organism:   *Arabidopsis thaliana*, Columbia (Col) ecotype
Vector:   pNewbin4-HAP1-GFP
Marker Type:   GFP-ER
Generation Screened:   X T1 Mature XT2 Seedling XT2 Mature   T3 Seedling
Treatment:   Age:   Gen:   Time points:   Events Screened/Response   Response:
0.566 mM KNO3   4 wks   T2   48 Hrs   4/2   Low
to 30 mM KNO3
T1 Mature Plant Expression   Organs/Tissues screened
Events Screened:   n = 3   Events Expressing:   n = 0
No GFP Expression Detected
T2 Seedling Expression   Tissues Screened
Events Screened: n = 6   Events Expressing: n = 5
GFP Expression Detected
X Hypocotyl   H epidermis cortex H vascular xylem phloem stomata
X Cotyledon   H epidermis H mesophyll H vascular margin stomata hydathode
Rosette Leaf   epidermis mesophyll vascular trichome petiole primordia stomata stipule margin hydathode
X Primary Root   H epidermis trichoblast atrichoblast H cortex endodermis vascular xylem phloem pericycle quiescent columella root cap root hairs
Lateral root   epidermis trichoblast atrichoblast cortex endodermis initials flanking cells vascular lateral root cap
Shoot apical meristem   Shoot apical meristem
Seedlings of line PT0886 at 7 days old show six events with detectable expression in the Epidermis (Ep), Cortex (Cr), Mesophyll (Me), Root (Rt).
Seedlings of line PT0886 at 14 days old show 4 seedlings for each of 6 events with GFP expression intensity highly variable in aerial organs.
Induction Screens
1. 0.566 mM KNO3 to 30 mM KNO3 (Low to High)
Increased GFP expression detected in roots of events 05 and 06 of plants transferred to 30 mM KN03 relative to mannitol control plants. Root (Rt) for 4 events of line PT0886
qRT-PCR
Results: Tissues for QPCR were collected from stage 6.3-6.5 plants grown hydroponically.
PT0886 lines -02, 05 and 06 showed strong induction of endogenous Fd-Nitrite reductase gene, Hap1 transgene and GFP transgene in shoots by 48 hrs after induction. PT0889-03 did not show -continued endogenous gene induction but did show Hap1 and GFP induced expression in 48 hr shoots. PT0866 events -02 and -03 showed induced expression at 6 hrs in both shoots and roots while events -05 and -06 did not or showed modest levels (-06). The data are largely consistent with the GP imaging results.
Promoter utility
Trait Area: Nutrient
Sub-trait Area: Nitrogen utilization, Low nitrogen tolerance, Nitrogen use efficiency
Utility: Among other uses this promoter sequence could be useful to improve: nitrogen utilization by increasing the expression of nitrogen use efficiency genes in vascular tissue in response to nitrogen fertilizer application. These genes can be in involved in processes that increase photosynthesis, improve transport of nitrate and amino acids and increase export of sucrose to sink tissues, thereby increasing plant vigor and yield.
Construct: PT0886
Promoter candidate I.D: 15372145
cDNA I.D: 23446949
Lines expressing: PT0886-03, 04, 05, 06 N-inducible GFP 05, 06

Predicted promoter region was PCR amplified from the Columbia ecotype of *A. thaliana*. Promoter construct sequence is 5' verified in T1 mature plants and confirmed in the following generation by 5' and 3' sequencing of the entire promoter of two or 3 events. Sequences from all events are used to generate a consensus sequence.

Promoter sequence (397 bp).

>302.PT0886 experimental (Ceres cDNA 12558510; SEQ ID NO:13)
agtgtatttgaaaacgacattgaagaattaatatatttttttttaattttagtttttat
agtacaaatattaaaacaaacaatcctaccatatcataacatttgtaaataacattttaa
gttttgttttgagttttaattaattttctatgacaaaaaaatgaagtcaatagactaagt
gaatcatatagtataaataaacacaatttaaatagtttcaaataaatttagaaagaataa
aacaaatagaaatcagaaggtgtctgtttcctcctcgcaacatacgatcaaagagaaaca
acttgacccttacattgctcaagagctcatctcttccctctacaaaaatggccgcacgt
ctccaaccttctcccaactccttcttccgccatcatc Example 8

Promoter Expression Report #275.PT0959.FPNUE
Promoter Tested In: *Arabidopsis thaliana*, Wassilewskija (WS) ecotype
Spatial expression summary:
Flower          L pedicel H sepal H abscission zone
Ovule           Post-fertilization: H Seed coat L embryo
Embryo          L cotyledons
Stem            L epidermis
Cotyledon       L epidermis L petiole
Observed expression pattern:
T1 Mature expression: High GFP expression at abscission zone of developing flowers and seed coats.
T2 Seedling expression: Low GFP expression in epidermis of cotyledons and petioles.
Expected expression pattern:    Nitrogen-Inducible in leaf (High to Low)
Selection Criteria:             Microarray
Gene:                           expressed protein
GenBank: NM_106662 *Arabidopsis thaliana* expressed protein (At1g80130)
Source Promoter Organism:       *Arabidopsis thaliana*, Columbia (Col) ecotype
Vector:                         pNewbin4-HAP1-GFP
Marker Type:                    GFP-ER
Generation Screened:    XT1 Mature XT2 Seedling  T2 Mature  T3 Seedling
Inductions completed.

| Treatment: | Age: | Gen: | Time points: | Events Screened/Response | Response: |
|---|---|---|---|---|---|
| 1. 14.3 mM KNO3 to 28.6 mM Mannitol | 4 wks | T2 | 72 hrs post transfer | 5/4 | Low |

Inducible expression summary:

| Treatment: | Time point induced: | Organs induced: | Tissues induced: |
|---|---|---|---|
| 1. 14.3 mM KNO3 to 28.6 mM Mannitol | 72 hrs post transfer | Flowers | Abscission zone, Sepals |
| | | Siliques | Epidermis |
| | | Ovules | Endosperm |

-continued

| | |
|---|---|
| T1 Mature Plant Expression | Organs/Tissues screened |
| Events Screened: n = 6 | Events Expressing: n = 6 |
| GFP Expression Detected | |
| X Flower | L pedicel receptacle nectary H sepal petal filament anther tapetum pollen carpel style papillae vascular epidermis stomata trichome |
| | silique H abscission zone |
| Silique | stigma style carpel septum placentae funiculus transmitting tissue vascular epidermis stomata abscission zone ovule |
| X Ovule | Pre-fertilization: primordia inner integument outer integument embryo sac funiculus chalaza micropyle gametophyte |
| | Post-fertilization: zygote suspensor embryo sack funiculus inner integument outer integument endothelium H seed coat primordia chalaza micropyle early endosperm mature endosperm embryo |
| X Embryo | suspensor preglobular globular heart torpedo late mature provascular hypophysis radicle L cotyledons root meristem shoot meristem |
| X Stem | L epidermis cortex interfascicular region vascular xylem phloem pith stomata trichome |
| Leaf | petiole mesophyll vascular epidermis trichome primordia stomata stipule margin |
| Shoot apical meristem | Shoot apical meristem Flower primordium |
| X in the Flower (Fl) and Silique (Si) | |
| X in the Abscission zone (Az) of the inflorescence meristem, the Stem, Cotyledon (Co) and Seed coat (Sc) | |
| T2 Seedling Expression | Tissues Screened |
| Events Screened: n = 5 | Events Expressing: n = 3 |
| GFP Expression Detected | |
| Hypocotyl | epidermis cortex vascular xylem phloem stomata |
| X Cotyledon | mesophyll vascular L epidermis margin L petiole stomata hydathode |
| Rosette Leaf | mesophyll vascular epidermis trichome petiole primordia stomata stipule margin hydathode |
| Primary Root | epidermis trichoblast atrichoblast cortex endodermis vascular xylem phloem pericycle quiescent columella root cap root hairs |
| Lateral root | epidermis trichoblast atrichoblast cortex endodermis initials primordia flanking cells vascular lateral root cap |
| Shoot apical meristem | Shoot apical meristem |

Induction Screens
1. 14.3 mM KNO3 to 28.6 mM Mannitol
Expression in the Silique (Si) of PT0959 event -02 under low nitrate conditions compared to control
Expression after 72 Hrs in the flower and flower buds, silique, ovules and carpels of PT0959 event -04 under low nitrate conditions compared to the control
qRT-PCR Data
Results: Tissues for QPCR were collected from stage 6.3-6.5 plants grown hydroponically as described in report "NE040615C_Nitrogen Promoter Report 12-29-2004". Event -02 shows the expected induction pattern of the endogenous gene in leaf tissue. The expression patterns of HAP1 and GFP in leaves are broadly similar to the endogenous gene in events -02 and -04 especially at the 72 hour time point, whereas event 3 shows no induced expression of HAP1 or GFP at 72 hours even though the endogenous gene shows induction. These data correlate well with the GFP imaging data above showing that the promoter construct drives GFP expression induced by nitrogen deficiency in events -02 and -04. See FIG. 5
Promoter utility
Trait Area: Nutrient
Sub-trait Area: Nitrogen utilization, Low nitrogen tolerance, Nitrogen use efficiency
Utility: Among other uses this promoter sequence could be useful to improve: nitrogen utilization by increasing the expression of nitrogen use efficiency genes in leaf and seed tissue in response to nitrogen deficiency. These genes could be in involved in processes that increase photosynthesis, improve transport of nitrate, ammonium and amino acids and increase export of sucrose to sink tissues, thereby increasing plant vigor and yield.

| | |
|---|---|
| Construct: | PT0959 |
| Promoter candidate I.D: | 22254782 |
| cDNA I.D: | 23546169 |
| Events expressing: | 02-04 |

Promoter sequence (1000 bp).

>PT0959 (Ceres cDNA 23546169; SEQ ID NO:14)
```
aagaccttttcgcaagtcatcaaagcacaatcccacaccgtacgttttggtttacctgtctgt
cagataacgaccgtctcaatatcggatcttaattacatttatgaataactcgactgcgcctcc
gcaaaataagaagaaattgaatatcgaacatttcaacctcaggcatcacatccaagtgattcc
ttatgttgatgtaaaaatgggatatataggaccaatcagattcatataataatattcataaat
cagattcgtaatgcagtatttatcagctccataaatgatcctagagaatcttatgtaaagtgg
atcatgcacgtatctttatcttctcaaaccttcgaaagaaaccctcaaaacgttattatctac
cgaatacatttaatccatatagcgtgacaaaagaacagagcccgtagttgataaaaagcatga
gagtgatgatgaatgtgaagcactgagagagatctcaccgcttgccgtataacgtctccgtct
ccgtctttgtcggcattcgtcagctgaactcttaaacgtgtcgactgttgtctcgatccaaga
taacactgtagctgacagttacatttagagtttgtctccatctcatgcgcaacgcagcaccgt
caattttctgtgaggatactaaactactatgtaatgatgtcgacaaaagagtgaaaggtgggt
cccgcatttgcccatgtggttatggtcaacgtgtcaaagtactagcggctgtgttttaatccg
atcttttttctatcaatccatggtcccgtagaataatttcactattttttcacttggctggtgt
caacttagagaccaataatatatacacttatcttttacagtctaaatttaattatgcggctta
ccattatataagactctggtagactactctcattatatacattataaagatactgatgagtgg
ttcttgtttaatggagtttaaatttaaaaatatttggtaaccgagtggatcatc
```

Example 9

| | |
|---|---|
| Report # | NE040615C Nitrogen Inducible Promoters. |
| Trait area | Nitrogen Use Efficiency |
| Subtract Area | Low Nitrogen Tolerance |
| Promoter Sequences | Promoters corresponding to the following genes; putative monodehydroascorbate Reductase (At1g63940), fibrillarin-2 (At4g25630),. |
| Comments | This report describes the promoters selected for nitrogen inducible gene expression. |

Materials and Methods:

Gene expression that is consistently induced by low-to-high nitrogen treatment is used as the primary selection criterion to obtain promoter candidates. In short, *Arabidopsis thaliana* (ecotype Wassilewskija) seeds are sown on flats containing 4 L of a 1:2 mixture of Grace Zonolite vermiculite and soil. Flats are watered with 3 L of water and vernalized at 4° C. for five days. Flats are placed in a Conviron growth chamber having 16 hr light/8 hr dark at 20° C., 80% humidity and 17,450 LUX. Flats are watered with approximately 1.5 L of water every four days. Mature, bolting plants (24 days after germination) are bottom treated with 2 L of either a control (100 mM mannitol pH 5.5) or an experimental (50 mM ammonium nitrate, pH 5.5) solution. Roots, leaves and siliques are harvested separately 30, 120 and 240 minutes after treatment, flash frozen in liquid nitrogen and stored at $-80°$ C.

Hybrid maize seed (Pioneer hybrid 35A19) are aerated overnight in deionized water. Thirty seeds are plated in each flat, which contained 4 liters of Grace zonolite vermiculite. Two liters of water are bottom fed and flats were kept in a Conviron growth chamber with 16 hr light/8 hr dark at 20° C. and 80% humidity. Flats are watered with 1 L of tap water every three days. Five day old seedlings are treated as described above with 2 L of either a control (100 mM mannitol pH 6.5) solution or 1 L of an experimental (50 mM ammonium nitrate, pH 6.8) solution. Fifteen shoots per time point per treatment are harvested 10, 90 and 180 minutes after treatment, flash frozen in liquid nitrogen and stored at $-80°$ C.

Alternatively, seeds of *Arabidopsis thaliana* (ecotype Wassilewskija) are left at 4° C. for 3 days to vernalize. They are then sown on vermiculite in a growth chamber having 16 hours light/8 hours dark, 12,000-14,000 LUX, 70% humidity, and 20° C. They are bottom-watered with tap water, twice weekly. Twenty-four days old plants are sprayed with either $_2$water (control) or 0.6% ammonium nitrate at 4 μL/cm$^2$ of tray surface. Total shoots and some primary roots are cleaned of vermiculite, flash-frozen in liquid nitrogen and stored at $-80°$ C.

Any method of quantization of expression in the treated samples versus controls, such as microarray analysis can be used. Those genes showing increased expression under treatment conditions as compared to controls are identified as having candidate nitrogen-inducible promoters.

Quantitative PCR Validation of Nitrogen Inducible Gene Expression.

Expression profiles of the selected genes were verified by qRT-PCR with RNA samples. In addition, plants were cultivated hydroponically and submitted to low-to-high nitrate treatment. Plants were cultivated in a modified Hoagland's solution containing 15 ppm of nitrogen as KNO3 (1.7 mM KNO3) as the sole nitrogen (N) source. Plants were grown in a walk-in Conviron growth chamber under long day light cycle until they developed siliques and then transferred to 0.0 ppm N media for 3 days to adapt them to low nitrogen conditions. Nitrate induction was carried out by transferring experimental plants to 200 ppm of N (14.3 mM KNO3) and controls to 28.6 mM mannitol. Root and rosette tissue from experimental and control plants (2 plants each) were harvested at 0.25, 1, 2, 4, 6 and 24 hours after treatment.

Analysis of Nitrate-Inducible Promoter:GFP Fusions and Two-Component Reporter Gene Constructs.

The promoter regions of five selected nitrate-inducible genes include 1000 bp upstream of the first nucleotide 5' to the predicted ATG of the open reading frame. The promoter regions were shortened if a neighboring CDS overlapped the upstream 1000 bp (Table 1). The sequences of the promoter regions are listened below. Primers including the restriction site BstX1 were designed to isolate these promoters by PCR (Table 2). The products were directly fused to mGFP5-ER in the vector Newbin4-35S-GFP. The selected promoters were also cloned into the two-component vector CRS815, upstream of VP16-HAP1. Transgenic T1 plants generated with these constructs were cultivated on soil and analyzed for expression of GFP in all aerial tissues under normal growth conditions.

Nitrogen-induced expression was analyzed in T2 generation plants. Seeds of each line were germinated on vertical MS minus N plates. Nitrogen induction was performed on seven days old seedlings by adding 3 ml/plate of 60 mM KNO$_3$ and Control plates were treated with 120 mM mannitol. GFP expression was visualized with Confocal laser scanning microscopy 6 and 24 hours after induction. In some cases, the induction time was extended to 48 hours.

TABLE 1

Nitrogen induced promoter candidates selected for GFP fusion and 2 component expression analyses constructs.

| Locus ID | CDNA_ID | Gene Name | ANNOT_ID | Promoter pipeline_ID | PFAM_DESC | Genbank NR-DB Description |
|---|---|---|---|---|---|---|
| 5847 | 12577385 | At1g63940 | 520887 | 15372142 | Pyridine nucleotide-disulphide oxidoreductase | putative monodehydroascorbate Reductase |
| 21911 | 13497685 | At4g25630 | 566416 | 15372151 | Fibrillarin | Fibrillarin |

TABLE 2

Oligonucleotides used for cloning into Newbin4-35S-GFP direct fusion construct.

| Gene Name | Promoter ID | Size (bp) | Oligos for cloning into CRS815 oligo 5' sequence | oligo 3' sequence | Oligos for cloning into Newbin4-35S-GFP oligo 5' sequence | oligo 3' sequence |
|---|---|---|---|---|---|---|
| At1g63940 | 15372142 | 921 | (SEQ ID NO:18) TTCACCAGTCG ATTGGCCCGAT CGGCCaaagttttg aattattggga | (SEQ ID NO:19) CATGCCATTG CACTGGCCCT GCAGGCCtagttt ataagaagagccaa | (SEQ ID NO:20) CCGGCGCCAG TCGATTGGGT TTTGTAATTCT TTGGGGG | (SEQ ID NO:21) CGCGCGCCAG TGCAATGGGA CTCTACGAAC TGTAACAA |
| At4g25630 | 15372151 | 1000 | (SEQ ID NO:22) TTCACCAGTCG ATTGGCCCGAT CGGCCaaaaagg atgggtaatggga | (SEQ ID NO:23) CATGCCATTG CACTGGCCCT GCAGGCCctttg cgttaagactctaaa | (SEQ ID NO:24) CCGGCGCCAG TCGATTGGAA AAAGGATGGG TAATGGGA | (SEQ ID NO:25) CGCGCGCCAG TGCAATGGCT TTGCGTTAAG ACTCTAAA |

Analysis of Nitrate Induced Promoters

Further analysis of GFP expression was carried out on mature plants cultivated in similar hydroponic conditions as described above. Nitrate induction was done by transferring plants to Hoagland's solution supplemented with 30 mM KNO3. Plants were analyzed for GFP expression after 24, 48 and 72 hours of induction. Shoot and root tissues were collected for QRT-PCR analysis. A modification of this procedure was also implemented in order to avoid the adaptation period at 0.0 N. In this case, plants were cultivated in Hoagland's solution supplemented with 5 ppm N (600 μM KNO3) and then transferred to media containing 30 mM KNO3. All experimental and control plants were genotyped for the presence of the promoter construct.

Promoter Sequences of Nitrogen Inducible Promoter Candidates. The ATG of predicted full length protein coding sequence occurs immediately downstream of the 3' nucleotide.

```
15372142-At1g63940 predicted (Ceres cDNA_12577385; SEQ ID NO:15)
gttttgtaattctttgggggctaataggatattttattttcttggtttcgtctattgttgtttttctatttatggttgggcttttagaactctggaca
ggcccatgtcatatgttttcccttctccttatattttcattttcattttgttaaattaatgcataatatccaaaaacaatttaaattttgaagg
aaccctttagttacggctccgaagcttttcacaagtgagaatgtgagatcaaagaaggcaaatggaggattttaaaagttaaaatcatc
ttttatctgcaaaagttgacaattttttttgtatcaaatctaaatcatcaaactctcttaaactacaagagcataacaacctctatgtaatcca
tgaaataatctgcttgaaggacataacataatcattatggctagagtgactaacttcaatcaaatcctcttaactctagctcccttacaa
tggtatcgtaaaacattatgcattagggattgttgtcctaggaaaataaaataaaaatccccacagaccaactaccattttaacttaaaa
ataagcttcgtccgcgacgaattgttttccatcctaaaaatagaatggtgtaatctgctaatggtttagttccattaacttgcaagttctatt
gaaagcctaaatgtcaataaagatattaaaattcggagtcaaagacaaatgaatcaaaagcaacaagacaagtcagctccagcagtcgcatgcgtccatccagtgc
cactacccatcttttacaataaatcatctctcttttcacaaatttcaaactactctcattgcccttagctttgttatagagccaacactacag
agagactcacacacttgtttcaataattaaatctgaatttggctcttcttataaactaatgtctgcaggtcttcttatctctctcactcacca
ccatcttcttcctcgattgtcaaaacccctagatcgaaatcttatctctctaatctgttgttacagttcgtagagtc 15372142-At1g63940 experimental (Ceres cDNA 13611030; SEQ ID NO:16)
5'aaagttttgaattattgggaatcaatttcgaagttttgtaattctttgggggctaataggatattttattttcttggtttcgtctattgttgttt
ttctatttatggttgggcttttagaactctggacaggcccatgtcatatgttttcccttctccttatattttcattttcattttgttaaattaatg
cataatatccaaaaacaatttaaattttgaaggaaccctttagttacggctccgaagctttcacaagtgagaatgtgagatcaaagaa
ggcaaatggaggattttaaaagttaaaatcatcttttatctgcaaaagttgacaattttttttgtatcaaatctaaatcatcaaactctcttaa
actacaagagcataacaacctctatgtaatccatgaaataatctgcttgaaggacataacataatcattatggctagagtgactaact
tcaatcaaatcctcttaactctagctcccttacaatggtatcgtaaaacattatgcattagggattgttgtcctaggaaaataaaataaaa
atccccacagaccaactaccattttaacttaaaaataagcttcgtccgcgacgaattgttttccatcctaaaaatagaatggtgtaatct
gctaatggtttagttccattaacttgcaagttctattgaaagcctaaatgtcaataaagatattaaaattcggagtcaaagacaaatga
atcaaaagcaacaagacaagtcagctccattcttcactacccatcttttacaataaatcatctctcttttcacaaatttcaaactactctca
ttgcccttagctttgttatagagccaacactacagagagactcacacacttgtttcaataattaaatctgaatttggctcttcttataaact
```

-continued a3'

15372151-At4g25630 (Cers cDNA 13497685; SEQ ID NO:17)
```
5'aaaaaggatgggtaatgggacctattttccccaacatcccacatgcacacttccctctccattctctcacatttatttctttcattctaat
ttatccattccgtgtgtaacatattcactaataatctcatctcactaactcattcattgattgtgatatgttttatctagaattagtgttttaacac
tgtgtctacatatgatttcctttcattgtatgtgaacatgttaactcactaatcattttgtattttcgagttaacatgagtctccacttcggta
gactaaagtaaagataggtttgagtataataaagtttaaaatttgctttaaaatcaatatttataaataagttttatcataagtgatttttgta
tgttatattggaccttgtataaacagactacagaagaaatttatgagaacttgtaatgttagagtggacctcgtataaactaattatg
tgggcttttaccataaactatttatgaaaattattatggcccacaccactataactaaagcccacatatttagcagcccagtttcattgta
agagacatgttcgctctggaactagaattttctggtttttgggtatttgttttcttatgtgtagagaaatgatggtaacgattaaatgttgtgt
attacaatttacaatggtaagacgattaatatatttacacacaattttgttgttgctgtaacacgttagtgtgtgtgatgatagaatttcata
aagctttaactacgaggggcaaaatgttaattctaaatagttgacagcagaaaaagatatgtatacataatataaggattaaaacgtaa
ataataataaaggcgagttaaattaaaaccctgttaaaaccctagcttgaaacacatgtataaaaacacttgcgagcgcagcttc
atcgccatcgccattctctctctcatcaaaagcttttctccttgattttcgcattctttagagtcttaacgcaaag3'
```

Results:

Gene expression that was consistently induced by low-to-high nitrogen treatment was used as the primary selection criterion to obtain promoter candidates. Selections with consistent expression profiles in replicate and across several experiments in either roots, leaves or siliques were made for independent experiments and then cross-referenced to other expression profile experiments in order to select against genes with highly variable expression patterns across several experiments.

qRT-PCR Analysis of 5 Putative Nitrogen Inducible Genes:

To verify the expression patterns of the selected genes, qRT-PCR was carried out with shoot RNA samples. FIGS. 6A and 6B shows the differential expression ratios obtained with qRT-PCR and the ratios obtained with the corresponding RNA samples used in the microarray experiment. The trend of induction is similar between the two data sets for most time points while the magnitude of response is sometimes much higher or lower in the qRT-PCR data.

Figure 7:
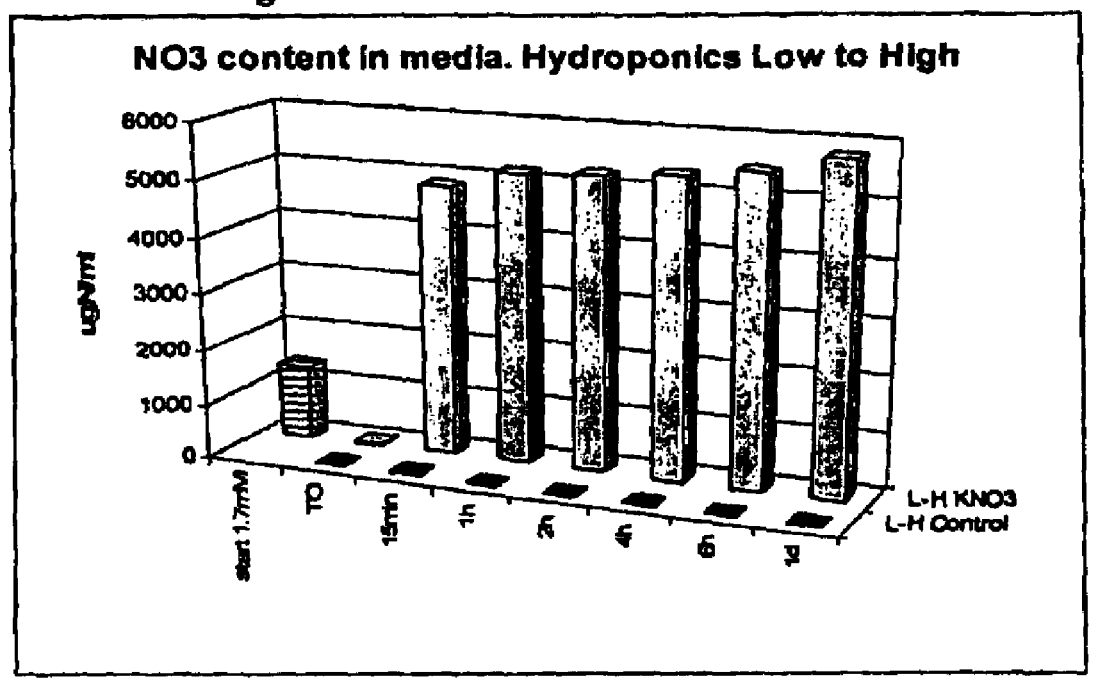

In order to examine expression of the candidate promoters over longer induction times and to analyze expression in roots and shoots we carried out an extended nitrogen induction experiment in hydroponic conditions. The nitrogen content in the growth media of experimental and control plants was monitored during treatment as shown in FIG. 7. The results of differential expression ratios determined by qRT-PCR in roots and shoots are shown in FIGS. 8A and 8B. Expression in both shoots and roots was observed for all genes including the nitrate transporter gene At1g08100, which was originally selected for root specific expression from the Wang et al. 2003 TxP data set. The expression of At1g08100 in both shoots and roots is consistent with data reported by Okamoto et al., 2003. The monodehydroascorbate reductase gene shows similar high levels of induction in both shoots and roots. Overall, the data show that both of the selected genes are nitrogen-inducible.

T1 Generation GFP Expression Analysis of Two-Component:GFP Transgenic Plants:

GFP expression data was obtained for the fibrillarin-2 (At4g25630) two-component promoter construct under normal growth conditions. GFP expression for the fibrillarin-2 promoter construct was observed in only one out of 3 independent lines tested. The fibrillarin-2 (At4g25630) promoter drives GFP expression the inflorescence stem and a number of floral tissues. Moderate levels of expression are seen in sepals, petals, style and in the valve margins. No expression was observed in stamens, immature ovules or leaves. The fibrillarin-2 (At4g25630) promoter in the direct fusion construct shows a comparable expression pattern to the Two-component construct, however much weaker.

TABLE 3

Updated results of GFP expression in T1 transgenic plants derived from constructs of promoter candidates in two-component and direct fusion constructs.

| | STATUS - Direct fusion lines | Locus ID | CDNA ID | Gene Name | ANNOT ID | METHOD | Promoter pipeline ID | T1 Lines tested | T1 Lines expressing |
|---|---|---|---|---|---|---|---|---|---|
| | Nitrogen promoters for construction of direct-GFP fusion constructs | | | | | | | | |
| SR01690 | T1mature screened | 21911 | 13497685 | At4g25630 | 566416 | OCDS | 15372151 | 8 | 1 |
| | STATUS-Two component lines | | | | | | | | |
| PT0829 | T1 scheduled: 3 weeks old | 5847 | 12577385 | At1g63940 | 520887 | OCDNA | 15372142 | 6 | 0 |
| PT0665 | T1 Mature screened | 21911 | 13497685 | At4g25630 | 566416 | OCDS | 15372151 | 4 | 1 |

T2 Generation GFP Expression Analysis of Transgenic Plants Treated with KNO3.

Seedlings of T2 lines from direct promoter:GFP fusion and two-component:GFP constructs were analyzed under nitrate inducing conditions. Lines of the 2-component:GFP fusion constructs of Fibrillarin-2 (At4g25630) and the monodehydroascorbate reductase gene (At1g63940) promoters showed inducible GFP expression. Strong induction of the pyridine nucleotide-disulfide oxidoreductase promoter was observed in roots and at a significant level in cotyledons. Expression of this promoter increased in time, being more intense after 48 hours of induction. The fibrillarin-2 promoter showed strong induction in cotyledons, including hypocotyls and pedicel. Induction was also significant in emerging rosette leaves and lateral roots. The promoter showed stronger expression at 6 hours of induction with a noticeable decrease after 24 hours. None of the transgenic plants from direct promoter:GFP fusions showed detectable induction.

Expression Analysis of Mature Plants Treated with $KNO_3$

Mature transgenic plants carrying either a direct fusion promoter:GFP or two-component:GFP construct were analyzed in hydroponic culture for expression of GFP in nitrate inducing conditions. In the first experiment, plants cultivated in 15 ppm nitrate, adapted to 0 ppm nitrate for 3 days followed by induction with 200 ppm nitrate. Under these conditions, one event of a Fibrillarin-2 promoter—two-component construct, PT0665-01, showed nitrate induction in roots at 24 and 48 hours, however, in floral tissue the expression seems to decrease in induced plants. The other event for the Fibrillarin-2 2componenet construct tested, PT0665-02, showed expression in root tips, but no detectable induction. Two events of the two-component construct of the monodehydroascorbate reductase promoter, PT0829-04 and PT0829-05, showed weak induction of GFP expression in root vascular tissue after 48 and 72 hours of nitrate induction. No GFP expression was observed in aerial tissue of these lines. A line of monodehydroascorbate reductase promoter fused directly to GFP, SR01688-01, showed induction of expression in root vascular tissue at 48 hours. The rest of the lines tested showed no detectable GFP expression in control or experimental plants.

To study the induction of Fibrillarin-2 and monodehydroascorbate reductase gene promoters at a molecular level, RNA from root and shoot tissues were analyzed by QRT-PCR. We analyzed the expression of GFP, HAP1-VP16 and the corresponding endogenous genes (At1g63940 or At4g25630). The results reflect the GFP expression observed by fluorescence microscopy. For example, QRT-PCR of GFP and the endogenous gene in the two lines of the monodehydroascorbate reductase promoter (At1g63940) showed stronger induction in roots than in shoots. In these lines, we detected GFP expression only in roots. In the case of Fibrillarin-2, stronger expression was obtained in shoots. Interestingly, with the exception of Fibrillarin-2 in shoots, the activity of the endogenous promoters and the isolated promoters followed the same trend. The activity of monodehydroascorbate reductase promoter was reduced significantly in the line PT0829-04 from 24 to 48 hours. In roots of PT0829-05, reduction of expression was significant after 72 hours. The Fibrillarin-2 line showed similar behavior in roots, however the activity of the promoter was stimulated in shoots.

The hydroponic conditions used in the experiment described above proved useful to test the inducibility of the promoters. However, during the procedure, before nitrate induction, the plants undergo an adaptation period from relatively high nitrogen to no nitrogen conditions. This step might introduce unpredicted responses of the promoters, which could obscure the nitrate induction response. To bypass the adaptation period, we modified the procedure by cultivation the plants under constant low nitrogen before induction with nitrate. The lines PT0665-01 (fibrillarin-2, At4g25630) and PT0829-05 (monodehydroascorbate reductase, At1g63940) were tested under these new conditions. We observed strong expression of GFP in pedicels of nitrate induced plants of line PT0665-01 after 24 hours. The GFP expression was more pronounced in pedicels after 48 hours of induction and significant induction was evident in root tips and the valve margins. Similar GFP expression patterns in aerial tissue were observed in PT0665 T1 generation plants cultivated on soil. The line PT0829-05 showed clear induction of GFP expression in roots. No expression was observed in any other tissue.

Discussion

Nitrogen is most frequently the rate limiting mineral nutrient for crop production. Plants have evolved complex signaling and regulatory mechanisms to enable rapid physiological and metabolic response to changes in the supply of inorganic nitrogen in the soil. Part of this regulation is achieved through transcriptional regulation of gene expression. This is an important mechanism for allowing plants to adjust nitrogen uptake, reduction and transport in response to changing environmental conditions. Inefficiencies in nitrogen use efficiency may be overcome through the use of nitrogen regulated gene expression to modify the response of rate limiting enzymes and metabolic pathways to changes in nitrogen availability.

We selected nitrogen-induced genes in which nitrogen-induced gene expression is triggered in nitrogen-starved plants after supply with either nitrate alone or with ammonium nitrate. One selected gene, monodehydroascorbate reductase, functions in processes related to nitrate signaling, transport, assimilation, and energy production. The other gene, fibrillarin-2, does not have a well-defined role in nitrogen metabolism. These genes were selected for GFP analysis in direct fusion vectors and in VP16-HAP1 two-component system as well as for cloning into VP16-HAP1 2-component GFP constructs and characterization in transgenic *Arabidopsis* plants. We verified the expression patterns observed for these genes using qRT-PCR with the same RNA samples used for a microarray hybridization. All of the genes showed similar trends to the transcription expression profiling data set. The expression of the genes was further characterized in roots and shoots of hydroponically grown plants using qRT-PCR.

The genes exhibit nitrate inducible expression in both roots and shoots. The highest and most sustained level of expression was observed for At1g63940 which encodes a monodehydroascorbate reductase coding sequence. Overall the results suggest that all both genes selected for promoter analysis are nitrate inducible with different temporal patterns of nitrate induced expression.

Analysis of the promoters in the 2-component vector system indicates that two promoters are expressed to some degree under standard growth conditions containing sufficient nitrogen levels for normal plant growth. The monodehydroascorbate reductase promoter showed increasing expression of GFP after induction. Strong GFP expression was detected in roots and cotyledons. These expression patterns are in good agreement with the expression profile obtained in transcription expression profiling and qRT-PCR experiments for the corresponding gene. The fibrillarin-2 promoter was observed to drive GFP expression in a number of floral tissues and the stem under regular conditions. This promoter is also inducible by nitrate. Strong expression of GFP was observed in lateral roots and in most of the green tissue. The expression activity of the promoter seems to decrease after 24 hours of induction. To some extent this behavior does not reflects the expression pattern showed by the fibrillin-2 gene in transcription expression profiling and qRT-PCR experiments, where expression is sustained after 24 hours.

The monodehydroascorbate reductase and fibrillin-2 promoters fused directly to GFP did not show a significant increase in expression of GFP under nitrate inducing conditions on plates. Similar results were obtained in hydroponic conditions for direct promoter:GFP fusions. Only one line of the direct fusion monodehydroascorbate reductase (At1g63940) promoter:GFP showed detectable induction. It is possible that, under these inducing conditions, the promoters are not sufficiently strong to stimulate expression of detectable levels of GFP, or that additional transgenic events need to be examined to select for stronger expression. Nitrate induction analysis of the lines in hydroponics revealed that the Fibrillarin-2 and the monodehydroascorbate reductase promoters are inducible by nitrate. A clearer response was observed under modified inducing conditions. The GFP expression patterns observed, and gene expression determined by QRT-PCR, indicated that the fibrillarin-2 promoter is preferably induced in shoots (mostly in reproductive tissue), while the monodehydroascorbate reductase promoter is induced in roots.

Applicability of Promoters to Corn and Other Species

The fibrilliarin-2 promoter will be useful for driving expression in flowers especially pedicels and silique vasculature and may be useful for increasing nutrient transport and/or utilization in reproductive organs. The monodehydroascorbate reductase promoter will be useful driving nitrate inducible expression in roots.

REFERENCES

Forde, B. G. (2002). LOCAL AND LONG-RANGE SIGNALING PATHWAYS REGULATING PLANT RESPONSES TO NITRATE. Annual Review of Plant Biology 53, 203-224.

Gazzarrini, S., Lejay, L., Gojon, A., Ninnemann, O., Frommer, W. B., and von Wiren, N. (1999). Three Functional Transporters for Constitutive, Diurnally Regulated, and Starvation-Induced Uptake of Ammonium into *Arabidopsis* Roots. Plant Cell 11, 937-948.

Glass, A. D. M., Britto, D. T., Kaiser, B. N., Kinghorn, J. R., Kronzucker, H. J., Kumar, A., Okamoto, M., Rawat, S., Siddiqi, M. Y., Unkles, S. E., and Vidmar, J. J. (2002). The regulation of nitrate and ammonium transport systems in plants. J. Exp. Bot. 53, 855-864.

Huber, J. L., Redinbaugh, M. G., Huber, S. C., and Campbell, W. H. (1994). Regulation of Maize Leaf Nitrate Reductase Activity Involves Both Gene Expression and Protein Phosphorylation. Plant Physiol 106, 1667-1674.

Hwang, C. F., Lin, Y., D'Souza, T., and Cheng, C. L. (1997). Sequences Necessary for Nitrate-Dependent Transcription of *Arabidopsis* Nitrate Reductase Genes. Plant Physiol. 113, 853-862.

Lin, Y., Hwang, C. F., Brown, J. B., and Cheng, C. L. (1994). 5[prime] Proximal Regions of *Arabidopsis* Nitrate Reductase Genes Direct Nitrate-Induced Transcription in Transgenic Tobacco. Plant Physiol. 106, 477-484.

Okamoto, M., Vidmar, J. J., and Glass, A. D. M. (2003). Regulation of NRT1 and NRT2 Gene Families of *Arabidopsis thaliana*: Responses to Nitrate Provision. Plant Cell Physiol. 44, 304-317.

Rastogi, R., Back, E., Schneiderbauer, A., Bowsher, C. G., Moffatt, B., and Rothstein, S. J. (1993). A 330 bp region of the spinach nitrite reductase gene promoter directs nitrate-inducible tissue-specific expression in transgenic tobacco. Plant J 4, 317-326.

Redinbaugh, M. G., and Campbell, W. H. (1991). Higher plant responses to environmental nitrate. Physiol. Plant. 82, 640-650.

Redinbaugh, M. G., and Campbell, W. H. (1998). Nitrate regulation of the oxidative pentose phosphate pathway in maize (*Zea mays* L.) root plastids: induction of 6-phosphogluconate dehydrogenase activity, protein and transcript levels. Plant Science 134, 129-140.

Wang, R., Guegler, K., LaBrie, S. T., and Crawford, N. M. (2000). Genomic Analysis of a Nutrient Response in *Arabidopsis* Reveals Diverse Expression Patterns and Novel Metabolic and Potential Regulatory Genes Induced by Nitrate. Plant Cell 12, 1491-1510.

Wang, R., Okamoto, M., Xing, X., and Crawford, N. M. (2003). Microarray Analysis of the Nitrate Response in *Arabidopsis* Roots and Shoots Reveals over 1,000 Rapidly Responding Genes and New Linkages to Glucose, Trehalose-6-Phosphate, Iron, and Sulfate Metabolism. Plant Physiol. 132, 556-567.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

TABLE 1

| REPORT NO. | ENDOGENOUS cDNA | OPTIONAL PROMOTER FRAGMENTS |
| --- | --- | --- |
| 174 | 12663481 | 908-967 |
| 199 | 13497685 | 895-954 |
| 282 | 12667371 | 624-673 |
| 207 | 12577385 | 858-899 |
| 302 | 12558510 | 373-397 |
| 182 | 12574427 | 885-1000 |
| 169 | 12340498 | 1-277 |
|  |  | 278-345 |
| 170 | 13610771 | 864-1000 |
| 166 | 13492462 | 879-998 |

What is claimed is:

1. A vector construct comprising: a) a nitrogen responsive promoter that directs transcription comprising a first nucleic acid molecule having the sequence of SEQ ID NO: 2; and b) a second nucleic acid molecule having to be transcribed, wherein said first and second nucleic acid molecules are heterologous to each other and are operatively linked together.

2. A host cell comprising the vector construct of claim 1.

3. A plant comprising the vector construct according to claim 1.

4. A method of introducing a vector construct into a host cell comprising: a) providing the vector construct according to claim 3; and b) contacting said vector construct with said host cell under conditions that permit insertion of said vector construct into said host cell.

5. A method of transforming a plant cell comprising transforming a host cell with the vector construct according to claim 3.

6. A plant, plant cell, plant material or seed of a plant which comprises the vector construct according to claim 1, wherein said seed comprises said vector construct.

7. A plant that has been regenerated from the plant cell or seed according to claim 6.

* * * * *

SEQUENCE LISTING

<160> NUMBER OF SEQ ID NOS: 25

<210> SEQ ID NO 1
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 13492462

<400> SEQUENCE: 1

```
ttaaccctaa acaaaacaat ctcattggtt tcataaataa attgtttaca aagtatacgt      60
actgcatgaa cgaatgaacc atatctatat ttataaaact catagagacc aatagtttaa     120
gagaggcact tatatagctc aacaaataat agcgaactag agagaatatg atctaattag     180
ttataaatct caattttgaa attgaagtgc gttatttcat ttgagaatct atgtgttttt     240
tttgttgttg ttagatgaga agctaggttt ttttcttttc tttacaccga taatcgataa     300
tatatgttaa tcacactgat ttttgtttga gacatgaaga ttcgaaaaat ttgtcaacga     360
ataaacactg gatagataga attgagatct gccatcaaat aatcgagatc gttcatgcat     420
gacgcaaaca tttatataga aatgaagcaa gtaaagaata tgaaaaagaa tagaaatgag     480
aaatttataa agaaagaaaa aaagaaccaa tggttgagga ggcaactatt cgcggggaca     540
cggagccgtt cgcacccatc accttggaat ctctcttttct tcctctctcc tcatcaccaa    600
ctagtcaaca accacacacc attttttaact ttcataatta aacctaacat aacatttttt    660
tttgtataaa ctatagcata aattaaattc agtaatgat aaaataaata tattttgtag     720
caatcattct attttgtaat ttggtagggc tctttaaact ttgattatta tccaattttt     780
attaaaatat aataaaatct caaagccatg acccattcct tcactcaagt atcaatgtct     840
attgtctata aatattacat aactcttctt cttcaaccaa acattgaaac actttgtccc     900
actctctctc tttctctttc ttgtaccaaa agcttttga atctccaaga ttatagcaaa      960
accaaagata aatactaac ttaaaagatt tctgaaaata                           1000
```

<210> SEQ ID NO 2
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 23643047

<400> SEQUENCE: 2

```
gtaggcaaaa aaacgcctct atctttcttc taaaacattt ttcatattaa attatcaaaa     60
cccttaaggt tgatttaagg gtcaggtagt ggatttgttt cgttgaaggg tcagcttagc    120
cttaaccctaa acaaaacaa tctcattggt ttcataaata aattgtttac aaagtatacg    180
tactgcatga acgaatgaac catatctata tttataaaac tcatagagac caatagttta    240
agagaggcac ttatatagct caacaaataa tagcgaacta gagagaatat gatctaatta    300
gttataaatc tcaattttga aattgaagtg cgttatttca tttgagaatc tatgtgtttt    360
ttttgttgtt gttagatgag aagctaggtt ttttcttttt ctttacaccg ataatcgata    420
atatatgtta atcacactga ttttgtttg agacatgaag attcgaaaaa tttgtcaacg    480
aataaacact ggatagatag aattgagatc tgccatcaaa taatcgagat cgttcatgca    540
```

```
tgacgcaaac atttatatag aaatgaagca agtaaagaat atgaaaagaa atagaaatga      600
gaaatttata aagaaagaaa aaaagaacca atggttgagg aggcaactat tcgcggggac      660
acggagccgt tcgcacccat caccttggaa tctctctttc ttcctctctc ctcatcacca      720
actagtcaac aaccacacac cattttaac tttcataatt aaacctaaca taacatttt       780 ttttgtataa actatagcat aaattaaatt cagttaatga taaaataaat atattttgta      840
gcaatcattc tattttgtaa tttggtaggg ctctttaaac tttgattatt atccaatttt      900
tattaaaata taataaaatc tcaaagccat gacccattcc ttcactcaag tatcaatgtc      960
tattgtctat aaatattaca taactcttct tcttcaacca                          1000

<210> SEQ ID NO 3
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 12340498

<400> SEQUENCE: 3
aactatattt atatccgatt tcattttcgc gaaacgagaa aatccaatga aaaattaact      60
caagaaaaaa aaaagttacg aaaacatttt atttgtaatt aaatgaatca tatataaaat     120
caaaaacagc agaataatgg aaacaaataa tctggtagga aaaataatca aataattaag     180
acgtctcagg tgacacaagt tgggccgtca cggccttcca aaagccacac tgctctctcc     240
ttttatatat tttgcttcca cctctcaaga ctcctccacc aacccctct cgcactctcc      300 gccaccttct tccctaattc tctctctctc gctacctctc tacgtaagtt tcagatttga    360
ctttattagc ttcgattctc tctgatattt gtttctagaa tttgatctga tcagcgatgt     420
ttacttgttc cttgtttttt gttttttcat tgacttcttg tggggacaaa aaaaaacaat     480
caaatatctt tcgatttcgt tgttcttctc ttttcgtta tctgatagtg accgatttga    540
tcctgtatcg ttgctattca gatgctaatc atctccttaa ttgtgaattt ttttgttgtt     600
atttagtgaa tcttgttaca agtctgttgt aggtttattt ttgccattaa gctactttga     660
tcgactttag aatctatttg atgataagta attaaacatg ttttagtgat tgttaagtaa     720
gtcatttagt catgtttttg gagcatcgag tgaagatcta atatagcttt aagcttgcat     780
cttctcatta cgctccatac actaattttc acatcatatt tgctattgga aacagataag     840
tttttggttc ttgtttccat tgctacttgt gatgcacatc ctcacaattt tctctcagtt     900
ttggttctta tttctctgga acagtttgat ttgttagatt gtatcactat gaagaaaccc     960
tgaagctaaa cttgtttata aacgcaggtg ataaacaaga                          1000

<210> SEQ ID NO 4
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 23373586

<400> SEQUENCE: 4
aactatattt atatccgatt tcattttcgc gaaacgagaa aatccaatga aaaattaact      60
caagaaaaaa aaaagttacg aaaacatttt atttgtaatt aaatgaatca tatataaaat     120
```

-continued

```
caaaaacagc agaataatgg aaacaaataa tctggtagga aaataatca aataattaag    180
acgtctcagg tgacacaagt tgggccgtca cggccttcca aaagccacac tgctctctcc   240
ttttatatat tttgcttcca cctctcaaga ctcctccacc aaccccctct cgcactctcc   300
gccaccttct tccctaattc tctctctctc gctacctctc tacgtaagtt tcagatttga   360
ctttattagc ttcgattctc tctgatattt gtttctagaa tttgatctga tcagcgatgt   420
ttacttgttc cttgtttttt gtttttttcat tgacttcttg tggggacaaa aaaaaacaat   480
caaatatctt tcgatttcgt tgttcttctc ttttcgtta tctgatagtg accgatttga   540
tcctgtatcg ttgctattca gatgctaatc atctccttaa ttgtgaattt ttttgttgtt   600
atttagtgaa tcttgttaca agtctgttgt aggtttattt ttgccattaa gctactttga   660
tcgactttag aatctatttg atgataagta attaaacatg ttttagtgat tgttaagtaa   720
gtcatttagt catgttttg gagcatcgag tgaagatcta atatagcttt aagcttgcat    780
cttctcatta cgctccatac actaattttc acatcatatt tgctattgga aacagataag   840
tttttggttc ttgtttccat tgctacttgt gatgcacatc ctcacaattt tctctcagtt   900
ttggttctta tttctctgga acagtttgat ttgttagatt gtaacactat gaagaaaccc   960
tgaagctaaa cttgtttata aacgcaggtg ataaacaaga                        1000
```

<210> SEQ ID NO 5
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 13610771

<400> SEQUENCE: 5

```
atagagtttt actatgcttt tggaatcttt cttctaatgt gccaactaca gagaaataca    60
tgtattacca ctaggaatcg gaccatatca tagatatcag gattagataa ctagttctcg   120
tcgctatcac ttcgcattaa gttctagtaa ttgttaaaga ttctaatttt ttactaaaca   180
aaaactaaat caacatcaaa tatgcaaagt gtgtgttgtc cacacaagtg actcaaagta   240
tacgcaggtg ggattggacc atattattgc aaatcgtttc cgaaccactc atatttcttt   300
ttttctctcc ttttttatc cggagaatta tggaaccact tcatttcaac ttcaaaacta   360
attttttggt tcagtgatca aatacaaaaa aaaaaaaaa gttatagata ttaaatagaa   420
aactattcca atcttaaaaa tacaaatgaa accataattt taatttatac aaaactatt   480
aattagctaa gggttgtctt aacgtttaga aaataaaaaa ttatgattgt ctgtttaaaa   540
ttacaatgaa tgaataaaaa aaatatgcaa tgaatgaaag aataaatttt gtacatccga   600
tagaatgaga aaatgaattt tgtacaaacc actcaagaat tcaaaacaat tgtcaaagtt   660
ttcttctcag ccgtgtgtcc tcctctccta gccgccacat ctcacacact aatgctaacc   720
acgcgatgta accgtaagcg ctgagttttt gcatttcaga tttcacttcc accaaacaaa   780
actcgccacg tcatcaatac gaatcattcc gtataaacgt ctagattctt tacagcctac   840
aatgttctct tctttggtcg gccattattt aacgctttga acctaaatct agcccagcca   900
acgaagaaga cgaagcaaat ccaaaccaaa gttctccatt ttcgtagctt ctttaagctt   960
tttcagtatc atagagacac tttttttttt ttgattagaa                        1000
```

<210> SEQ ID NO 6
<211> LENGTH: 1000

```
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 23547574

<400> SEQUENCE: 6
atagagtttt actatgcttt tggaatcttt cttctaatgt gccaactaca gagaaataca      60
tgtattacca ctaggaatcg gaccatatca tagatatcag gattagataa ctagttctcg     120
tcgctatcac ttcgcattaa gttctagtaa ttgttaaaga ttctaatttt ttactaaaca     180
aaaactaaat caacatcaaa tatgcaaagt gtgtgttgtc cacacaagtg actcaaagta     240
tacgcaggtg ggattggacc atattattgc aaatcgtttc cgaaccactc atatttcttt     300
ttttctctcc ttttttttatc cggagaatta tggaaccact tcatttcaac ttcaaaacta     360
atttttttggt tcagtgatca aatacaaaaa aaaaaaaaaa gttatagata ttaaatagaa     420
aactattcca atcttaaaaa tacaaatgaa accataattt taatttatac aaaactattt     480
aattagctaa gggttgtctt aacgtttaga aaataaaaaa ttatgattgt ctgtttaaaa     540
ttacaatgaa tgaataaaaa aaatatgcaa tgaatgaaag aataaatttt gtacatccga     600
tagaatgaga aaatgaattt tgtacaaacc actcaagaat tcaaaacaat tgtcaaagtt     660
ttcttctcag ccgtgtgtcc tcctctccta gccgccacat ctcacacact aatgctaacc     720
acgcgatgta accgtaagcg ctgagttttt gcatttcaga tttcacttcc accaaacaaa     780
actcgccacg tcatcaatac gaatcattcc gtataaacgt ctagattctt tacagcctac     840
aatgttctct tctttggtcg gccattattt aacgctttga acctaaatct agcccagcca     900
acgaagaaga cgaagcaaat ccaaaccaaa gttctccatt ttcgtagctt ctttaagctt     960
tttcagtatc atagagacac tttttttttt ttgattagaa                          1000

<210> SEQ ID NO 7
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 12663481

<400> SEQUENCE: 7
tccaatagct atgacttgtc gctgtaagaa taatctttttt aaaggcccttt tctcggacca     60
ttatatttct tatctcatgt gaataattat aatgtaataa aaaacaaaag ttttctttgt     120
gttttttttc gtcttcagat ttatatgtaa gtggggagag taataagaga cgttcccggg     180
ggtctttggc cattgcaggt cgacaaacaa ttttgcctct ccgtttcatt aatggacggt     240
ccaatagaac ctttatatta ttctacaaat ataacaact ctatgataat atcaaaatat      300
gagatagaat cacatctgca taacttttttc ttatgaaatt agggaataca gaatatctat     360
atacatataa tatttgatag accgatcatg aggaggaagc atcataacct aatttcttaa     420
atgttttttag ttaaataatg tcaatccatc caaggtaatt gccgagtttt tcattgcgac     480
tgctctaata acatgataaa atctattaaa aacaaatata ctatgagctt agacaataac     540
ccatcaaaaa aaaataaccc atatatattt ttattaaaaa gaagagaaat gcttcttaaa     600
acttctgcc tcgcatataa tcgttatttt cctagaaaaa aaatcgtatc ttaacttcac     660
atcaaacgta atagaagttt acgtttgatt gtgacattat caatatatat catctgcatt     720
```

```
gcacgcggat caaatatttg gccagtctaa atagaattag aggagaataa agtaaaataa      780
aacaacaggt ttgaccaatt aattaaaaaa ggggcgagcc aacttgtcgt atatcattcg      840
tacagtggcc atttactaag tgtgtgaccc tatatatata aatcatatcc ttcatgcaaa      900
gtcacctgaa catttcatat ataagaagat atacaagcct accaaacata acaaaacata      960
ttttaaacac cagcaagttt atattgcaaa gcgtttcatc                          1000
```

<210> SEQ ID NO 8
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres cDNA ID no. 23500661

<400> SEQUENCE: 8

```
tccaatagct atgacttgtc gctgtaagaa taatctttttt aaaggcccttt tctcggacca       60 ttatatttct tatctcatgt gaataattat aatgtaataa aaaacaaaag ttttctttgt      120
gttttttttc gtcttcagat ttatatgtaa gtggggagag taataagaga cgttcccggg      180
ggtctttggc cattgcaggt cgacaaacaa ttttgcctct ccgtttcatt aatggacggt      240
ccaatagaac cttatatatta ttctacaaat ataacaact ctatgataat atcaaaatat      300
gagatagaat cacatctgca taactttttc ttatggaatt agggaataca gaatatctat      360
atacatataa tatttgatag accgatcatg aggaggaagc atcataacct aatttcttaa      420 atgttttttag ttaaataatg tcaatccatc caaggtaatt gccgagtttt tcattgcgac      480
tgctctaata acatgataaa atctattaaa aacaaatata ctatgagctt agacaataac      540
ccatcaaaaa aaaataaccc atatatattt ttattaaaaa gaagagaaat gcttcttaaa      600
actttctgcc tcgcatataa tcgttatttt cctagaaaaa aaatcgtatc ttaacttcac      660
atcaaacgta atagaagttt acgtttgatt gtgacattat caatatatat catctgcatt      720
gcacgcggat caaatgcttg gccagtctaa atagaattag aggagaataa agtaaaataa      780
acaacaggtt tgaccaatta attaaaaaag gggcgagcca acttgtcgta tatcattcgt      840
acagtggcca tttactaagt gtgtgaccct atatatata atcatatcct tcatgcaaag      900
tcacctgaac atttcatata taagaagata tacaagccta ccaaacataa caaaacatat      960
tttaaacacc agcaagttta tattgcaaag cgtttcatc                            999
```

<210> SEQ ID NO 9
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres cDNA ID no. 12574427

<400> SEQUENCE: 9

```
gggtccctct tttagatttc cctgggtccc gcggatccaa attttaatgt ggacgtcaaa       60 tcctttttttt ttattattat ttgtccactt tcctcttctt ctttttttt tttttgccat      120 ttgaaaacga tataaataaa agtgtttgga taacataaaa tttctagagt catatggatg      180
gatatactac tagttaggcg tatactaatt ttctcgtcaa cccacaaaac ccgatcttaa      240
tattattcta tgaattgcat ttgaaccata aattttaaat tagaaactga ccaatcacat      300
ggaacaatat aaaattgtct tagtggttag tacttaatac aaataagacc aatccgaaga      360
```

```
accgagccgg ttaagtttaa acacgctact atgaattgta atggtgtatg accaaaatta      420
gcttctttaa tcttctggtt tattattctt aacagtgagt gattccattt tcagttttt       480 ttttccaatc acactaatga gtaatgacga gattttgact aagaagttgt atatatctca      540
cgatggtata ttttttattttt ttggattcct ttgtacggat ttcttctcct ctattattta   600
ttcgatttta ggaatattat tttctctatg atattcgcat aggccctcca ccggattttc     660
cataaaatct ctatttatta atactattgt tttcaaagat aaaagttcaa ttttttcaac     720
cctaaaagca cggcacataa aaatatataa ttttcacatt aataggaacc aaagattttg     780
ttggattttc ctcgctggag attttttcaaa ataaaaattg aaaaaaccaa aaagacacac    840
tcataaaaga tttattttag agaacaaaaa aatcagaaat ataaaaaact gtcttaagga     900
agagaaagga acaaaagaaa acagatgtga gctcttcttc ttcgtcttct tctctctatt     960
ttattctcat cctctcctca cagttactat aagctcgtct                          1000

<210> SEQ ID NO 10
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres cDNA ID no. 23457514

<400> SEQUENCE: 10
gggtcccctt ttagatttcc ctgggtcccg cggatccaaa ttttaatgtg gacgtcaaat      60 ccttttttt attattattt gtccactttc ctcttcttct tttttttttt tttttgccat      120
ttgaaaacga tataaataaa agtgtttgga taacataaaa tttctagagt catatggatg     180
gatatactac tagttaggcg tatactaatt ttctcgtcaa ccccacaaac cccgatctta     240
atattattct atgaattgca tttgaaccat aaattttaaa ttagaaactg accaatcaca     300
tggaacaata taaaattgtc ttagtggtta gtacttaata caaataagac caatccgaag     360
aaccgagccg gttaagttta aacacgctac tatgaattgt aatggtgtat gaccaaaatt     420
agcttcttta atcttctggt ttattattct taacagtgag tgattccatt tcagttttt      480 tttttccaat cacactaatg agtaatgacg agattttgac taagaagttg tatatatctc     540
acgatggtat attttttattt tttggattcc tttgtacgga tttcttctcc tctattattt    600
attcgatttt aggaatatta ttttctctat gatattcgca taggccctcc accggattt       660 ccataaaatc tctatttatt aatactattg ttttcaaaga taaaagttca attttttcaa     720
ccctaaaagc acggcacata aaatatata attttcacat taataggaac caaagatttt      780
gttggatttt cctcgctgga gattttttcaa ataaaaatt gaaaaaacca aaagacaca      840 ctcataaaag atttatttta gagaacaaaa aaatcagaaa tataaaaaac tgtcttaagg     900
aagagaaagg aacaaaagaa acagatgtg agctcttctt cttcgtcttc ttctctctat     960
tttattctca cctctcctc acagttacta taagctcgtc t                        1001

<210> SEQ ID NO 11
<211> LENGTH: 673
<212> TYPE: DNA
<213> ORGANISM: Arabidopsis thaliana
<220> FEATURE:
<221> NAME/KEY: misc_feature
<222> LOCATION: (1)..(673)
<223> OTHER INFORMATION: Ceres cDNA ID no. 12667371
```

```
<400> SEQUENCE: 11
aatgagctaa atcacaatag ctccagcgaa aatgcatgat ttttaaaatg cttctttcaa      60
tgatatagtt ttattgtaat ggaaaaatat ttagcaaata gattataaac ttacatgaga     120
caagtataaa taattattat aaacttatta agtttaagat caaggctttt gtgcaatgta     180
tcaatgaatg ttagatgtga tatgatgaaa gcaatgtttt aaacacatac atagtcattg     240
atcggaatgt gtgttattag aaatgcatgc ctaagccgat agggttatct atgtttggtc     300
ttggacatta tagccaaatt tcgaatctaa ttcttccaat atatattttt ttttttttgc     360
ttagggccac tactagtatt gcttatcaat tttaagagct catgaaaatg caacaatata     420
gtagttgcaa atccttgttt caagagaaat caagggcca cttgtgaatt gaataataat      480
aatatttgca ataaccttt cactaaacca taccaacaaa accacacaga tttggcaaag      540
acataacctt tgggagacgt gaaaaggctc aaaatttgac aattgtcctt acaaattcgc     600
tcattagtgc aattgtgaga tttgtttgca tccaaatcca attcataact cacactcgtc     660
tcaaattcga aaa                                                       673

<210> SEQ ID NO 12
<211> LENGTH: 573
<212> TYPE: DNA
<213> ORGANISM: Arabidopsis thaliana
<220> FEATURE:
<221> NAME/KEY: misc_feature
<222> LOCATION: (1)..(573)
<223> OTHER INFORMATION: Ceres cDNA ID no. 23494405

<400> SEQUENCE: 12
gattataaac ttacatgaga caagtataaa taattattat aaacttatta agtttaagat      60
caaggctttt gtgcaatgta tcaatgaatg ttagatgtga tatgatgaaa gcaatgtttt     120
aaacacatac atagtcattg atcggaatgt gtgttattag aaatgcatgc ctaagccgat     180
agggttatct atgtttggtc ttggacatta tagccaaatt tcgaatctaa ttcttccaat     240
atatattttt ttttttttgc ttagggccac tactagtatt gcttatcaat tttaagagct     300
catgaaaatg caacaatata gtagttgcaa atccttgttt caagagaaat caagggcca     360 cttgtgaatt gaataataat aatatttgca ataaccttt cactaaacca taccaacaaa     420
accacacaga tttggcaaag acataacctt tgggagacgt gaaaaggctc aaaatttgac     480
aattgtcctt acaaattcgc tcattagtgc aattgtgaga tttgtttgca tccaaatcca     540
attcataact cacactcgtc tcaaattcga aaa                                  573

<210> SEQ ID NO 13
<211> LENGTH: 397
<212> TYPE: DNA
<213> ORGANISM: Arabidopsis thaliana
<220> FEATURE:
<221> NAME/KEY: misc_feature
<222> LOCATION: (1)..(397)
<223> OTHER INFORMATION: Ceres cDNA ID no. 12558510

<400> SEQUENCE: 13
agtgtatttg aaaacgacat tgaagaatta atatattttt ttttaatttt agtttttat       60 agtacaaata ttaaaacaaa caatcctacc atatcataac atttgtaaat aacatttaa      120 gttttgttt gagttttaat taatttcta tgacaaaaaa atgaagtcaa tagactaagt      180
gaatcatata gtataaataa acacaattta aatagtttca aataaattta gaagaataa      240 aacaaataga aatcagaagg tgtctgtttc ctcctcgcaa catacgatca aagagaaaca     300
```

```
acttgaccct ttacattgct caagagctca tctcttccct ctacaaaaat ggccgcacgt    360
ctccaacctt ctcccaactc cttcttccgc catcatc                             397
```

<210> SEQ ID NO 14
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 23546169

<400> SEQUENCE: 14

```
aagaccttt cgcaagtcat caaagcacaa tcccacaccg tacgttttgg tttacctgtc     60
tgtcagataa cgaccgtctc aatatcggat cttaattaca tttatgaata actcgactgc   120
gcctccgcaa aataagaaga aattgaatat cgaacatttc aacctcaggc atcacatcca   180
agtgattcct tatgttgatg taaaaatggg atatataggg ccaatcagat tcatataata   240
atattcataa atcagattcg taatgcagta tttatcagct ccataaatga tcctagagaa   300
tcttatgtaa agtggatcat gcacgtatct ttatcttctc aaaccttcga agaaacccct   360
caaaacgtta ttatctaccg aatacattta atccatatag cgtgacaaaa gaacagagcc   420
cgtagttgat aaaaagcatg agagtgatga tgaatgtgaa gcactgagag agatctcacc   480
gcttgccgta taacgtctcc gtctccgtct ttgtcggcat tcgtcagctg aactcttaaa   540
cgtgtcgact gttgtctcga tccaagataa cactgtagct gacagttaca tttagagttt   600
gtctccatct catgcgcaac gcagcaccgt caattttctg tgaggatact aaactactat   660
gtaatgatgt cgacaaaaga gtgaaggtg ggtcccgcat tgcccatgt ggttatggtc     720 aacgtgtcaa agtactagcg gctgtgtttt aatccgatct ttttctatca atccatggtc   780
ccgtagaata atttcactat ttttttcactt ggctggtgtc aacttagaga ccaataatat   840
atacacttat cttttacagt ctaaatttaa ttatgcggct taccattata taagactctg   900
gtagactact ctcattatat acattataaa gatactgatg agtggttctt gtttaatgga   960
gttttaaatt taaaaatatt tggtaaccga gtggatcatc                         1000
```

<210> SEQ ID NO 15
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 12577385

<400> SEQUENCE: 15

```
gttttgtaat tctttggggg ctaataggat attttatttt cttggtttcg tctattgttg     60
tttttctatt tatggttggg cttttagaac tctggacagg cccatgtcat atgttttccc   120
ttctccttat attttttcatt tttcattttg ttaaattaat gcataatatc caaaaacaat   180
ttaaattttt gaaggaaccc tttagttacg gctccgaagc tttcacaagt gagaatgtga   240
gatcaaagaa ggcaaatgga ggattttaaa agttaaaatc atcttttatc tgcaaaagtt   300 gacaatttt ttgtatcaaa tctaaatcat caaactctct taaactacaa gagcataaca    360
acctctatgt aatccatgaa ataatctgct tgaaggacat aacataaatc attatgccta   420
gagtgactaa cttcaatcaa atcctcttaa ctctagctcc cttacaatgg tatcgtaaaa   480
```

```
cattatgcat tagggattgt tgtcctagga aaataaaata aaaatcccca cagaccaact      540
accattttaa cttaaaaata agcttcgtcc gcgacgaatt gttttccatc ctaaaaatag      600
aatggtgtaa tctgctaatg gtttagttcc attaacttgc aagttctatt gaaagcctaa      660
atgtcaataa agatattaaa attcggagtc aaaagacaaa tgaatcaaaa gcaacaagac      720
aagtcagctc cattcttcac tacccatctt ttacaataaa tcatctctct tttcacaaat      780
ttcaaactac tctcattgcc ctttagcttt gttatagagc caacactaca gagagactca      840
cacacttgtt tcaataatta aatctgaatt tggctcttct tataaactaa tgtctgcagg      900
tcttcttatc tctctcactc accaccatct tcttcctcga ttgtcaaaac cctagatcga      960
aatcttatct ctctaatctg ttgttacagt tcgtagagtc                          1000

<210> SEQ ID NO 16
<211> LENGTH: 921
<212> TYPE: DNA
<213> ORGANISM: Arabidopsis thaliana
<220> FEATURE:
<221> NAME/KEY: misc_feature
<222> LOCATION: (1)..(921)
<223> OTHER INFORMATION: Ceres CDNA ID no. 13611030

<400> SEQUENCE: 16
aaagttttga attattggga atcaatttcg aagttttgta attctttggg ggctaatagg       60
atattttatt ttcttggttt cgtctattgt tgttttttcta tttatggttg ggcttttaga     120
actctggaca ggcccatgtc atatgttttc ccttctcctt atattttca ttttttcattt     180 tgttaaatta atgcataata tccaaaaaca atttaaattt ttgaaggaac cctttagtta     240
cggctccgaa gctttcacaa gtgagaatgt gagatcaaag aaggcaaatg gaggatttta     300
aaagttaaaa tcatctttta tctgcaaaag ttgacaattt ttttgtatca aatctaaatc     360
atcaaactct cttaaactac aagagcataa caacctctat gtaatccatg aaataatctg     420
cttgaaggac ataacataaa tcattatggc tagagtgact aacttcaatc aaatcctctt     480
aactctagct cccttacaat ggtatcgtaa acattatgc attagggatt gttgtcctag      540
gaaaataaaa taaaaatccc cacagaccaa ctaccatttt aacttaaaaa taagcttcgt     600
ccgcgacgaa ttgttttcca tcctaaaaat agaatggtgt aatctgctaa tggtttagtt     660
ccattaactt gcaagttcta ttgaaagcct aaatgtcaat aaagatatta aaattcggag     720
tcaaaagaca aatgaatcaa agcaacaag acaagtcagc tccattcttc actacccatc     780
ttttacaata aatcatctct cttttcacaa atttcaaact actctcattg cccttttagct     840 ttgtttataga gccaacacta cagagagact cacacacttg tttcaataat taaatctgaa     900
tttggctctt cttataaact a                                                 921

<210> SEQ ID NO 17
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres CDNA ID no. 13497685

<400> SEQUENCE: 17
aaaaaggatg ggtaatggga cctatttttcc ccaacatccc acatgcacac ttccctctcc       60
attctctcac attatatttct ttcattctaa tttatccatt ccgtgtgtaa catattcact     120
aataatctca tctcactaac tcattcattg attgtgatat gtttatctag aattagtgtt     180
```

```
ttaacactgt gtctacatat gatttccttt tcattgtatg tgaacatgtt aactcactaa      240
tcattttgta ttttcgagtt aacatgagtc tccacttcgg tagactaaag taaagatagg      300
tttgagtata ataaagttta aaatttgctt taaaatcaat atttataaat aagtttttat      360
cataagtgat ttttgtatgt tatattggac cttgtataaa cagactacag aagaaaatta      420
tttatgagaa cttgtaatgt tagagtggac ctcgtataaa ctaattatgt gggcttttac      480
cataaactat ttatgaaaat tattatggcc cacaccacta taactaaagc ccacatattt      540
agcagcccag tttcattgta agagacatgt tcgctctgga actagaattt tctggttttt      600
gggtatttgt tttcttatgt gtagagaaat gatggtaacg attaaatgtt gtgtattaca      660
atttacaatg gtaagacgat taatatattt acacacaatt ttgttgttgc tgtaacacgt      720
tagtgtgtgt gatgatagaa tttcataaag ctttaactac gagggcaaa atgttaattc       780 taaatagttg acagcagaaa aagatatgta tacataatat aaggattaaa acgtaaataa      840
taataaataa ggcgagttaa attaaaaccc tgttaaaacc ctagcttgaa acacatgtat      900
aaaaacactt gcgagcgcag cttcatcgcc atcgccattc tctctctcat caaaagcttt      960
tctccttgat tttcgcattc tttagagtct taacgcaaag                           1000

<210> SEQ ID NO 18
<211> LENGTH: 47
<212> TYPE: DNA
<213> ORGANISM: Arabidopsis thaliana
<220> FEATURE:
<221> NAME/KEY: misc_feature
<222> LOCATION: (1)..(47)
<223> OTHER INFORMATION:
      At1g63940_oligo_5'_sequence_for_cloning_into_CRS815

<400> SEQUENCE: 18
ttcaccagtc gattggcccg atcggccaaa gttttgaatt attggga                    47

<210> SEQ ID NO 19
<211> LENGTH: 47
<212> TYPE: DNA
<213> ORGANISM: Arabidopsis thaliana
<220> FEATURE:
<221> NAME/KEY: misc_feature
<222> LOCATION: (1)..(47)
<223> OTHER INFORMATION:
      At1g63940_oligo_3'_sequence_for_cloning_into_CRS815

<400> SEQUENCE: 19
catgccattg cactggccct gcaggcctag tttataagaa gagccaa                    47

<210> SEQ ID NO 20
<211> LENGTH: 38
<212> TYPE: DNA
<213> ORGANISM: Arabidopsis thaliana
<220> FEATURE:
<221> NAME/KEY: misc_feature
<222> LOCATION: (1)..(38)
<223> OTHER INFORMATION:
      At1g63940_oligo_5'_sequence_for_cloning_into_Newbin4-35S-GFP

<400> SEQUENCE: 20
ccggcgccag tcgattgggt tttgtaattc tttggggg                              38

<210> SEQ ID NO 21
<211> LENGTH: 38
<212> TYPE: DNA
<213> ORGANISM: Arabidopsis thaliana
```

```
<220> FEATURE:
<221> NAME/KEY: misc_feature
<222> LOCATION: (1)..(38)
<223> OTHER INFORMATION:
      At1g63940_oligo_3'_sequence_for_cloning_into_Newbin4-35S-GFP

<400> SEQUENCE: 21
cgcgcgccag tgcaatggga ctctacgaac tgtaacaa                                38

<210> SEQ ID NO 22
<211> LENGTH: 47
<212> TYPE: DNA
<213> ORGANISM: Arabidopsis thaliana
<220> FEATURE:
<221> NAME/KEY: misc_feature
<222> LOCATION: (1)..(47)
<223> OTHER INFORMATION:
      At4g25630_oligo_5'_sequence_for_cloning_into_CRS815

<400> SEQUENCE: 22
ttcaccagtc gattggcccg atcggccaaa aggatgggt aatggga                       47

<210> SEQ ID NO 23
<211> LENGTH: 47
<212> TYPE: DNA
<213> ORGANISM: Arabidopsis thaliana
<220> FEATURE:
<221> NAME/KEY: misc_feature
<222> LOCATION: (1)..(47)
<223> OTHER INFORMATION:
      At4g25630_oligo_3'_sequence_for_cloning_into_CRS815

<400> SEQUENCE: 23
catgccattg cactggccct gcaggccctt tgcgttaaga ctctaaa                      47

<210> SEQ ID NO 24
<211> LENGTH: 38
<212> TYPE: DNA
<213> ORGANISM: Arabidopsis thaliana
<220> FEATURE:
<221> NAME/KEY: misc_feature
<222> LOCATION: (1)..(38)
<223> OTHER INFORMATION:
      At4g25630_oligo_5'_sequence_for_cloning_into_Newbin4-35S-GFP

<400> SEQUENCE: 24
ccggcgccag tcgattggaa aaggatggg taatggga                                 38

<210> SEQ ID NO 25
<211> LENGTH: 38
<212> TYPE: DNA
<213> ORGANISM: Arabidopsis thaliana
<220> FEATURE:
<221> NAME/KEY: misc_feature
<222> LOCATION: (1)..(38)
<223> OTHER INFORMATION:
      At4g25630_oligo_3'_sequence_for_cloning_into_Newbin4-35S-GFP

<400> SEQUENCE: 25
cgcgcgccag tgcaatggct ttgcgttaag actctaaa                                38
```